(12) United States Patent
Kawai et al.

(10) Patent No.: US 8,846,870 B2
(45) Date of Patent: Sep. 30, 2014

(54) ANTI-HS6ST2 ANTIBODIES AND USES THEREOF

(75) Inventors: Shigeto Kawai, Tokyo (JP); Naoki Kimura, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 215 days.

(21) Appl. No.: 12/998,988

(22) PCT Filed: Dec. 22, 2009

(86) PCT No.: PCT/JP2009/071271
§ 371 (c)(1), (2), (4) Date: Jun. 21, 2011

(87) PCT Pub. No.: WO2010/074049
PCT Pub. Date: Jul. 1, 2010

(65) Prior Publication Data
US 2011/0262929 A1    Oct. 27, 2011

(30) Foreign Application Priority Data
Dec. 22, 2008 (JP) .................................. 2008-324883

(51) Int. Cl.
| C07K 16/00 | (2006.01) |
| G01N 33/574 | (2006.01) |
| C07K 16/30 | (2006.01) |
| C07K 16/40 | (2006.01) |
| C07K 16/28 | (2006.01) |

(52) U.S. Cl.
CPC .......... *C07K 16/30* (2013.01); *G01N 33/57438* (2013.01); *G01N 33/57423* (2013.01); *C07K 2317/73* (2013.01); *G01N 33/57449* (2013.01); *C07K 16/40* (2013.01); *C07K 16/28* (2013.01); *C07K 2317/732* (2013.01)
USPC ..................................................... 530/387.9

(58) Field of Classification Search
CPC ........... C12Q 1/6886; C12Q 2600/106; C12N 5/0693; C12N 5/0618; G01N 33/5014
See application file for complete search history.

(56) References Cited

U.S. PATENT DOCUMENTS 7,150,981 B2 * 12/2006 Habuchi et al. ............... 435/193

FOREIGN PATENT DOCUMENTS

EP    1 295 946 A1    3/2003

OTHER PUBLICATIONS

International Search Report dated Feb. 16, 2010, in PCT/JP2009/071271, 4 pages.

Backen et al., "Heparan sulphate synthetic and editing enzymes in ovarian cancer," British Journal of Cancer, 2007, 96(10):1544-1548.
Belting et al., "Heparan sulphate proteoglycan as a plasma membrane carrier," TRENDS in Biochemical Sciences, Mar. 2003, 28(3):145-151.
Bernfield et al., "Functions of Cell Surface Heparan Sulfate Proteoglycans," Annu. Rev. Biochem., 1999, 68:729-777.
Fransson et al., "Novel aspects of glypican glycobiology," CMLS, Cell. Mol. Life Sci., 2004, 61:1016-1024.
Gallagher, John T., "Heparan sulfate: growth control with a restricted sequence menu," Journal of Clinical Investigation, Aug. 2001, 108(3):357-361.
Habuchi et al., "Purification and Characterization of Heparan Sulfate 6-Sulfotransferase from the Culture Medium of Chinese Hamster Ovary Cells," Journal of Biological Chemistry, Feb. 24, 1995, 270(8):4172-4179.
Habuchi et al., "The Occurrence of Three Isoforms of Heparan Sulfate 6-O-Sulfotransferase Having Different Specificities for Hexuronic Acid Adjacent to the Targeted N-Sulfoglucosamine," Journal of Biological Chemistry, Jan. 28, 2000, 275(4):2859-2868.
Habuchi et al., "Biosynthesis of heparan sulphate with diverse structures and functions: two alternatively spliced forms of human heparan sulphate 6-O-sulphotransferase-2 having different expression patterns and properties," Biochem. J., 2003, 371:131-142.
Habuchi et al., "Molecular Characterization and Expression of Heparan-sulfate 6-Sulfotransferase," Journal of Biological Chemistry, Apr. 10, 1998, 273(15):9208-9213.
Iozzo et al., "Proteoglycans of the extracellular environment: clues from the gene and protein side offer novel perspectives in molecular diversity and function," FASEB J., Apr. 1996, 10(5):598-614.
Jayson et al., "Heparan Sulfate Undergoes Specific Structural Changes during the Progression from Human Colon Adenoma to Carcinoma in Vitro," Journal of Biological Chemistry, Jan. 2, 1998, 273(1):51-57.
Jemth et al., "Oligosaccharide Library-based Assessment of Heparan Sulfate 6-O-Sulfotransferase Substrate Specificity," Journal of Biological Chemistry, Jul. 4, 2003, 278(27):24371-24376.
Johnson et al., "Heparan Sulfate is Essential to Amphiregulin-induced Mitogenic Signaling by the Epidermal Growth Factor Receptor," Journal of Biological Chemistry, Oct. 28, 1994, 269(43):27149-27154.
Kleeff et al., "The Cell-surface Heparan Sulfate Proteoglycan Glypican-1 Regulates Growth Factor Action in Pancreatic Carcinoma Cells and is Overexpressed in Human Pancreatic Cancer," J. Clin. Invest., Nov. 1998, 102(9):1662-1673.
Ledin et al., "Heparan Sulfate Structure in Mice with Genetically Modified Heparan Sulfate Production," Journal of Biological Chemistry, Oct. 8, 2004, 279(41):42732-42741.

(Continued)

*Primary Examiner* — Sharon Wen
(74) *Attorney, Agent, or Firm* — Foley & Lardner LLP

(57) ABSTRACT

The present invention provides antibodies that bind to HS6ST2 proteins, pharmaceutical compositions comprising the antibodies as active ingredients, methods for diagnosing cancer using the antibodies, HS6ST2 proteins conjugated to cytotoxic agents and pharmaceutical compositions comprising the HS6ST2 proteins as active ingredients.

9 Claims, 18 Drawing Sheets

(56) References Cited

OTHER PUBLICATIONS

Lindahl et al., "Regulated Diversity of Heparan Sulfate," Journal of Biological Chemistry, Sep. 25, 1998, 273(39):24979-24982.

Miyake et al., "Expression and Cloning of heparan sulfate-O-sulfotransferase (HS2ST, HS6ST) in various tumor tissues," Cancer Science, Sep. 1, 2000, 91:145, 1595.

Muñoz et al., "Affinity, Kinetic, and Structural Study of the Interaction of 3-O-Sulfotransferase Isoform 1 with Heparan Sulfate," Biochemistry, 2006, 45:5122-5128.

Nagai et al., "Stem domains of heparan sulfate 6-O-sulfotransferase are required for Golgi localization, oligomer formation and enzyme activity," Journal of Cell Science, Jul. 1, 2004, 117(15):3331-3341.

Nagai et al., "Regulation of Heparan Sulfate 6-O-Sulfation by β-Secretase Activity," Journal of Biological Chemistry, May 18, 2007, 282(20):14942-14951.

Nakanishi et al., "Structural differences between heparan sulphates of proteoglycan involved in the formation of basement membranes in vivo by Lewis-lung-carcinoma-derived cloned cells with different metastatic potentials," Biochem. J., 1992, 288:215-224.

Payne et al., "Internalization and Trafficking of Cell Surface Proteoglycans and Proteoglycan-Binding Ligands," Traffic, 2007, 8:389-401.

Yanagishita et al., "Cell Surface Heparan Sulfate Proteoglycans," Journal of Biological Chemistry, May 15, 1992, 267(14):9451-9454.

\* cited by examiner

Figure 5
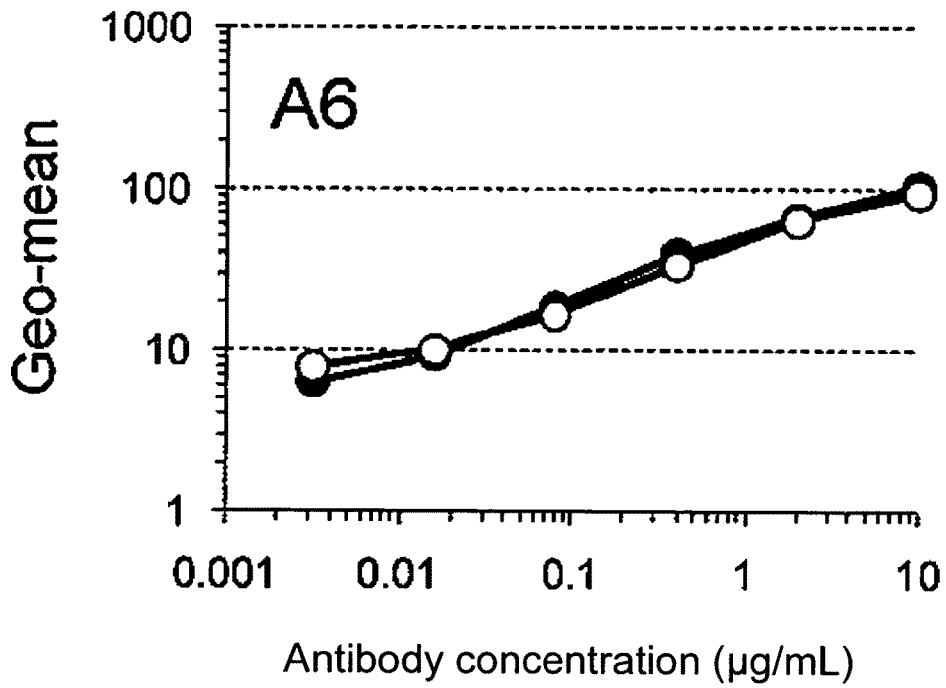
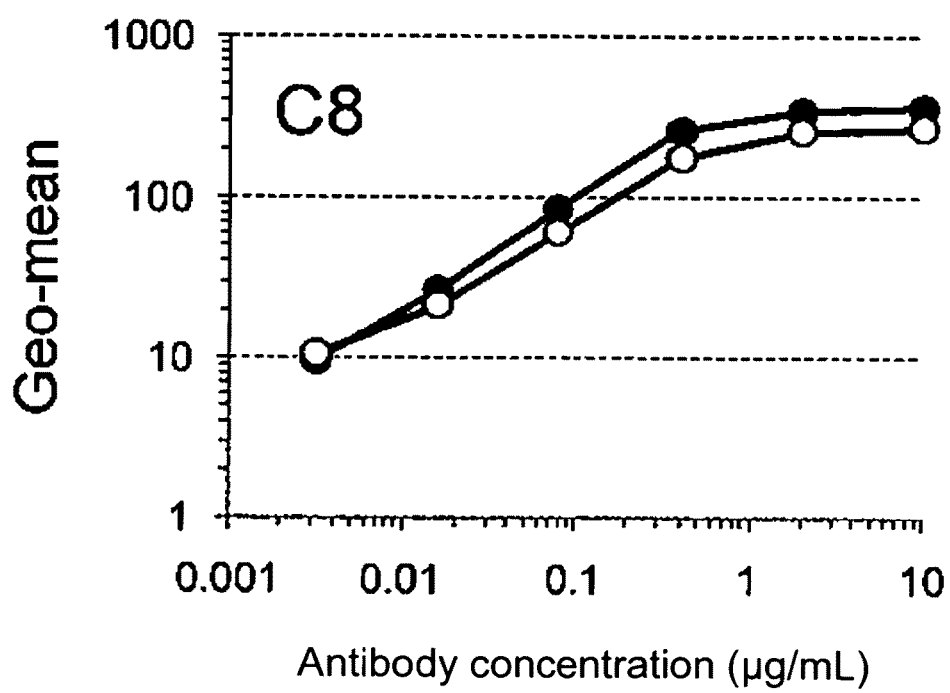

Figure 9
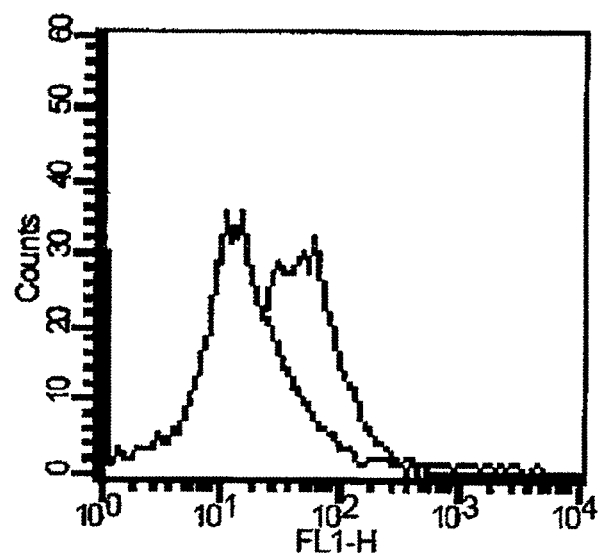
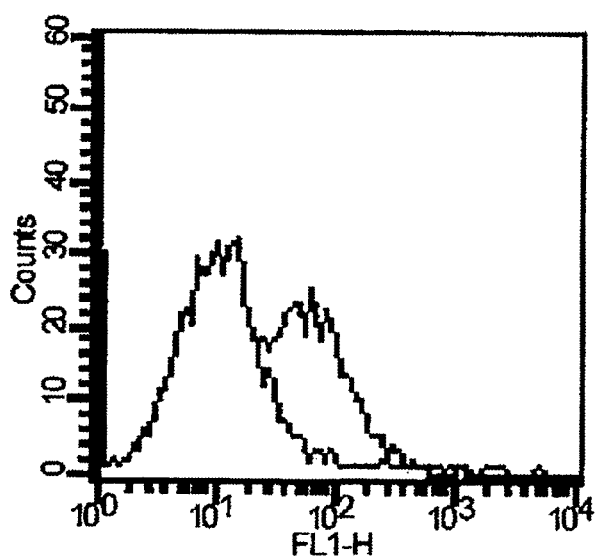

Figure 11
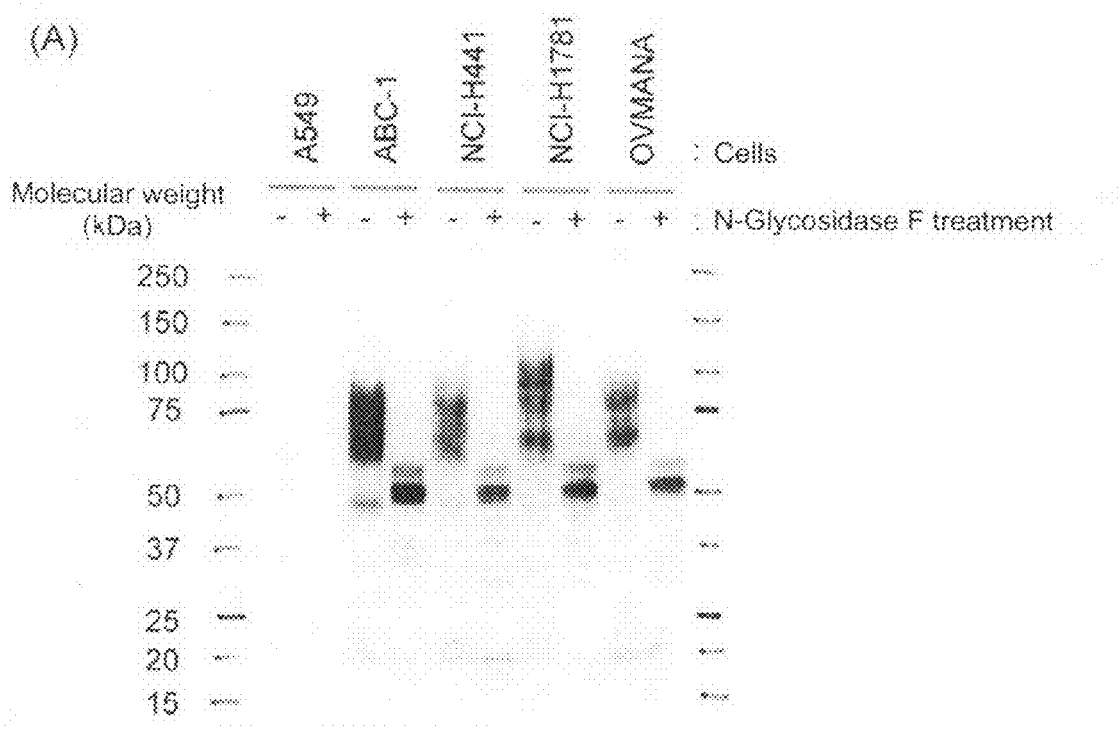
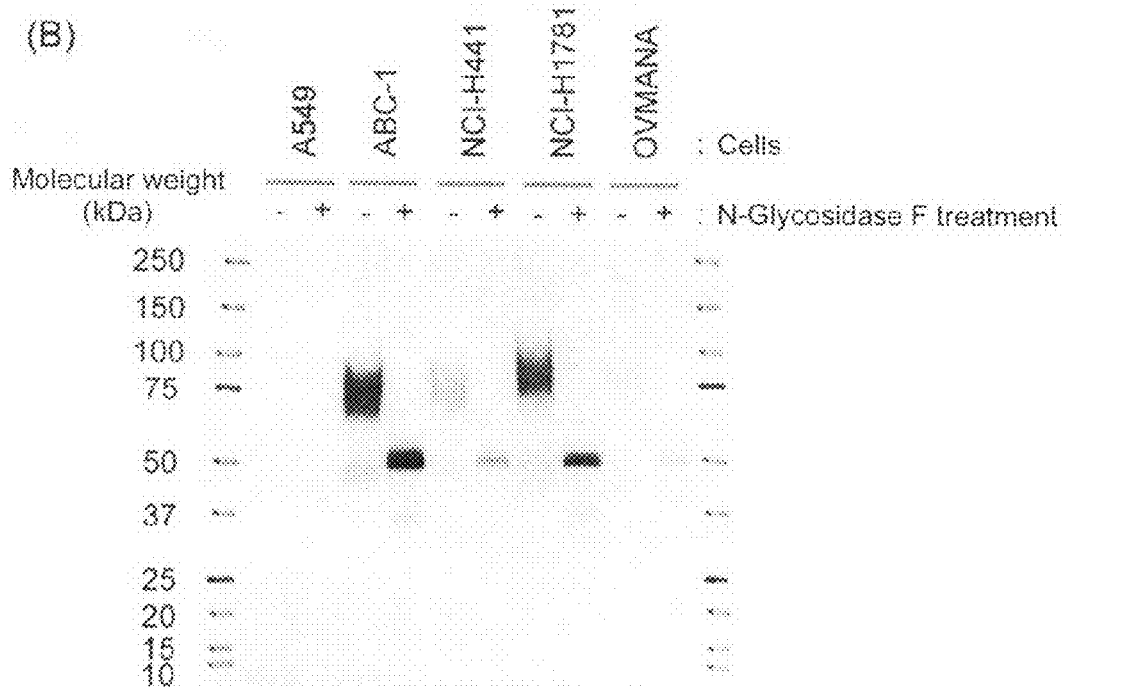

*Figure 14*
(A)
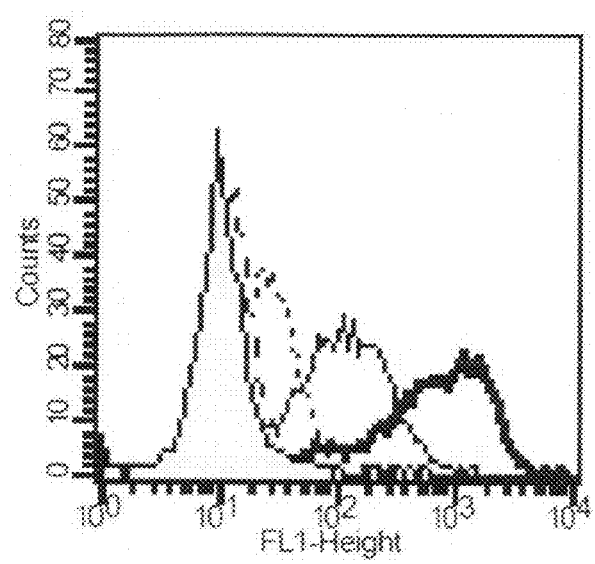
(B)
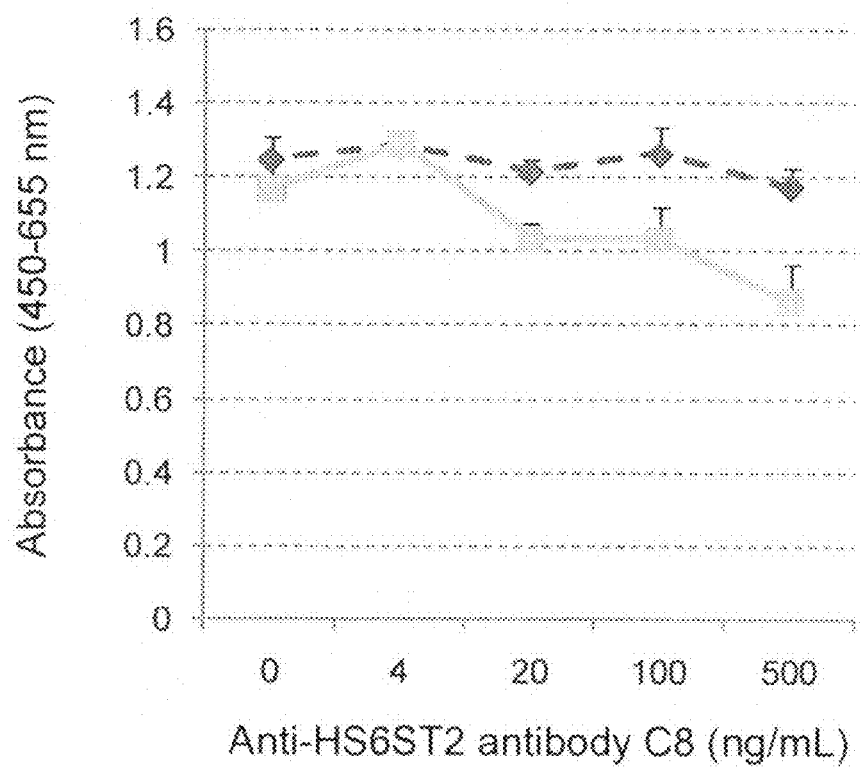

ANTI-HS6ST2 ANTIBODIES AND USES THEREOF

CROSS-REFERENCE TO RELATED APPLICATION

This application is a National Stage application of PCT/JP2009/071271, filed Dec. 22, 2009, which claims priority from Japaneses application JP 2008-324883, filed Dec. 22, 2008.

TECHNICAL FIELD

The present invention relates to antibodies that bind to HS6ST2 proteins and uses thereof. More specifically, it relates to anti-HS6ST2 antibodies conjugated to cytotoxic agents that can be used as anticancer agents.

BACKGROUND ART

Proteoglycans are glycoproteins formed of saccharide chains (glycosaminoglycans) covalently attached to proteins (non-patent document 1). Glycosaminoglycans are polysaccharides typically composed of 40-100 repeating disaccharide units characterized in that they are sulfated to various degrees. Glycosaminoglycans include chondroitin sulfate, dermatan sulfate, heparan sulfate, heparin, keratan sulfate, etc. Among others, heparan sulfate-containing proteoglycans known as heparan sulfate proteoglycans (HSPGs) include syndecans and glypicans expressed on the plasma membrane, and perlecan and agrin secreted in the basement membrane. In mice, heparan sulfate is expressed highly in lung and kidney, and weakly in skeletal muscle, liver, skin and brain (non-patent document 2). HSPGs are known to influence the activity of growth factors and to participate in the growth and differentiation of cells. For example, fibroblast growth factors, heparin-binding epidermal growth factor-like growth factor and amphiregulin transduce signals into cells via receptors of these growth factors as they bind to heparan sulfate (non-patent documents 3, 4, 5, 6). In cancer, HSPGs were also reported to participate in the growth and metastasis of cancer cells (non-patent documents 7, 8).

Heparan sulfate 6-O-sulfotransferase 2 (HS6ST2) is an enzyme that adds a sulfate group to the 6-O position of glucosamine that constitutes heparan sulfate. Known similar enzymes (sulfotransferases) include HS6ST1 and HS6ST3 (non-patent document 9). These members of the HS6ST family are type II membrane proteins localized in the Golgi in cells and act as enzymes (non-patent document 10). HS6ST1 is secreted outside cells as well upon cleavage near the transmembrane domain (non-patent documents 11, 12, 13). HS6ST2 was also suggested to be secreted extracellularly (non-patent document 14). In fact, mouse HS6ST2 (mHS6ST2) is secreted extracellularly as well when it is forcibly expressed in CHO cells (non-patent document 15). Although the secretory mechanism is unknown, the following evidence exists: mHS6ST2 remaining in the Golgi and secreted mHS6ST2 have the same molecular weight; the N-terminal region of mouse HS6ST3 including the transmembrane domain may be cleaved as a signal peptide; and a variant of mHS6ST2 containing an N-terminal extension of 146 amino acids is not secreted extracellularly (non-patent document 15). Generally, it is thought that extracellularly secreted HS6ST2 does not act as an enzyme because the sulfate donor 3'-phosphoadenosine-5'-phosphosulfate is rapidly degraded in blood.

The steric structure of HS6ST2 has not been elucidated, but considered to recognize and bind to partial sequences of heparan sulfate of up to six saccharide chains (non-patent document 16). On the other hand, the crystal structure of mouse HS3ST1, i.e., an enzyme that adds a sulfate group to the 3-O position of glucosamine of heparan sulfate has been analyzed, and it has been shown to bind to heparan sulfate with micromolar affinity (Kd=2.79 μM) (non-patent document 17). Extracellularly secreted HS6ST2 also seems to be able to bind to heparan sulfate on the plasma membrane. Membrane-associated HSPGs are expressed in almost all cells. The expression level is about $10^5$-$10^6$ molecules per cell, and they are mostly taken up by cells with a half-life of 3-8 hours and degraded in lysosomes (non-patent document 18). Indeed, it is known that peptides such as HIV-Tat and bFGF; nucleic acids such as polylysine-DNA complexes; polyamines or anti-HSPG antibodies are taken up by cells via HSPGs (non-patent documents 19, 20, 21).

Thus, it is presumed but has not been verified that secreted HS6ST2 bound to HSPGs is also taken up by cells. Physiological effects of anti-HS6ST2 antibodies and their applications for pharmaceutical uses have not been verified, either.

CITATION LIST

Non-Patent Documents

Non-patent document 1: Proteoglycans of the extracellular environment: clues from the gene and protein side offer novel perspectives in molecular diversity and function. FASEB J. 1996. 10:598-614

Non-patent document 2: Heparan sulfate structure in mice with genetically modified heparan sulfate production. J Biol. Chem. 2004. 279:42732

Non-patent document 3: Functions of cell surface heparan sulfate proteoglycans. Annu Rev Biochem. 1999. 68:729-777

Non-patent document 4: Heparan sulfate: growth control with a restricted sequence menu. J Clin Invest. 2001. 108: 357-361

Non-patent document 5: Heparan sulfate is essential to amphiregulin-induced mitogenic signaling by the epidermal growth factor receptor. J Biol. Chem. 1994. 269:27149

Non-patent document 6: The cell-surface heparan sulfate proteoglycan glypican-1 regulates growth factor action in pancreatic carcinoma cells and is overexpressed in human pancreatic cancer. J Clin Invest. 1998. 102:1662

Non-patent document 7: Heparan sulfate undergoes specific structural changes during the progression from human colon adenoma to carcinoma in vitro. J Biol. Chem. 1998. 273:51

Non-patent document 8: Structural differences between heparan sulphates of proteoglycan involved in the formation of basement membranes in vivo by Lewis-lung-carcinoma-derived cloned cells with different metastatic potentials. Biochem J. 1992. 288:215

Non-patent document 9: The occurrence of three isoforms of heparan sulfate 6-O-sulfotransferase having different specificities for hexuronic acid adjacent to the targeted N-sulfoglucosamine. Biol. Chem. 2000. 275:2859

Non-patent document 10: Regulated diversity of heparan sulfate. J Biol. Chem. 1998. 273:24979

Non-patent document 11: Stem domains of heparan sulfate 6-O-sulfotransferase are required for golgi localization, oligomer formation and enzyme activity. J Cell Sci. 2004. 117:3331

Non-patent document 12: Purification and characterization of heparan sulfate 6-sulfotransferase from the culture medium of Chinese hamster ovary cells. J Biol. Chem. 1995. 270:4172

Non-patent document 13: Molecular characterization and expression of heparan-sulfate 6-sulfotransferase. J Biol. Chem. 1998. 273:9208

Non-patent document 14: Biosynthesis of heparan sulphate with diverse structures and functions: two alternatively spliced forms of human heparan sulphate 6-O-sulphotransferase-2 having different expression patterns and properties. Biochem J. 2003. 371:131

Non-patent document 15: Regulation of heparan sulfate 6-O-sulfation by β-secretase activity. J Biol. Chem. 2007. 282: 14942

Non-patent document 16: Oligosaccharide library-based assessment of heparan sulfate 6-O-sulfotransferase substrate specificity. J Biol. Chem. 2003. 278:24371

Non-patent document 17: Affinity, kinetic, and structural study of the interaction of 3-O-sulfotransferase isoform 1 with heparan sulfate. Biochemistry. 2006. 45:5122

Non-patent document 18: Cell surface heparan sulfate proteoglycans. J Biol. Chem. 1992. 267:9451

Non-patent document 19: Heparan sulfate proteoglycan as a plasma membrane carrier. Trends Biochem Sci. 2003. 28:145

Non-patent document 20: Novel aspects of glypican glycobiology. Cell Mol Life Sci. 2004. 61:1016

Non-patent document 21: Internalization and trafficking of cell surface proteoglycans and proteoglycan-binding ligands. Traffic. 2007. 8:389

SUMMARY OF INVENTION

Technical Problems

An object of the present invention is to provide novel anti-HS6ST2 antibodies. Another object of the present invention is to elucidate physiological effects of the resulting anti-HS6ST2 antibodies and further to apply them to the diagnosis and treatment of diseases, especially cancer.

Solution to Problems

As a result of careful studies to solve the above problems, we prepared novel anti-HS6ST2 antibodies having cytotoxic activity and found that the antibodies are useful for the diagnosis and treatment of cancer, whereby we attained the present invention.

Accordingly, the present invention provides:

[1] An antibody that binds to an HS6ST2 protein.

[2] The antibody of [1] characterized in that it has cytotoxic activity.

[3] The antibody of [1] or [2] characterized in that it is conjugated to a cytotoxic agent.

[4] The antibody of any one of [1]-[3] characterized in that it binds to HS6ST2 bound to heparan sulfate.

[5] The antibody of any one of [1]-[3] characterized in that it binds to HS6ST2 expressed on the plasma membrane.

[6] The antibody of any one of [1]-[5] characterized in that it is any one of the following antibodies:

(1) an antibody (A1) comprising a heavy chain variable region including a heavy chain CDR1 having the amino acid sequence of SEQ ID NO: 64, a heavy chain CDR2 having the amino acid sequence of SEQ ID NO: 65, and a heavy chain CDR3 having the amino acid sequence of SEQ ID NO: 66;

(2) an antibody (A6) comprising a heavy chain variable region including a heavy chain CDR1 having the amino acid sequence of SEQ ID NO: 70, a heavy chain CDR2 having the amino acid sequence of SEQ ID NO: 71, and a heavy chain CDR3 having the amino acid sequence of SEQ ID NO: 72;

(3) an antibody (A10) comprising a heavy chain variable region including a heavy chain CDR1 having the amino acid sequence of SEQ ID NO: 76, a heavy chain CDR2 having the amino acid sequence of SEQ ID NO: 77, and a heavy chain CDR3 having the amino acid sequence of SEQ ID NO: 78;

(4) an antibody (B5) comprising a heavy chain variable region including a heavy chain CDR1 having the amino acid sequence of SEQ ID NO: 82, a heavy chain CDR2 having the amino acid sequence of SEQ ID NO: 83, and a heavy chain CDR3 having the amino acid sequence of SEQ ID NO: 84;

(5) an antibody (B6) comprising a heavy chain variable region including a heavy chain CDR1 having the amino acid sequence of SEQ ID NO: 88, a heavy chain CDR2 having the amino acid sequence of SEQ ID NO: 89, and a heavy chain CDR3 having the amino acid sequence of SEQ ID NO: 90;

(6) an antibody (C8) comprising a heavy chain variable region including a heavy chain CDR1 having the amino acid sequence of SEQ ID NO: 94, a heavy chain CDR2 having the amino acid sequence of SEQ ID NO: 95, and a heavy chain CDR3 having the amino acid sequence of SEQ ID NO: 96;

(7) an antibody (C10) comprising a heavy chain variable region including a heavy chain CDR1 having the amino acid sequence of SEQ ID NO: 100, a heavy chain CDR2 having the amino acid sequence of SEQ ID NO: 101, and a heavy chain CDR3 having the amino acid sequence of SEQ ID NO: 102;

(8) an antibody (A1) comprising a light chain variable region including a light chain CDR1 having the amino acid sequence of SEQ ID NO: 67, a light chain CDR2 having the amino acid sequence of SEQ ID NO: 68, and a light chain CDR3 having the amino acid sequence of SEQ ID NO: 69;

(9) an antibody (A6) comprising a light chain variable region including a light chain CDR1 having the amino acid sequence of SEQ ID NO: 73, a light chain CDR2 having the amino acid sequence of SEQ ID NO: 74, and a light chain CDR3 having the amino acid sequence of SEQ ID NO: 75;

(10) an antibody (A10) comprising a light chain variable region including a light chain CDR1 having the amino acid sequence of SEQ ID NO: 79, a light chain CDR2 having the amino acid sequence of SEQ ID NO: 80, and a light chain CDR3 having the amino acid sequence of SEQ ID NO: 81;

(11) an antibody (B5) comprising a light chain variable region including a light chain CDR1 having the amino acid sequence of SEQ ID NO: 85, a light chain CDR2 having the amino acid sequence of SEQ ID NO: 86, and a light chain CDR3 having the amino acid sequence of SEQ ID NO: 87;

(12) an antibody (B6) comprising a light chain variable region including a light chain CDR1 having the amino acid sequence of SEQ ID NO: 91, a light chain CDR2 having the amino acid sequence of SEQ ID NO: 92, and a light chain CDR3 having the amino acid sequence of SEQ ID NO: 93;

(13) an antibody (C8) comprising a light chain variable region including a light chain CDR1 having the amino acid sequence of SEQ ID NO: 97, a light chain CDR2 having the amino acid sequence of SEQ ID NO: 98, and a light chain CDR3 having the amino acid sequence of SEQ ID NO: 99;

(14) an antibody (C10) comprising a light chain variable region including a light chain CDR1 having the amino acid sequence of SEQ ID NO: 103, a light chain CDR2 having the amino acid sequence of SEQ ID NO: 104, and a light chain CDR3 having the amino acid sequence of SEQ ID NO: 105;

(15) an antibody (A1) comprising the heavy chain variable region of (1) and the light chain variable region of (8);

(16) an antibody (A6) comprising the heavy chain variable region of (2) and the light chain variable region of (9);

(17) an antibody (A10) comprising the heavy chain variable region of (3) and the light chain variable region of (10);

(18) an antibody (B5) comprising the heavy chain variable region of (4) and the light chain variable region of (11);

(19) an antibody (B6) comprising the heavy chain variable region of (5) and the light chain variable region of (12);

(20) an antibody (C8) comprising the heavy chain variable region of (6) and the light chain variable region of (13);

(21) an antibody (C10) comprising the heavy chain variable region of (7) and the light chain variable region of (14);

(22) a variant of the antibody of any one of (1) to (21) in which one or more amino acids have been substituted, deleted, added and/or inserted while retaining comparable activity to the antibody of any one of (1) to (21);

(23) an antibody that binds to the same epitope of an HS6ST2 protein as the antibody of any one of (1) to (21) binds to.

[7] The antibody of any one of [1]-[5] characterized in that it recognizes a stretch of amino acids 379-459, a stretch of amino acids 308-393, or a stretch of amino acids 24-175 of an HS6ST2 protein having the amino acid sequence of SEQ ID NO: 107.

[8] A pharmaceutical composition comprising the antibody of any one of [1]-[7] as an active ingredient.

[9] The pharmaceutical composition of [8], which is an anticancer agent.

[10] A method for diagnosing cancer, comprising the steps of:

(a) providing a sample collected from a subject, and (b) detecting an HS6ST2 protein or HS6ST2 gene contained in the sample of (a).

[11] An HS6ST2 protein conjugated to a cytotoxic agent.

[12] A pharmaceutical composition comprising the HS6ST2 protein of [11] as an active ingredient

[13] The pharmaceutical composition of [12], which is an anticancer agent.

Advantageous Effects of Invention

We prepared anti-HS6ST2 antibodies, and sought methods for diagnosing and treating cancer using them. The anti-HS6ST2 antibodies of the present invention were found to kill cells expressing HS6ST2 on the plasma membrane by their antibody-dependent cellular cytotoxicity (ADCC) activity. Further, they inhibited proliferation of cells in the presence of secondary antibodies conjugated to toxins. This indicated that anti-HS6ST2 antibodies having ADCC activity and immunotoxins targeting HS6ST2 are useful for treating cancer. In addition, the resulting antibodies bound to both of two existing variants of HS6ST2 having different N-terminal amino acid lengths (UniProt Q96MM7-1, Q96MM7-2).

Then, the expression of HS6ST2 proteins in cancer cells was evaluated using the anti-HS6ST2 antibodies. Flow cytometric analysis showed that lung cancer cell line and liver cancer cell line express HS6ST2 on the plasma membrane. Western blot analysis showed that lung cancer cell line and ovarian cancer cell line express HS6ST2. These HS6ST2 proteins seemed to be a variant lacking N-terminal 146 amino acids (UniProt Q96MM7-2) as determined from their molecular weights. Analysis by immunohistochemical staining showed that HS6ST2 is expressed on the plasma membrane in clinical lung adenocarcinoma and clinical squamous cell lung carcinoma. Further, Western blot analysis showed that HS6ST2 is secreted in the culture supernatants in lung cancer cell lines and ovarian cancer cell line.

Then, anticancer therapies targeting soluble HS6ST2 were sought. First, soluble HS6ST2 was found to bind to heparan sulfate on the plasma membrane by flow cytometric analysis. When soluble HS6ST2 was then bound to lung cancer cell lines, the anti-HS6ST2 antibodies inhibited proliferation of the cells in the presence of secondary antibodies conjugated to toxins. Thus, immunotoxins targeting soluble HS6ST2 was shown to be useful for treating cancer. In addition, clinical lung cancer also expressed HSPGs (Glycosaminoglycans in human lung cancer. Cancer. 1981. 48:2016; Heparan sulfate proteoglycan expression in human lung-cancer cells. Int J. Cancer. 1997. 74:335; Heterogeneity of heparan sulfates in human lung. Am J Respir Cell Mol. Biol. 2004. 30:166), suggesting that secreted HS6ST2 binds to cancer cells.

Further, methods for diagnosing cancer using soluble HS6ST2 were sought. An ELISA system capable of detecting soluble HS6ST2 in the ng/mL range was established using the resulting anti-HS6ST2 antibodies. This ELISA system enabled measurement even in the presence of human serum, showing that it can be applied to diagnose cancer by measuring blood analytes.

BRIEF DESCRIPTION OF DRAWINGS

FIG. 5 is a diagram showing the results of flow cytometric analysis by which binding of the anti-HS6ST2 antibodies A6 and C8 to HS6ST2_N-short_ctV5_CHO and mHS6ST2_ctV5_CHO was evaluated. Closed circles represent HS6ST2_N-short_ctV5_CHO, while open circles represent mHS6ST2_ctV5_CHO.

FIG. 9 is a diagram showing the results of flow cytometric analysis by which binding of the anti-HS6ST2 antibody B6 to the liver cancer cell line HuH6 and the lung adenocarcinoma cell line ABC-1 was evaluated. Black solid lines represent the anti-HS6ST2 antibody B6, while gray solid lines represent mIgG1.

FIG. 11 is a diagram showing the results of Western blotting of cancer cell lines using the anti-HS6ST2 antibody C10. The whole cell lysates (A) or 50-fold concentrated culture supernatants (B) of the lung adenocarcinoma cell lines A549, ABC-1, NCI-H441, NCI-H1781, and ovarian cancer cell line OVMANA were used as samples to compare the results in the presence and absence of N-Glycosidase F treatment.

FIG. 14 is a diagram showing binding of sHS6ST2_FLAG to the cancer cell line A549 and antitumor activity of the anti-HS6ST2 antibody C8 in the presence of Mab-ZAP. (A) shows the results of flow cytometric analysis using the anti-HS6ST2 antibody C8 after A549 cells were reacted with 100 μg/mL (bold line), 20 μg/mL (black solid line), 4 μg/mL (dotted line), 0.8 μg/mL (broken line), or 0 μg/mL (gray solid line) of sHS6ST2_FLAG. (B) shows the results of evaluation of cytostatic activity of the anti-HS6ST2 antibody C8 using Mab-ZAP after A549 cells were cultured in the presence (solid line) or absence (broken line) of sHS6ST2_FLAG.

DESCRIPTION OF EMBODIMENTS

HS6ST2

Figure 1A:
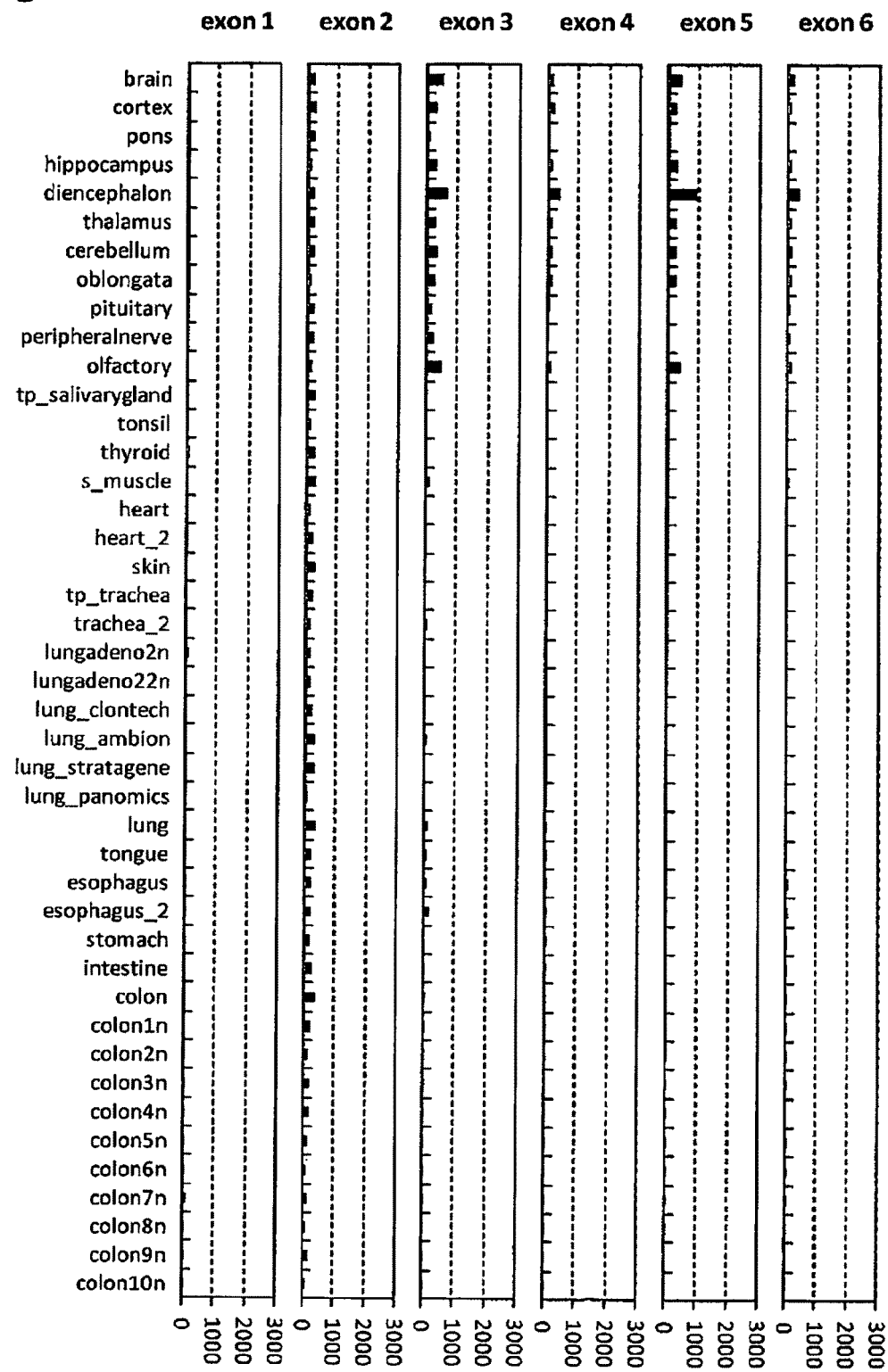
FIG. 1A is a diagram showing expression profiles of HS6ST2 in normal tissues.

The HS6ST2 protein used in the present invention is not specifically limited, and any HS6ST2 protein known to those skilled in the art can be used. The HS6ST2 protein is preferably human HS6ST2. The HS6ST2 used in the present invention may be any of existing variants of human HS6ST2. Examples of variants of HS6ST2 include a variant lacking exons 4 and 5 (GenBank Accession No: NM_147175, UniProt: Q96MM7-1, SEQ ID NO: 106), a variant lacking amino acids 1-146 of Q96MM7-1 (UniProt: Q96MM7-2, SEQ ID NO: 107), and a third variant (UniProt: Q96MM7-3, SEQ ID NO: 108).

HS6ST2 may be either an HS6ST2 protein expressed on the plasma membrane or secreted HS6ST2.

Anti-HS6ST2 Antibodies

Anti-HS6ST2 antibodies used in the present invention are not limited to any source, type, shape and the like so far as they bind to an HS6ST2 protein. Specifically, known antibodies such as non-human animal antibodies (e.g., mouse antibodies, rat antibodies, camel antibodies), human antibodies, chimeric antibodies, humanized antibodies can be used. In the present invention, monoclonal or polyclonal antibodies can be used, but preferably monoclonal antibodies. Binding of the antibodies to the HS6ST2 protein is preferably specific.

The HS6ST2 protein recognized by the anti-HS6ST2 antibodies of the present invention is not specifically limited, and may be an HS6ST2 protein expressed on the plasma membrane, or an HS6ST2 protein secreted from a cell, or an HS6ST2 conjugated to heparan sulfate, etc. Heparan sulfate is generally an N-sulfated or O-sulfated glycosaminoglycan composed of a repeating disaccharide unit with D-glucuronic acid and D-glucosamine. In the present invention, heparan sulfate is not specifically limited, but preferably heparan sulfate contained in heparan sulfate proteoglycan, especially heparan sulfate contained in heparan sulfate proteoglycan on the plasma membrane of cancer cells.

In the present invention, therefore, a preferred embodiment of an antibody that binds to an HS6ST2 protein conjugated to heparan sulfate is an antibody that binds to an HS6ST2 protein conjugated to heparan sulfate on the plasma membrane of cancer cells.

Anti-HS6ST2 antibodies used in the present invention can be obtained as polyclonal or monoclonal antibodies by using known means. Anti-HS6ST2 antibodies used in the present invention are preferably monoclonal antibodies especially derived from mammals. Monoclonal antibodies derived from mammals include those produced by hybridomas, and those produced by hosts transformed with an expression vector containing an antibody gene by genetic engineering techniques, etc.

Monoclonal antibody-producing hybridomas can be principally prepared using known techniques as follows. First, the HS6ST2 protein is used as a sensitizing antigen to immunize an animal according to a conventional immunization method. Immune cells obtained from the immunized animal are fused to known parent cells by a conventional cell fusion method to give hybridomas. These hybridomas can be screened for cells producing a desired antibody by a conventional screening method to select anti-HS6ST2 antibody-producing hybridomas.

Specifically, the preparation of a monoclonal antibody is performed as shown below, for example. First, the HS6ST2 protein used as a sensitizing antigen for preparing the antibody can be obtained by expressing the HS6ST2 gene. More specifically, a gene sequence encoding HS6ST2 is inserted into a known expression vector and transformed into a suitable host cell, after which the desired human HS6ST2 protein can be purified from the host cell or culture supernatant by a known method. A purified native HS6ST2 protein can also be used. A fusion protein containing a desired partial polypeptide of the HS6ST2 protein fused to another polypeptide can also be used as an immunogen. To prepare a fusion protein for use as an immunogen, an Fc fragment of an antibody, a peptide tag or the like can be used, for example. A vector expressing a fusion protein can be prepared by fusing genes encoding two or more desired polypeptide fragments in-frame and inserting the fused genes into an expression vector. Methods for preparing fusion proteins are described in Molecular Cloning 2nd ed. (Sambrook, J et al., Molecular Cloning 2nd ed., 9.47-9.58, Cold Spring Harbor Lab. press, 1989).

The HS6ST2 protein thus purified can be used as a sensitizing antigen to immunize a mammal. A partial peptide of HS6ST2 can also be used as a sensitizing antigen. For example, the following peptides can be used as sensitizing antigens.

A peptide obtained by chemical synthesis based on the amino acid sequence of human HS6ST2.

A peptide obtained by expressing a part of the HS6ST2 gene inserted in an expression vector.

A peptide obtained by degrading an HS6ST2 protein by a protease.

The region and size of HS6ST2 used as a partial peptide are not limited. The number of amino acids making up a peptide used as a sensitizing antigen is preferably at least 3 or more, e.g., 5 or more, or 6 or more. More specifically, a peptide of 8-50 residues, preferably 10-30 residues, can be used as a sensitizing antigen.

The mammal immunized with the sensitizing antigen is not specifically limited. To obtain a monoclonal antibody by cell fusion, the animal to be immunized is preferably selected to be compatible with a parent cell used for cell fusion. Generally, rodents are preferred animals to be immunized. Specifically, mouse, rat, hamster or rabbit can be used as an animal to be immunized. Other animals such as monkey may also be immunized.

The animals above can be immunized with a sensitizing antigen by known methods. For example, a typical method can comprise immunizing a mammal by injecting a sensitizing antigen intraperitoneally or subcutaneously. Specifically, the sensitizing antigen is administered to the mammal several times every 4 to 21 days. The sensitizing antigen is used for immunization after it is diluted to a suitable dilution ratio with PBS (phosphate-buffered saline), physiological saline or the like. Further, the sensitizing antigen may be administered with an adjuvant. For example, the sensitizing antigen can be used as an emulsion in Freund's complete adjuvant. In addition, a suitable carrier may be used for immunization with the sensitizing antigen. Especially when a low molecular weight partial peptide is used as a sensitizing antigen, the sensitizing antigen peptide is desirably used for immunization as a conjugate to a carrier protein such as albumin or keyhole limpet hemocyanin.

Alternatively, monoclonal antibodies can be obtained by DNA immunization. DNA immunization refers to an immunostimulation method comprising administering a vector DNA constructed to express a gene encoding an antigen protein in an animal to be immunized to the animal so that the immunizing antigen is in vivo expressed in the immunized animal. When compared with conventional immunization methods involving administering a protein antigen, DNA immunization can be expected to provide the following advantages.

Immunostimulation can be provided while maintaining the structure of membrane proteins such as HS6ST2.

The immunizing antigen need not be purified.

To obtain a monoclonal antibody of the present invention by DNA immunization, a DNA expressing an HS6ST2 protein is administered to an animal to be immunized first. The DNA encoding HS6ST2 can be synthesized by known methods such as PCR. The resulting DNA is inserted into a suitable expression vector and administered to an animal to be immunized. Expression vectors that can be used include, for example, commercially available expression vectors such as pcDNA3.1. Conventional methods can also be used to administer the vector to the animal. For example, DNA immunization can be performed by injecting gold particles coated with an expression vector into cells using a gene gun.

After a mammal is immunized as described above and an increase of the level of a desired antibody in serum is observed, immune cells are collected from the mammal and used for cell fusion. Especially, spleen cells can be preferably used as immune cells.

Mammalian myeloma cells are used as cells to be fused with the immune cells. Myeloma cells preferably contain a suitable selectable marker for screening. Selectable marker refers to a trait suitable for survival (or not) under specific culture conditions. Selectable markers such as hypoxanthine-guanine-phosphoribosyl transferase deficiency (hereinafter abbreviated as HGPRT deficiency), or thymidine kinase deficiency (hereinafter abbreviated as TK deficiency) are known. HGPRT- or TK-deficient cells are sensitive to hypoxanthine-aminopterin-thymidine (hereinafter abbreviated as HAT-sensitive). HAT-sensitive cells fail to synthesize DNA and die in HAT selective media, but once they are fused with normal cells, they grow even in HAT selective media because they can continue to synthesize DNA via the salvage pathway of normal cells.

HGPRT-deficient or TK-deficient cells can be selected in media containing 6-thioguanine or 8-azaguanine (hereinafter abbreviated as 8AG) or 5'-bromodeoxyuridine, respectively. Normal cells die because they take up these pyrimidine analogs in DNA, but cells deficient in these enzymes cannot take up these pyrimidine analogs so that they can survive in selective media. In addition, a selectable marker known as G418 resistance confers resistance to 2-deoxystreptamine antibiotics (gentamycin analogs) by the neomycin resistance gene. Various myeloma cells suitable for cell fusion are known. For example, the following myeloma cells can be used for the preparation of monoclonal antibodies in the present invention:

P3 (P3x63Ag8.653) (J. Immunol. (1979) 123, 1548-1550)
P3x63Ag8U.1 (Current Topics in Microbiology and Immunology (1978) 81, 1-7)
NS-1 (Kohler. G. and Milstein, C. Eur. J. Immunol. (1976) 6, 511-519)
MPC-11 (Margulies. D. H. et al., Cell (1976) 8, 405-415)
SP2/0 (Shulman, M. et al., Nature (1978) 276, 269-270)
FO (de St. Groth, S. F. et al., J. Immunol. Methods (1980) 35, 1-21)

S194 (Trowbridge, I. S. J. Exp. Med. (1978) 148, 313-323)
R210 (Galfre, G. et al., Nature (1979) 277, 131-133), etc.

Principally, cell fusion of immune cells with myeloma cells takes place according to known methods such as the method of Kohler and Milstein, et al. (Kohler. G. and Milstein, C., Methods Enzymol. (1981) 73, 3-46), for example.

More specifically, cell fusion can be performed in a conventional nutrient medium in the presence of a cell fusion promoter, for example. Fusion promoters that can be used include, for example, polyethylene glycol (PEG), Sendai virus (HVJ), etc. If desired, additives such as dimethyl sulfoxide can be included to further increase fusion efficiency.

Immune cells and myeloma cells can be used in any ratio. For example, immune cells are preferably used in a ratio of 1-10 to myeloma cells. Media that can be used for cell fusion include, for example, those suitable for the growth of myeloma cell lines such as RPMI1640 medium and MEM medium, and other conventional media used for such cell culture. The media can further contain serum supplements such as fetal calf serum (FCS).

Cell fusion is performed by thoroughly mixing predetermined amounts of immune cells and myeloma cells in a medium and adding a PEG solution preliminarily warmed at around 37° C. to form desired fused cells (hybridomas). In cell fusion, PEG having a mean molecular weight of about 1000-6000 can be added at a concentration of 30-60% (w/v), for example. Subsequently, cell fusion agents undesirable for the growth of hybridomas are removed by repeating sequential addition of any one of the suitable media above and centrifugation to remove the supernatant.

The hybridomas thus obtained can be selected in a selective medium depending on the selectable marker contained in the myeloma cells used for cell fusion. For example, HGPRT- or TK-deficient cells can be selected by cultivation in HAT medium (a medium containing hypoxanthine, aminopterin and thymidine). Thus, when HAT-sensitive myeloma cells are used for cell fusion, cells successfully fused with normal cells can be selectively grown in HAT medium. Cultivation in the above HAT medium is continued for a sufficient time for cells other than desired hybridomas (unfused cells) to die. Specifically, desired hybridomas can be typically selected by cultivation for several days to several weeks. Then, hybridomas producing a desired antibody can be screened and monocloned by conventional limiting dilution. Alternatively, antibodies recognizing HS6ST2 can be prepared by the method described in International Publication WO03/104453.

Screening and monocloning of the desired antibody can be conveniently performed by known screening methods based on antigen-antibody reaction. For example, an antigen is immobilized on a carrier such as beads of polystyrene or the like or a commercially available 96-well microtiter plate, and reacted with the culture supernatant of hybridomas. Then, the carrier is washed and then reacted with an enzyme-labeled secondary antibody or the like. If a desired antibody reactive to the sensitizing antigen is contained in the culture supernatant, the secondary antibody binds to the carrier via this antibody. Finally, whether or not the desired antibody exists in the culture supernatant can be determined by detecting the secondary antibody that binds to the carrier. Hybridomas producing the desired antibody having the ability to bind to the antigen can be cloned by limiting dilution or the like. Here, a substantially homogeneous HS6ST2 protein such as the protein used for immunization can be used as an antigen. For example, an HS6ST2-expressing cell line, soluble HS6ST2 or the like can be used as an antigen.

Alternatively, a desired antibody can be obtained by sensitizing human lymphocytes with an antigen instead of the above method for obtaining hybridomas by immunizing a non-human animal with an antigen. Specifically, human lymphocytes are sensitized with an HS6ST2 protein in vitro first. Then, the sensitized lymphocytes are fused with a suitable fusion partner. Permanently deviding human-derived myeloma cells can be used as fusion partner, for example (see JPB Hei-1-59878). Anti-HS6ST2 antibodies obtained by this method are human antibodies having binding activity to the HS6ST2 protein.

Alternatively, human anti-HS6ST2 antibodies can be obtained by administering an HS6ST2 protein as an antigen to a transgenic animal having all repertoires of a human antibody gene or immunizing an animal with a DNA constructed to express HS6ST2 in the animal. Antibody-producing cells of the immunized animal can be immortalized by such a process as cell fusion with a suitable fusion partner or infection with Epstein-Barr virus. Human antibodies against the HS6ST2 protein can be isolated from the immortalized cells obtained in this manner (see International Publications WO 94/25585, WO 93/12227, WO 92/03918, WO 94/02602). Moreover, cells producing an antibody having desired reaction specificity can be cloned by cloning the immortalized cells. When a transgenic animal is immunized, the immune system of the animal recognizes human HS6ST2 as foreign. Therefore, human antibodies against human HS6ST2 can be readily obtained.

Monoclonal antibody-producing hybridomas prepared in this manner can be subcloned in a conventional medium. Further, the hybridomas can be stored in liquid nitrogen for a long period.

A desired monoclonal antibody can be obtained from the culture supernatant of the hybridomas cultured by a conventional method. Alternatively, the monoclonal antibody can be obtained from ascites of a mammal compatible with the hybridomas by administering the hybridomas to it and growing them in it. The former method is suitable for obtaining high purity antibodies.

In the present invention, an antibody encoded by an antibody gene cloned from an antibody-producing cell can also be used. The cloned antibody gene can be expressed as an antibody by transfecting a host with a suitable vector containing it. Methods for isolating antibody genes, inserting them into vectors, and transforming host cells with them have already been established (e.g., see Vandamme, A. M. et al., Eur. J. Biochem. (1990) 192, 767-775).

For example, a cDNA encoding a variable region of an anti-HS6ST2 antibody can be obtained from a hybridoma cell producing the anti-HS6ST2 antibody. For this purpose, total RNA is typically isolated from the hybridoma first. The following methods can be used to isolate mRNA from a cell, for example.

Guanidine-ultracentrifugation (Chirgwin, J. M. et al., Biochemistry (1979) 18, 5294-5299)

AGPC method (Chomczynski, P. et al., Anal. Biochem. (1987) 162, 156-159).

The isolated mRNA can be purified using mRNA Purification Kit (from GE Healthcare Bio-Sciences) or the like. Alternatively, kits for directly isolating total mRNA from cells such as QuickPrep mRNA Purification Kit (from GE Healthcare Bio-Sciences) are also commercially available. Total mRNA can also be obtained from hybridomas using such kits. A cDNA encoding the antibody variable region can be synthesized from the resulting mRNA using a reverse transcriptase. Here, random sequences of 15-30 nucleotides selected from sequences common to the antibody gene can be used as primers. cDNA can be synthesized using AMV Reverse Transcriptase First-strand cDNA Synthesis Kit (from Seikagaku Corporation), or the like. To synthesize and amplify cDNA, 5'-Ampli FINDER RACE Kit (from Clontech) and 5'-RACE PCR (Frohman, M. A. et al., Proc. Natl. Acad. Sci. USA (1988) 85, 8998-9002, Belyaysky, A. et al., Nucleic Acids Res. (1989) 17, 2919-2932) can be used. Moreover, suitable restriction sites as described below can be introduced at both ends of cDNA during such cDNA synthesis.

A desired cDNA fragment is purified from the resulting PCR product and then ligated to a vector DNA. A recombinant vector is prepared in this manner and transfected into *E. coli* or the like to select a colony, after which a desired recombinant vector can be prepared from *E. coli* that formed the colony. Finally, the nucleotide sequence of the cDNA can be determined by known methods such as dideoxynucleotide chain termination, for example.

To obtain a gene encoding a variable region of an antibody, a cDNA library can also be used. First, cDNA is synthesized using mRNA isolated from an antibody-producing cell as a template to construct a cDNA library. For the synthesis of the cDNA library, a commercially available kit is conveniently used. In fact, isolation yield will be low if very small amounts of mRNA obtained from only a limited number of cells are directly purified. Therefore, mRNA is typically purified after it is combined with carrier RNA known to lack the antibody gene. Alternatively, RNA can be efficiently isolated from antibody-producing cells alone if a reasonable amount of RNA can be isolated. For example, addition of carrier RNA may not be required to isolate RNA from 10 or more, or 30 or more, preferably 50 or more antibody-producing cells.

The antibody gene is amplified by PCR using the resulting cDNA library as a template. Primers for amplifying antibody genes by PCR are known. For example, primers for amplifying a human antibody gene can be designed according to the disclosure of a paper (J. Mol. Biol. (1991) 222, 581-597) or the like. These primers have different nucleotide sequences for different immunoglobulin subclasses. Therefore, all possibilities should be contemplated to perform PCR when a cDNA library of unknown subclass is used as a template.

Specifically, primers capable of amplifying genes encoding γ1-γ5 heavy chains and kappa and lambda light chains can be used when a gene encoding human IgG is to be obtained, for example. To amplify the genes for the variable regions of IgG, a primer annealing to a segment corresponding to the hinge region is typically used as a 3' primer. On the other hand, a primer depending on the subclass can be used as a 5' primer.

The PCR products amplified with primers for amplifying the genes for various subclasses of the heavy and light chains provide independent libraries. The libraries thus synthesized can be used to reconstitute an immunoglobulin made of a combination of heavy and light chains. A desired antibody can be screened on the basis of the binding activity of the reconstituted immunoglobulin to HS6ST2.

To prepare an anti-HS6ST2 antibody from the resulting gene, the antibody gene can be inserted into an expression vector so that it is expressed under control of expression regulatory elements. The expression regulatory elements for expressing the antibody include, for example, enhancers and promoters. Then, a suitable host cell can be transformed with this expression vector to give a recombinant cell expressing a DNA encoding the anti-HS6ST2 antibody.

To express the antibody gene, DNAs encoding the heavy and light chains of the antibody can be inserted into different expression vectors. The vectors containing the heavy and light chains can be co-transfected into the same host cell to express an antibody molecule containing the heavy and light chains. Alternatively, the host cell can be transformed with a single expression vector containing DNAs encoding the heavy and light chains (see International Publication WO 94/11523).

A number of host-expression vector combinations for transfecting an isolated antibody into a suitable host to prepare an antibody are known. Any of these expression systems can be applied to the present invention. Eukaryotic host cells such as animal cells, plant cells, or fungal cells can be used. Specifically, the following animal cells can be used in the present invention.

(1) Mammalian cells: CHO, COS, myeloma, BHK (baby hamster kidney), Hela, Vero, HEK293, Ba/F3, HL-60, Jurkat, SK-HEP1, etc.

(2) Amphibian cells: *Xenopus oocyte*, etc.

(3) Insect cells: sf9, sf21, Tn5, etc.

Alternatively, antibody gene expression systems using plant cells derived from *Nicotiana* such as *Nicotiana tabacum* are known. For transformation of plant cells, callus culture cells can be used.

Further, the following fungal cells can be used. Yeasts include *Saccharomyces* such as *Saccharomyces serevisiae*, *Pichia* such as methylotrophic yeast (*Pichia pastoris*). Filamentous fungi include *Aspergillus* such as *Aspergillus niger*.

Alternatively, antibody gene expression systems using prokaryotic cells are also known. For example, bacterial cells such as *E. coli, Bacillus subtilis* can be used in the present invention.

When a mammalian cell is used, a conventional useful promoter, an antibody gene to be expressed and a 3' poly(A) signal can be operably linked to express the gene of interest. For example, promoters/enhancers include human cytomegalovirus immediate early promoter/enhancer.

In addition, viral promoters/enhancers, or mammalian cell-derived promoters/enhancers such as human elongation factor 1α (HEF1α) can be used for antibody expression. Viruses from which promoters/enhancers can be derived specifically include retrovirus, polyomavirus, adenovirus, simian virus 40 (SV40), etc.

The SV40 promoter/enhancer can be used according to the method of Mulligan et al. (Nature (1979) 277, 108). The HEF1α promoter/enhancer can be readily used for the expression of a desired gene according to the method of Mizushima et al. (Nucleic Acids Res. (1990) 18, 5322).

In *E. coli*, a conventional useful promoter, a signal sequence for antibody secretion and an antibody gene to be expressed can be operably linked to express the gene of interest. Promoters include, for example, lacZ promoter and araB promoter. When the lacZ promoter is used, the method of Ward et al. (Nature (1989) 341, 544-546; FASEBJ. (1992) 6, 2422-2427) can be employed. Alternatively, the araB promoter can be used for the expression of a desired gene according to the method of Better et al. (Science (1988) 240, 1041-1043).

When an antibody is to be produced in the periplasm of *E. coli*, the pelB signal sequence can be used as a signal sequences for antibody secretion (Lei, S. P. et al., J. Bacteriol. (1987) 169, 4379). After the antibody produced in the periplasm is isolated, the structure of the antibody is refolded to have desired binding activity by using a protein denaturant such as urea or guanidine hydrochloride.

When an antibody is to be produced in an animal cell, a signal sequence of a heavy chain gene or light chain gene of the antibody is desirably used as a signal sequence required for extracellular excretion. Alternatively, signal sequences contained in secreted proteins such as IL-3 or IL-6 can be used.

The origin of replication inserted into an expression vector may be derived from SV40, polyoma virus, adenovirus, bovine papilloma virus (BPV), etc. Moreover, a selectable marker can be inserted into the expression vector to amplify the gene copy number in the host cell system. Specifically, the following selectable markers can be used:

aminoglycoside transferase (APH) gene thymidine kinase (TK) gene

*Escherichia coli* xanthine guanine-phosphoribosyltransferase (Ecogpt) gene dihydrofolate reductase (dhfr) gene, etc.

These expression vectors are transfected into host cells, and then, transformed host cells are cultured in vitro or in vivo to produce a desired antibody. The host cells are cultured by known methods. For example, culture media such as DMEM, MEM, RPMI1640, IMDM can be used optionally in combination with serum supplements such as fetal calf serum (FCS).

The antibody expressed/produced as described above can be purified by using known methods conventionally used for protein purification alone or in combination as appropriate. For example, the antibody can be isolated/purified by appropriately selecting and combining affinity columns such as protein A columns, chromatography columns, filters, ultrafiltration, salting out, dialysis, etc. (Antibodies A Laboratory Manual. Ed Harlow, David Lane, Cold Spring Harbor Laboratory, 1988).

To produce recombinant antibodies, transgenic animals can also be used in addition to the host cells mentioned above. Thus, a desired antibody can be obtained from an animal transformed with a gene encoding the antibody. For example, an antibody gene can be constructed as a fused cell by inserting it in-frame into a gene encoding a protein endogenously produced in milk. Proteins secreted in milk that can be used include, for example, goat β casein, etc. A goat embryo is transfected with a DNA fragment containing the fused gene bearing the antibody gene, and the transfected embryo is implanted into a female goat. The desired antibody can be harvested as a fusion protein with a milk protein from milk produced by a transgenic goat (or offspring thereof) born from the goat implanted with the embryo. If desired, a hormone can be supplied to the transgenic goat to increase the amount of milk containing the desired antibody produced by the transgenic goat (Ebert, K. M. et al., Bio/Technology (1994) 12, 699-702).

Constant regions derived from human antibodies or constant regions derived from non-human animal antibodies can be used as constant regions of the recombinant antibodies of the present invention. For example, mouse antibody heavy chain constant regions such as Cγ1, Cγ2a, Cγ2b, Cγ3, Cμ, Cδ, Cα1, Cα2, Cε and light chain constant regions such as Cκ, Cλ can be used. Moreover, antibodies of animals other than mouse such as rat, rabbit, goat, sheep, camel, monkey can be used. These sequences are known. In addition, the constant regions can be modified to improve stability of the antibodies or production thereof.

When the antibodies are administered to human in the present invention, they can be recombinant antibodies artificially modified to reduce heterologous antigenicity to human or other purposes. Recombinant antibodies include, for example, chimeric antibodies, humanized antibodies, etc. These modified antibodies can be prepared by known methods.

Chimeric antibody refers to an antibody combining a variable region and a constant region of different sources. For example, an antibody containing heavy and light chain variable regions of a mouse antibody and heavy and light chain constant regions of a human antibody is a mouse-human hybrid chimeric antibody. A DNA encoding a variable region of a mouse antibody and a DNA encoding a constant region of a human antibody can be combined and inserted into an expression vector to prepare a recombinant vector expressing a chimeric antibody. A recombinant cell transformed with the vector is cultured and the inserted DNA is expressed, whereby the chimeric antibody produced in the culture can be harvested. The constant regions used in chimeric antibodies and humanized antibodies are derived from human antibodies.

For example, Cγ1, Cγ2, Cγ3, Cγ4, Cμ, Cδ, Cα1, Cα2 and Cε can be used as constant regions in the heavy chain. In the light chain, Cκ and Cλ can be used as constant regions. The amino acid sequences of these constant regions and the nucleotide sequences encoding them are known. Moreover, human antibody constant regions can be modified to improve stability of the antibodies or production thereof.

Generally, chimeric antibodies are composed of a variable region of an antibody derived from a non-human animal and a constant region derived from a human antibody. On the other hand, humanized antibodies are composed of a complementarity determining region (CDR) of an antibody derived from a non-human animal and a framework region (FR) derived from a human antibody and a constant region derived from the human antibody. Humanized antibodies are useful as active ingredients in therapeutic agents of the present invention because of the low antigenicity in human.

The variable regions of antibodies are composed of three CDRs interspersed between four FRs. The CDRs are regions substantially determining binding specificity of the antibodies. The amino acid sequences of the CDRs are highly variable. On the other hand, the amino acid sequences of the FRs often show high homology even between antibodies having different binding specifities. Therefore, it is generally known that binding specificity of an antibody can be transferred to another antibody by CDR grafting.

Humanized antibodies are also known as reshaped human antibodies. Specifically, humanized antibodies containing CDRs of an antibody of a non-human animal such as mouse grafted to a human antibody and the like are known. Typical genetic engineering techniques for obtaining humanized antibodies are also known.

Specifically, one known method for grafting CDRs of a mouse antibody to human FRs is Overlap Extension PCR, for example. In Overlap Extension PCR, nucleotide sequences encoding CDRs of a mouse antibody to be grafted are added to primers for synthesizing FRs of a human antibody. Primers are prepared for each of four FRs. Generally, it is known that when mouse CDRs are to be grafted to human FRs, the human FRs are advantageously chosen to have high homology with mouse FRs in order to retain the function of the CDRs. Thus, it is generally preferable to use human FRs each consisting of an amino acid sequence having high homology with the amino acid sequence of an FR adjacent to a mouse CDR to be grafted.

The nucleotide sequences to be combined are designed to be connected in-frame. Human FRs are individually synthesized with their respective primers. The resulting products contain a DNA encoding a mouse CDR added to each FR. The nucleotide sequences encoding mouse CDRs of the products are designed to overlap each other. Then, the overlapping CDRs of the products synthesized from a human antibody gene as a template are annealed to each other, which leads to complementary strand synthesis. In this reaction, the human FRs are connected via the mouse CDR sequences.

The entire variable region gene finally comprising three CDRs and four FRs is amplified with primers annealing to its 5'- and 3'-ends and containing suitable restriction endonuclease recognition sequences. A vector for expressing a humanized antibody can be prepared by inserting the resulting DNA and a DNA encoding a human antibody constant region into an expression vector to fuse them in-frame. This vector is transfected into a host to establish a recombinant cell, and then the recombinant cell is cultured to express the DNA encoding a humanized antibody, whereby the humanized antibody is produced in the cell culture (see European Patent Publication EP 239400, International Publication WO 96/02576).

The binding activity of the humanized antibody prepared as described above to the antigen can be evaluated by a qualitative or quantitative assay to conveniently select human antibody FRs that can be connected via CDRs so that the CDRs form good antigen-binding sites. If desired, amino acid residues of FRs can be substituted so that CDRs of the reshaped human antibody may form suitable antigen-binding sites. For example, an amino acid sequence change can be introduced into FRs by applying the PCR method used for grafting mouse CDRs to human FRs. Specifically, a partial nucleotide sequence change can be introduced into primers annealing to FRs. FRs synthesized with such primers contain the nucleotide sequence change. The binding activity of the variant antibody containing the amino acid change to the antigen can be evaluated by the assay described above to select variant FR sequences having desired property (Sato, K. et al., Cancer Res, 1993, 53, 851-856).

The antibodies of the present invention include not only bivalent antibodies represented by IgG but also monovalent antibodies or polyvalent antibodies represented by IgM so far as they bind to an HS6ST2 protein. The polyvalent antibodies of the present invention include polyvalent antibodies having completely the same antigen-binding sites or polyvalent antibodies having partially or completely different antigen-binding sites. The antibodies of the present invention are not limited to whole antibody molecules, but may also include truncated antibodies or conjugates thereof so far as they bind to an HS6ST2 protein.

Truncated antibodies include antibody fragments lacking a part of whole antibodies (e.g., whole IgG, etc.). Partial deficiencies in antibody molecules are acceptable so far as they retain the ability to bind to an HS6ST2 antigen. Antibody fragments in the present invention preferably contain either one or both of a heavy chain variable region (VH) and a light chain variable region (VL). Moreover, antibody fragments in the present invention preferably contain a CDR. The number of CDRs contained in antibody fragments of the present invention is not specifically limited, but preferably at least 6 including heavy chain CDR1, CDR2, CDR3, and light chain CDR1, CDR2, CDR3.

The amino acid sequence of VH or VL can contain substitution, deletion, addition and/or insertion. Either VH or VL or a part of both can be deleted so far as the ability to bind to an HS6ST2 antigen is retained. Further, the variable region may be chimeric or humanized. Specific examples of antibody fragments include, for example, Fab, Fab', F(ab')2, Fv, etc. Specific examples of truncated antibodies include, for example, Fab, Fab', F(ab')2, Fv, scFv (single chain Fv), diabody, sc(Fv)2 (single chain (Fv)2), scFv-Fc, etc. Multimers (e.g., dimer, trimer, tetramer, polymer) of these antibodies are also included in the truncated antibodies of the present invention.

Fragments of an antibody can be obtained by enzymatically treating the antibody to generate antibody fragments. Known enzymes for generating antibody fragments include, for example, papain, pepsin or plasmin or the like. Alternatively, genes encoding these antibody fragments can be constructed and inserted into expression vectors and then expressed in suitable host cells (e.g., see Co, M. S. et al., J. Immunol. (1994) 152, 2968-2976, Better, M. & Horwitz, A. H. Methods in Enzymology (1989) 178, 476-496, Plueckthun, A. & Skerra, A. Methods in Enzymology (1989) 178, 476-496, Lamoyi, E., Methods in Enzymology (1989) 121, 652-663, Rousseaux, J. et al., Methods in Enzymology (1989) 121, 663-669, Bird, R. E. et al., TIBTECH (1991) 9, 132-137).

Digestive enzymes cleave antibodies at specific sites to give antibody fragments of specific structures as shown below, for example. Any part of antibodies can be deleted by applying genetic engineering techniques to such enzymatically derived antibody fragments.

Papain digestion: F(ab)2 or Fab
Pepsin digestion: F(ab')2 or Fab'

Therefore, truncated antibodies in the present invention can be antibody fragments lacking any region so far as they retain binding affinity for HS6ST2. Further, the antibodies desirably retain their effector activity especially for treating proliferative diseases such as cancer according to the present invention. Thus, preferred truncated antibodies in the present invention have both binding affinity for HS6ST2 and effector function. The effector function of the antibodies includes ADCC activity and CDC activity. Therapeutic antibodies in the present invention most preferably have either or both of ADCC activity and CDC activity as effector function.

Diabody refers to a bivalent antibody fragment constructed by gene fusion (Holliger P et al., Proc. Natl. Acad. Sci. USA 90: 6444-6448 (1993), EP404,097, WO93/11161, etc.). Diabodies are dimers composed of two polypeptide chains. Typically, polypeptide chains making up a dimer each contain VL and VH connected via a linker in the same chain. However, the linkers in diabodies are normally too short to connect VL and VH. Specifically, the linkers consist of about five amino acid residues, for example. Therefore, the VL and VH encoded on the same polypeptide chain cannot form a single-chain variable region fragment, but form a dimer with another single-chain variable region. As a result, diabodies have two antigen-binding sites.

scFv fragments are obtained by connecting a heavy chain variable region and a light chain variable region of an antibody. In scFvs, the heavy chain variable region and light chain variable region are connected via a linker, preferably a peptide linker (Huston, J. S. et al., Proc. Natl. Acad. Sci. U.S.A, 1988, 85, 5879-5883). The heavy chain variable region and light chain variable region in scFvs may be derived from any antibodies described herein. The peptide linker connecting the variable regions is not specifically limited. For example, any single-chain peptide composed of about 3-25 residues can be used as a linker. Specifically, the peptide linkers described below or the like can be used, for example.

The variable regions of both chains can be connected by the PCR method as described above, for example. To connect the variable regions by PCR, a DNA encoding a whole or desired partial amino acid sequence of the following DNAs is used as a template first:

a DNA sequence encoding the heavy chain or the heavy chain variable region of the antibody, and a DNA sequence encoding the light chain or the light chain variable region of the antibody.

DNAs encoding the heavy and light chain variable regions are each amplified by PCR using a pair of primers having sequences corresponding to the sequences of both ends of the DNAs to be amplified. Then, a DNA encoding a peptide linker segment is provided. The DNA encoding a peptide linker can also be synthesized by PCR. The primers used here contain at the 5' end a nucleotide sequence that can be connected to the amplified product of each variable region separately synthesized. Then, PCR is performed using a DNA combination of [heavy chain variable region DNA]-[peptide linker DNA]-[light chain variable region DNA] and primers for Assembly PCR.

The primers for assembly PCR consist of a pair of a primer annealing to the 5' end of the [heavy chain variable region DNA] and a primer annealing to the 3' end of the [light chain variable region DNA]. Thus, the primers for assembly PCR are a primer set capable of amplifying a DNA encoding the whole sequence of an scFv to be synthesized. On the other hand, the [peptide linker DNA] contains a nucleotide sequence that can be connected to each variable region DNA. As a result, these DNAs are connected and finally the whole scFv is generated as an amplified product with the primers for assembly PCR. Once the DNA encoding the scFv has been prepared, an expression vector containing it and a recombinant cell transformed with the expression vector can be obtained by a conventional method. Further, the scFv can be obtained by culturing the resulting recombinant cell to express the DNA encoding the scFv.

scFv-Fc is a truncated antibody obtained by fusing an scFv containing a heavy chain variable region and a light chain variable region of an antibody to an Fc region (Cellular & Molecular Immunology 2006; 3: 439-443). The scFv used in the scFv-Fc may be derived from any source, and an IgM-derived scFv can be used, for example. The source of Fc is not specifically limited, and human IgG (human IgG1, etc.) can be used, for example. Thus, an exemplary preferred embodiment of scFv-Fc is an scFv-Fc in which an scFv fragment of an IgM antibody and CH2 (e.g., Cγ2) and CH3 (e.g., Cγ3) of human IgG1 are connected via a hinge region (Hγ) of human IgG1.

sc(Fv)2 is a truncated antibody obtained by connecting two VHs and two VLs via a linker or the like to form a single chain (Hudson et al., J. Immunol. Methods 1999; 231: 177-189). sc(Fv)2 can be prepared by connecting scFvs via a linker, for example.

The antibodies are preferably characterized in that two VHs and two VLs are arranged in the order of VH, VL, VH, VL ([VH] linker [VL] linker [VH] linker [VL]) from the N-terminus of a single-chain polypeptide.

The order of two VHs and two VLs is not specifically limited to the arrangement above, and they may be arranged in any order. For example, the following arrangements are included:

[VL] linker [VH] linker [VH] linker [VL]
[VH] linker [VL] linker [VL] linker [VH]
[VH] linker [VH] linker [VL] linker [VL]
[VL] linker [VL] linker [VH] linker [VH]
[VL] linker [VH] linker [VL] linker [VH]

Any peptide linker that can be inserted by genetic engineering or a synthetic linker (e.g., see Protein Engineering, 9 (3), 299-305, 1996) can be used as a linker for connecting antibody variable regions. In the present invention, a peptide linker is preferred. The length of the peptide linker is not specifically limited, and can be appropriately selected for the intended purpose by those skilled in the art. Typically, the peptide linker consists of 1-100 amino acid residues, preferably 3-50 amino acids, more preferably 5-30 amino acids, most preferably 12-18 amino acids (e.g., 15 amino acids).

The peptide linker can be formed of any amino acid sequence so far as the ability of connect scFvs is not inhibited. For example, the following amino acid sequences can be used for peptide linkers.

```
Ser

Gly-Ser

Gly-Gly-Ser

Ser-Gly-Gly

Gly-Gly-Gly-Ser (SEQ ID NO: 109)

Ser-Gly-Gly-Gly (SEQ ID NO: 110)

Gly-Gly-Gly-Gly-Ser (SEQ ID NO: 111)

Ser-Gly-Gly-Gly-Gly (SEQ ID NO: 112)

Gly-Gly-Gly-Gly-Gly-Ser (SEQ ID NO: 113)

Ser-Gly-Gly-Gly-Gly-Gly (SEQ ID NO: 114)

Gly-Gly-Gly-Gly-Gly-Gly-Ser (SEQ ID NO: 115)

Ser-Gly-Gly-Gly-Gly-Gly-Gly (SEQ ID NO: 116)

(Gly-Gly-Gly-Gly-Ser (SEQ ID NO: 111))n (Ser-Gly-Gly-Gly-Gly (SEQ ID NO: 112))n
``` wherein n is an integer of 1 or more.

The amino acid sequence of the peptide linker can be appropriately selected for the intended purpose by those skilled in the art. For example, n defining the length of the peptide linker is typically 1-5, preferably 1-3, more preferably 1 or 2.

Therefore, an especially preferred embodiment of sc(Fv)2 in the present invention may be the following sc(Fv)2 fragment, for example.

[VH] peptide linker (15 amino acids) [VL] peptide linker (15 amino acids) [VH] peptide linker (15 amino acids) [VL].

Alternatively, the variable regions can be connected by using a chemical crosslinker. Crosslinkers conventionally used for crosslinking peptide compounds or the like can be applied in the present invention. For example, the following chemical crosslinkers are known. These crosslinkers are commercially available.

N-hydroxysuccinimide (NHS),
disuccinimidyl suberate (DSS),
bis(sulfosuccinimidyl)suberate (BS3),
dithiobis (succinimidyl propionate) (DSP),
dithiobis (sulfosuccinimidyl propionate) (DTSSP),
ethylene glycol bis(succinimidyl succinate) (EGS),
ethylene glycol bis(sulfosuccinimidyl succinate) (sulfo-EGS),
disuccinimidyl tartrate (DST),
disulfosuccinimidyl tartrate (sulfo-DST),
bis[2-(succinimidoxycarbonyloxy)ethyl]sulfone (BSOCOES), and
bis[2-(sulfo succinimidoxycarbonyloxy)ethyl]sulfone (sulfo-BSOCOES), etc.

To connect four antibody variable regions, three linkers are typically required. The linkers may be the same or different. In the present invention, a preferred truncated antibody is a diabody or sc(Fv)2. To obtain such truncated antibodies, an antibody can be treated with an enzyme such as e.g., papain or pepsin to generate antibody fragments, or DNAs encoding these antibody fragments can be constructed and inserted into an expression vector and then expressed in a suitable host cell (e.g., see Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; Bird, R. E. and Walker, B. W., Trends Biotechnol. (1991) 9, 132-137).

The antibodies of the present invention include not only monovalent antibodies but also polyvalent antibodies. The polyvalent antibodies of the present invention include polyvalent antibodies having completely the same antigen-binding sites or polyvalent antibodies having partially or completely different antigen-binding sites.

The antibodies conjugated to various molecules such as polyethylene glycol (PEG) can also be used. Further, the antibodies can also be conjugated to cytotoxic agents such as chemotherapeutic agents, toxic peptides or radioactive chemicals. Such antibody conjugates can be obtained by chemically modifying the antibody constructs. Methods for modifying antibodies have been established in the art.

Cytotoxic agents conjugated to the anti-HS6ST2 antibodies of the present invention to induce cytotoxic activity are specifically chemotherapeutic agents, including, for example, azaribine, anastrozole, azacytidine, bleomycin, bortezomib, bryostatin-1, busulfan, camptothecin, 10-hydroxycamptothecin, carmustine, celebrex, chlorambucil, cisplatin, irinotecan, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin, ethinyl estradiol, estramustine, etoposide, etoposide glucuronide, floxuridine, fludarabine, flutamide, fluorouracil, fluoxymesterone, gemcitabine, hydroxyprogesterone caproate, hydroxyurea, idarubicin, ifosfamide, leucovorin, lomustine, mechlorethamine, medroxyprogesterone acetate, megestrol acetate, melphalan, mercaptopurine, methotrexate, mitoxantrone, mithramycin, mitomycin, mitotane, phenylbutyrate, prednisone, procarbazine, paclitaxel, pentostatin, semustine, streptozocin, tamoxifen, taxanes, taxol, testosterone propionate, thalidomide, hioguanine, thiotepa, teniposide, topotecan, uracil mustard, vinblastine, vinorelbine, vincristine.

In the present invention, preferred chemotherapeutic agents are low molecular weight chemotherapeutic agents. Low molecular weight chemotherapeutic agents are less likely to interfere with the functions of antibodies even after they are conjugated to the antibodies. In the present invention, the low molecular weight chemotherapeutic agents typically have a molecular weight of 100-2000, preferably 200-1000. All of the chemotherapeutic agents listed here are low molecular weight chemotherapeutic agents. These chemotherapeutic agents in the present invention include prodrugs that are converted in vivo into active chemotherapeutic agents. Activation of the prodrugs may be enzymatic or non-enzymatic.

Further, the cytotoxic agents of the present invention may be toxic peptides, in which case antibodies are conjugated to toxic peptides. Examples of toxic peptides include, for example, Diphtheria toxin A Chain (Langone J. J., et al., Methods in Enzymology, 93, 307-308, 1983), *Pseudomonas* Exotoxin (Nature Medicine, 2, 350-353, 1996), Ricin A Chain (Fulton R. J., et al., J. Biol. Chem., 261, 5314-5319, 1986; Sivam G., et al., Cancer Res., 47, 3169-3173, 1987; Cumber A. J. et al., J. Immunol. Methods, 135, 15-24, 1990; Wawrzynczak E. J., et al., Cancer Res., 50, 7519-7562, 1990; Gheeite V., et al., J. Immunol. Methods, 142, 223-230, 1991); Deglicosylated Ricin A Chain (Thorpe P. E., et al., Cancer Res., 47, 5924-5931, 1987); Abrin A Chain (Wawrzynczak E. J., et al., Br. J. Cancer, 66, 361-366, 1992; Wawrzynczak E. J., et al., Cancer Res., 50, 7519-7562, 1990; Sivam G., et al., Cancer Res., 47, 3169-3173, 1987; Thorpe P. E., et al., Cancer Res., 47, 5924-5931, 1987); Gelonin (Sivam G., et al., Cancer Res., 47, 3169-3173, 1987; Cumber A. J., et al., J. Immunol. Methods, 135, 15-24, 1990; Wawrzynczak E. J., et al., Cancer Res., 50, 7519-7562, 1990; Bolognesi A., et al., Clin. exp. Immunol., 89, 341-346, 1992); Pokeweed anti-viral protein from seeds (PAP-s) (Bolognesi A., et al., Clin. exp. Immunol., 89, 341-346, 1992); Briodin (Bolognesi A., et al., Clin. exp. Immunol., 89, 341-346, 1992); Saporin (Bolognesi A., et al., Clin. exp. Immunol., 89, 341-346, 1992); Momordin (Cumber A. J., et al., J. Immunol. Methods, 135, 15-24, 1990; Wawrzynczak E. J., et al., Cancer Res., 50, 7519-7562, 1990; Bolognesi A., et al., Clin. exp. Immunol., 89, 341-346, 1992); Momorcochin (Bolognesi A., et al., Clin. exp. Immunol., 89, 341-346, 1992); Dianthin 32 (Bolognesi A., et al., Clin. exp. Immunol., 89, 341-346, 1992); Dianthin 30 (Stirpe F., Barbieri L., FEBS letter 195, 1-8, 1986); Modeccin (Stirpe F., Barbieri L., FEBS letter 195, 1-8, 1986); Viscumin (Stirpe F., Barbieri L., FEBS letter 195, 1-8, 1986); Volkesin (Stirpe F., Barbieri L., FEBS letter 195, 1-8, 1986); Dodecandrin (Stirpe F., Barbieri L., FEBS letter 195, 1-8, 1986); Tritin (Stirpe F., Barbieri L., FEBS letter 195, 1-8, 1986); Luffin (Stirpe F., Barbieri L., FEBS letter 195, 1-8, 1986); Trichokirin (Casellas P., et al., Eur. J. Biochem. 176, 581-588, 1988; Bolognesi A., et al., Clin. exp. Immunol., 89, 341-346, 1992).

In the present invention, the cytotoxic agents may be radioactive chemicals, which refer to chemicals containing radioactive isotopes. The radioactive isotopes are not specifically limited, and any radioactive isotopes can be used, such as $^{32}P$, $^{14}C$, $^{125}I$, $^{3}H$, $^{131}I$, $^{186}Re$, $^{188}Re$, etc., for example.

In another embodiment, one or more low molecular weight chemotherapeutic agents and toxic peptides can be used in combination to modify the antibodies. Conjugation of the anti-HS6ST2 antibodies to the low molecular weight chemotherapeutic agents can be covalent or non-covalent. Methods for preparing antibodies conjugated to these chemotherapeutic agents are known.

Moreover, protein drugs or toxins can be conjugated to the antibodies by genetic engineering techniques. Specifically, a DNA encoding one of the toxic peptides and a DNA encoding an anti-HS6ST2 antibody can be fused in-frame and inserted into an expression vector to construct a recombinant vector, for example. A suitable host cell is transformed with the vector and the resulting transformed cell is cultured to express the inserted DNA, whereby the anti-HS6ST2 antibody conjugated to the toxic peptide can be obtained as a fusion protein. When a fusion protein is to be formed between a protein drug or toxin and an antibody, the drug or toxin is typically fused to the C-terminus of the antibody. A peptide linker can be inserted between the antibody and the protein drug or toxin.

Further, the antibodies of the present invention may be bispecific antibodies. Bispecific antibody refers to an antibody having variable regions recognizing different epitopes in the same antibody molecule. In the present invention, bispecific antibodies may have antigen-binding sites recognizing different epitopes on an HS6ST2 molecule. In such bispecific antibodies, two antibody molecules can bind to one HS6ST2 molecule. Therefore, more potent cytotoxic effects can be expected.

Alternatively, bispecific antibodies recognizing HS6ST2 at one antigen-binding site and a cytotoxic agent at the other antigen-binding site can be used. Cytotoxic agents specifically include chemotherapeutic agents, toxic peptides or radioactive chemicals, etc. Such bispecific antibodies bind to cells that express HS6ST2 while capturing cytotoxic agents. Therefore, cytotoxic agents can directly act on HS6ST2-expressing cells. Thus, bispecific antibodies recognizing cytotoxic agents can specifically attack tumor cells to inhibit proliferation of the tumor cells.

In the present invention, bispecific antibodies that recognize an antigen other than HS6ST2 can also be combined. For example, bispecific antibodies that recognize an antigen other than HS6ST2 but specifically expressed on the surface of a target cancer cell similarly to HS6ST2 can be combined.

Methods for preparing bispecific antibodies are known. For example, a bispecific antibody can be prepared by linking two antibodies recognizing different antigens. The antibodies to be linked may be half molecules each having a heavy chain and a light chain or quarter molecules having a heavy chain alone. Alternatively, a fused cell producing a bispecific antibody can be prepared by fusing hybridomas producing different monoclonal antibodies. Further, bispecific antibodies can be prepared by genetic engineering techniques.

Known means can be used to assay antigen-binding activity of antibodies (Antibodies A Laboratory Manual. Ed Harlow, David Lane, Cold Spring Harbor Laboratory, 1988). For example, ELISA (enzyme-linked immunoabsorbent assay), EIA (enzyme immunoassay), RIA (radioimmunoassay) or fluorescent immunoassay, etc. can be used.

Alternatively, the antibodies of the present invention may be carbohydrate-modified antibodies. It is known that cytotoxic activity of antibodies can be enhanced by modifying carbohydrates of the antibodies. For example, the following carbohydrate-modified antibodies are known:

Glycosylation-modified antibodies (WO99/54342, etc.),
Non-fucosylated antibodies (WO00/61739, WO02/31140, etc.),
Antibodies containing carbohydrates bearing bisecting GlcNAc (WO02/79255, etc.), etc.

When the antibodies of the present invention are used for therapeutic purposes, the antibodies preferably have cytotoxic activity.

The cytotoxic activity in the present invention includes, for example, antibody-dependent cell-mediated cytotoxicity (ADCC) activity, complement-dependent cytotoxicity (CDC) activity, etc. As used herein, CDC activity refers to a cytotoxic activity mediated by the complement system. On the other hand, ADCC activity refers to the ability of Fcγ-receptor-bearing cells (immune cells or the like) to bind to the Fc region of a specific antibody via the Fcγ receptor and thereby attack a target cell when the antibody adheres to a cell surface antigen of the target cell.

Whether or not an anti-HS6ST2 antibody has ADCC activity or whether or not it has CDC activity can be determined by known methods (e.g., Current protocols in Immunology, Chapter 7. Immunologic studies in humans, Editor, John E, Coligan et al., John Wiley & Sons, Inc., (1993), etc.).

Specifically, the preparation of an effector cell, a complement solution and a target cell is performed first.

(1) Preparation of an Effector Cell

A spleen is removed from a CBA/N mouse or the like, and spleen cells are isolated in RPMI1640 medium (from Invitrogen). The cells are washed with the same medium containing 10% fetal bovine serum (FBS, from HyClone), and then prepared at a density of $5 \times 10^6$ cells/ml, whereby an effector cell can be prepared.

(2) Preparation of a Complement Solution

A complement solution can be prepared by diluting Baby Rabbit Complement (from CEDARLANE) to 1:10 in a medium containing 10% FBS (Invitrogen).

(3) Preparation of a Target Cell

Cells expressing an HS6ST2 protein can be incubated with 0.2 mCi of $^{51}$Cr-sodium chromate (from GE Healthcare BioScience Ltd.) in DMEM medium containing 10% FBS at 37° C. for 1 hour to radioactively label the target cells. Cells expressing an HS6ST2 protein that can be used include cells transformed with a gene encoding the HS6ST2 protein, lung adenocarcinoma cells, lung cancer cells, liver cancer cells, ovarian cancer cells, squamous cell lung carcinoma cells, etc. After radioactive labeling, the cells are washed three times with RPMI1640 medium containing 10% FBS and prepared at a density of $2 \times 10^5$ cells/ml, whereby the target cells can be prepared.

ADCC activity or CDC activity can be assayed by the method as follows. For assaying ADCC activity, 50 µl each of the target cell and an anti-HS6ST2 antibody are added to a 96-well U-bottom plate (from Becton Dickinson), and reacted on ice for 15 minutes. Then, 100 µl of the effector cell is added and incubated in a carbon dioxide incubator for 4 hours. The final concentration of the antibody is 0 or 10 µg/ml. After incubation, 100 µl of the supernatant is harvested, and assayed for radioactivity by a gamma counter (COBRAII AUTO-GAMMA, MODEL D5005, from Packard Instrument Company). Cytotoxic activity (%) can be calculated from the observed values according to the equation: $(A-C)/(B-C) \times 100$, wherein A represents radioactivity (cpm) in each sample, B represents radioactivity (cpm) in a sample containing 1% NP-40 (from Nacalai Tesque), and C represents radioactivity (cpm) in a sample containing the target cell alone.

For assaying CDC activity, 50 µl each of the target cell and an anti-HS6ST2 antibody are added to a 96-well flat-bottom plate (from Becton Dickinson), and reacted on ice for 15 minutes. Then, 100 µl of the complement solution is added and incubated in a carbon dioxide incubator for 4 hours. The final concentration of the antibody is 0 or 3 µg/ml. After incubation, 100 µl of the supernatant is harvested, and assayed for radioactivity by a gamma counter. Cytotoxic activity can be calculated in the same manner as described for the determination of ADCC activity.

For assaying cytotoxic activity of an antibody conjugate, 50 µl each of the target cell and the anti-HS6ST2 antibody conjugate are added to a 96-well flat-bottom plate (from Becton Dickinson), and reacted on ice for 15 minutes. The plate is incubated in a carbon dioxide incubator for 1-4 hours. The final concentration of the antibody is 0 or 3 µg/ml. After incubation, 100 µl of the supernatant is harvested, and assayed for radioactivity by a gamma counter. Cytotoxic activity can be calculated in the same manner as described for the determination of ADCC activity. Further, one of other embodiments of the antibodies used in the present invention is an antibody having internalization activity. As used herein, the term "antibody having internalization activity" refers to an antibody that is transported into cells (cytoplasms, vesicles, other organelles, etc.) when it binds to HS6ST2.

Whether or not an antibody has internalization activity can be assessed by methods known to those skilled in the art, for example, by contacting an anti-HS6ST2 antibody conjugated to a label with an HS6ST2-expressing cell to assess whether or not the label has been taken up into the cell; or contacting an anti-HS6ST2 antibody conjugated to a cytotoxic agent with an HS6ST2-expressing cell to assess whether or not apoptosis has been induced into the HS6ST2-expressing cell, etc. More specifically, whether or not an antibody has internalization activity can be assessed by the methods described in the Examples below and the like.

Antibodies having internalization activity can be used as pharmaceutical compositions such as anticancer agents by conjugating them to the cytotoxic agents listed above, for example.

Examples of HS6ST2-recognizing antibodies used in the present invention include, but not specifically limited, the following antibodies, for example.

(1) an antibody (A1) comprising a heavy chain variable region including a heavy chain CDR1 having the amino acid sequence of SEQ ID NO: 64, a heavy chain CDR2 having the amino acid sequence of SEQ ID NO: 65, and a heavy chain CDR3 having the amino acid sequence of SEQ ID NO: 66;

(2) an antibody (A6) comprising a heavy chain variable region including a heavy chain CDR1 having the amino acid sequence of SEQ ID NO: 70, a heavy chain CDR2 having the amino acid sequence of SEQ ID NO: 71, and a heavy chain CDR3 having the amino acid sequence of SEQ ID NO: 72;

(3) an antibody (A10) comprising a heavy chain variable region including a heavy chain CDR1 having the amino acid sequence of SEQ ID NO: 76, a heavy chain CDR2 having the amino acid sequence of SEQ ID NO: 77, and a heavy chain CDR3 having the amino acid sequence of SEQ ID NO: 78;

(4) an antibody (B5) comprising a heavy chain variable region including a heavy chain CDR1 having the amino acid sequence of SEQ ID NO: 82, a heavy chain CDR2 having the amino acid sequence of SEQ ID NO: 83, and a heavy chain CDR3 having the amino acid sequence of SEQ ID NO: 84;

(5) an antibody (B6) comprising a heavy chain variable region including a heavy chain CDR1 having the amino acid sequence of SEQ ID NO: 88, a heavy chain CDR2 having the amino acid sequence of SEQ ID NO: 89, and a heavy chain CDR3 having the amino acid sequence of SEQ ID NO: 90;

(6) an antibody (C8) comprising a heavy chain variable region including a heavy chain CDR1 having the amino acid sequence of SEQ ID NO: 94, a heavy chain CDR2 having the amino acid sequence of SEQ ID NO: 95, and a heavy chain CDR3 having the amino acid sequence of SEQ ID NO: 96;

(7) an antibody (C10) comprising a heavy chain variable region including a heavy chain CDR1 having the amino acid sequence of SEQ ID NO: 100, a heavy chain CDR2 having the amino acid sequence of SEQ ID NO: 101, and a heavy chain CDR3 having the amino acid sequence of SEQ ID NO: 102;

(8) an antibody (A1) comprising a light chain variable region including a light chain CDR1 having the amino acid sequence of SEQ ID NO: 67, a light chain CDR2 having the amino acid sequence of SEQ ID NO: 68, and a light chain CDR3 having the amino acid sequence of SEQ ID NO: 69;

(9) an antibody (A6) comprising a light chain variable region including a light chain CDR1 having the amino acid sequence of SEQ ID NO: 73, a light chain CDR2 having the amino acid sequence of SEQ ID NO: 74, and a light chain CDR3 having the amino acid sequence of SEQ ID NO: 75;

(10) an antibody (A10) comprising a light chain variable region including a light chain CDR1 having the amino acid sequence of SEQ ID NO: 79, a light chain CDR2 having the amino acid sequence of SEQ ID NO: 80, and a light chain CDR3 having the amino acid sequence of SEQ ID NO: 81;

(11) an antibody (B5) comprising a light chain variable region including a light chain CDR1 having the amino acid sequence of SEQ ID NO: 85, a light chain CDR2 having the amino acid sequence of SEQ ID NO: 86, and a light chain CDR3 having the amino acid sequence of SEQ ID NO: 87;

(12) an antibody (B6) comprising a light chain variable region including a light chain CDR1 having the amino acid sequence of SEQ ID NO: 91, a light chain CDR2 having the amino acid sequence of SEQ ID NO: 92, and a light chain CDR3 having the amino acid sequence of SEQ ID NO: 93;

(13) an antibody (C8) comprising a light chain variable region including a light chain CDR1 having the amino acid sequence of SEQ ID NO: 97, a light chain CDR2 having the amino acid sequence of SEQ ID NO: 98, and a light chain CDR3 having the amino acid sequence of SEQ ID NO: 99;

(14) an antibody (C10) comprising a light chain variable region including a light chain CDR1 having the amino acid sequence of SEQ ID NO: 103, a light chain CDR2 having the amino acid sequence of SEQ ID NO: 104, and a light chain CDR3 having the amino acid sequence of SEQ ID NO: 105;

(15) an antibody (A1) comprising the heavy chain variable region of (1) and the light chain variable region of (8);

(16) an antibody (A6) comprising the heavy chain variable region of (2) and the light chain variable region of (9);

(17) an antibody (A10) comprising the heavy chain variable region of (3) and the light chain variable region of (10);

(18) an antibody (B5) comprising the heavy chain variable region of (4) and the light chain variable region of (11);

(19) an antibody (B6) comprising the heavy chain variable region of (5) and the light chain variable region of (12);

(20) an antibody (C8) comprising the heavy chain variable region of (6) and the light chain variable region of (13);

(21) an antibody (C10) comprising the heavy chain variable region of (7) and the light chain variable region of (14);

(22) a variant of the antibody of any one of (1) to (21) in which one or more amino acids have been substituted, deleted, added and/or inserted while retaining comparable activity to the antibody of any one of (1) to (21);

(23) an antibody that binds to the same epitope of an HS6ST2 protein as the antibody of any one of (1) to (21) binds to.

As used herein, the expression "comparable activity to an antibody of the present invention" means comparable binding activity to HS6ST2 and/or cytotoxic activity to HS6ST2-expressing cells.

The introduction of a mutation into a polypeptide is one of methods well known to those skilled in the art for preparing a polypeptide functionally similar to another polypeptide. For example, those skilled in the art can prepare antibodies functionally similar to the antibodies of the present invention by appropriately introducing mutation into the antibodies using site-directed mutagenesis (Hashimoto-Gotoh, T. et al. (1995) Gene 152, 271-275, Zoller, M J, and Smith, M. (1983) Methods Enzymol. 100, 468-500, Kramer, W. et al. (1984) Nucleic Acids Res. 12, 9441-9456, Kramer W, and Fritz H J (1987) Methods. Enzymol. 154, 350-367, Kunkel, T A (1985) Proc Natl Acad Sci USA. 82, 488-492, Kunkel (1988) Methods Enzymol. 85, 2763-2766) or the like. Further, amino acid variations may also occur in nature. Thus, antibodies having an amino acid sequence containing one or more amino acid changes in the amino acid sequences of the antibodies of the present invention and functionally similar to the antibodies are also included in the antibodies of the present invention.

The number of amino acid changes in such variants is normally 50 amino acids or less, preferably 30 amino acids or less, more preferably 10 amino acids or less (e.g., 5 amino acids or less).

In each amino acid change, an amino acid residue is desirably changed to another amino acid residue in which the properties of amino acid side chains are conserved. For example, the following classification has been established according to the properties of amino acid side chains.

Hydrophobic amino acids (A, I, L, M, F, P, W, Y, V),
Hydrophilic amino acids (R, D, N, C, E, Q, G, H, K, S, T), Amino acids having aliphatic side chains (G, A, V, L, I, P),
Amino acids having hydroxyl-containing side chains (S, T, Y),
Amino acids having sulfur atom-containing side chains (C, M),
Amino acids having carboxylate- and amide-containing side chains (D, N, E, Q),
Amino acids having base-containing side chains (R, K, H),
Amino acids having aromatic-containing side chains (H, F, Y, W).
(Amino acids are shown by single-letter codes in the parentheses).

It has previously been known that a polypeptide having an amino acid sequence modified by deletion, addition and/or substitution of one or more amino acid residues as compared with a reference amino acid sequence retains its biological activity (Mark, D. F. et al., Proc. Natl. Acad. Sci. USA (1984) 81, 5662-5666, Zoller, M. J. and Smith, M., Nucleic Acids Research (1982) 10, 6487-6500, Wang, A. et al., Science 224, 1431-1433, Dalbadie-McFarland, G. et al., Proc. Natl. Acad. Sci. USA (1982) 79, 6409-6413). Thus, it is generally said that a polypeptide is more likely to retain activity when an amino acid in the amino acid sequence of the polypeptide is substituted for another amino acid within the same group. In the present invention, amino acid substitutions within the same group are referred to as conservative substitutions.

The present invention also provides antibodies that bind to the same epitope as the antibody of any one of (1)-(21) above binds to. Specific examples of the antibodies of (1)-(21) above include the antibodies A1, A6, A10, B5, B6, C8, and C10 described in the Examples herein below. Thus, the present invention also provides antibodies that recognize the same epitope as A1, A6, A10, B5, B6, C8 and C10 recognize. Such antibodies can be obtained by the method as follows, for example.

Whether or not a test antibody shares an epitope with a reference antibody can be assessed by competition between them for the same epitope. Competition between the antibodies is detected by a cross-blocking assay or the like. For example, competitive ELISA is a preferred cross-blocking assay.

Specifically, a cross-blocking assay comprises preincubating an HS6ST2 protein coated on wells of a microtiter plate in the presence or absence of a candidate competitive antibody, and then adding an anti-HS6ST2 antibody of the present invention. The amount of the anti-HS6ST2 antibody of the present invention bound to the HS6ST2 protein in the wells indirectly correlates to the binding potency of the candidate competitive antibody (test antibody) that competes for binding to the same epitope. Thus, as the affinity of the test antibody for the same epitope increases, the amount of the anti-HS6ST2 antibody of the present invention bound to the wells coated with the HS6ST2 protein decreases while the amount of the test antibody bound to the wells coated with the HS6ST2 protein increases.

The amounts of the antibodies bound to the wells can be readily determined by labeling the antibodies in advance. For example, a biotinylated antibody can be assayed by using an avidin-peroxidase conjugate and a suitable substrate. A cross-blocking assay using an enzyme label such as peroxidase is specifically called competitive ELISA. The antibodies can also be labeled with other detectable or measurable labels. Specifically, radioactive labels or fluorescent labels are known.

When the test antibody contains a constant region derived from a species different from the anti-HS6ST2 antibody of the present invention, either antibody bound to the wells can be assayed by a labeled antibody recognizing either constant region. Alternatively, when the antibodies are derived from the same species but belong to different classes, the antibodies bound to the wells can be assayed by an antibody recognizing each class.

If the candidate antibody can block at least 20%, preferably at least 30%, more preferably at least 50% of binding of the anti-HS6ST2 antibody as compared with the binding activity obtained in a control assay performed in the absence of the candidate competitive antibody, the candidate competitive antibody is an antibody that binds to substantially the same epitope as the anti-HS6ST2 antibody of the present invention binds to or an antibody that competes for binding to the same epitope.

For determining whether or not a test antibody binds to the same epitope as the anti-HS6ST2 antibody of the present invention binds to, a constant region of the anti-HS6ST2 antibody of the present invention may be replaced by the same constant region as the test antibody. When the test antibody has a human-derived constant region (human IgG1, IgG2, IgG3, IgG4, etc.), for example, a constant region of the anti-HS6ST2 antibody of the present invention can be replaced by the same constant region as the test antibody.

A1, A10, B5, B6, and C8 recognize a peptide consisting of amino acids 379-459 of an HS6ST2 protein having the amino acid sequence of SEQ ID NO: 107, whereby preferred examples of antibodies that recognize the same epitope as A1, A10, B5, B6, and C8 recognize include antibodies that recognize a stretch of amino acids 379-459 of an HS6ST2 protein having the amino acid sequence of SEQ ID NO: 107.

A6 recognizes a peptide consisting of amino acids 308-393 of an HS6ST2 protein having the amino acid sequence of SEQ ID NO: 107, whereby preferred examples of antibodies that recognize the same epitope as A6 recognizes include antibodies that recognize a stretch of amino acids 308-393 of an HS6ST2 protein having the amino acid sequence of SEQ ID NO: 107.

C10 recognizes a peptide consisting of amino acids 24-175 of an HS6ST2 protein having the amino acid sequence of SEQ ID NO: 107, whereby preferred examples of antibodies that recognize the same epitope as C10 recognizes include antibodies that recognize a stretch of amino acids 24-175 of an HS6ST2 protein having the amino acid sequence of SEQ ID NO: 107.

HS6ST2 Proteins Conjugated to Cytotoxic Agents the Present Invention Also Provides HS6ST2 Proteins Conjugated to Cytotoxic Agents. The HS6ST2 proteins conjugated to cytotoxic agents can be used for anticancer agents or the like because they seem to be internalized into cells after they bind to heparin sulfate.

The cytotoxic agents to be conjugated to HS6ST2 proteins are not specifically limited, and include, for example, the cytotoxic agents listed above. The HS6ST2 proteins may be fragments or variants thereof so far as they retain the ability to bind to heparin sulfate. The ability of the HS6ST2 proteins to bind to heparin sulfate and internalization activity can be assessed by methods known to those skilled in the art such as the methods described above, for example.

Pharmaceutical Compositions

In another aspect, the present invention provides pharmaceutical compositions comprising an antibody that binds to an HS6ST2 protein as an active ingredient. The present invention also relates to cytostatic agents, especially anticancer agents comprising an antibody that binds to an HS6ST2 protein as an active ingredient. The cytostatic agents and anticancer agents of the present invention are preferably administered to a subject suffering from cancer or a subject suspected of suffering from cancer. Administration of the anti-HS6ST2 antibody is expected to have cancer cell-specific cytotoxic effects because the expression level of HS6ST2 is increased in cancer cells.

The anti-HS6ST2 antibody used in the pharmaceutical compositions (e.g., anticancer agents) of the present invention is not specifically limited, and any anti-HS6ST2 antibody can be used, such as one of the anti-HS6ST2 antibodies described above, for example.

As used herein, the expression "comprising an antibody binding to HS6ST2 as an active ingredient" means comprising an anti-HS6ST2 antibody as a major active ingredient, but should not be construed to limit the content of the anti-HS6ST2 antibody.

The present invention also provides pharmaceutical compositions comprising an HS6ST2 protein conjugated to a cytotoxic agent as an active ingredient. The present invention also provides cytostatic agents, especially anticancer agents comprising an HS6ST2 protein conjugated to a cytotoxic agent as an active ingredient. The cytostatic agents and anticancer agents of the present invention are preferably administered to a subject suffering from cancer or a subject suspected of suffering from cancer.

As used herein, the expression "comprising an HS6ST2 protein conjugated to a cytotoxic agent as an active ingredient" means comprising an HS6ST2 protein conjugated to a cytotoxic agent as a major active ingredient, but should not be construed to limit the content of the HS6ST2 protein conjugated to a cytotoxic agent.

When the disease targeted by the pharmaceutical compositions of the present invention is cancer, the target cancer is not specifically limited, but preferably lung adenocarcinoma, lung cancer, liver cancer, ovarian cancer, and squamous cell lung carcinoma. The cancer may be either primary lesion or metastatic lesion.

The pharmaceutical compositions of the present invention can be administered to patients orally or parenterally. Parenteral administration is preferred. Such administration routes specifically include injection, nasal, pulmonary and transdermal administrations, etc. As examples of administration by injection, the pharmaceutical compositions of the present invention can be systemically or topically administered by intravenous injection, intramuscular injection, intraperitoneal injection, or subcutaneous injection, for example. The mode of administration can be appropriately selected depending on the age and condition of the patient. The dosage can be selected in the range of 0.0001 mg-1000 mg/kg body weight in a single dose, for example. Alternatively, the dosage can be selected in the range of 0.001-100,000 mg/body per patient, for example. However, the pharmaceutical compositions of the present invention are not limited to these dosages.

The pharmaceutical compositions of the present invention can be formulated by conventional methods (e.g., Remington's Pharmaceutical Science, latest edition, Mark Publishing Company, Easton, U.S.A), and may also contain pharmaceutically acceptable carriers and additives. For example, surfactants, excipients, colorants, flavoring agents, preservatives, stabilizers, buffers, suspending agents, isotonizing agents, binders, disintegrating agents, lubricants, glidants, taste masking agents and the like are included. Furthermore, other conventional carriers can be used as appropriate. Specifically, carriers include light anhydrous silicic acid, lactose, crystalline cellulose, mannitol, starch, carmellose calcium, carmellose sodium, hydroxypropyl cellulose, hydroxypropyl methylcellulose, polyvinylacetal diethylaminoacetate, polyvinylpyrrolidone, gelatin, medium-chain fatty acid triglycerides, polyoxyethylene hydrogenated castor oil 60, sucrose, carboxymethylcellulose, corn starch, mineral salts, etc.

Methods for Inducing Damage to or Inhibiting Proliferation of HS6ST2-Expressing Cells The present invention also provides methods for inducing damage to or inhibiting proliferation of HS6ST2-expressing cells by contacting the HS6ST2-expressing cells with an antibody that binds to an HS6ST2 protein.

The antibody used in the methods of the present invention is not specifically limited, but the antibodies described above can be used, for example. The cells to which the anti-HS6ST2 antibody binds are not specifically limited so far as they express HS6ST2. Preferred HS6ST2-expressing cells in the present invention are cancer cells. More preferably, they are lung adenocarcinoma cells, lung cancer cells, liver cancer cells, ovarian cancer cells, and squamous cell lung carcinoma cells. The methods of the present invention can be applied to both primary and metastatic lesions of these cancer cells.

In the present invention, the "contact" is accomplished by adding an antibody to in vitro cultures of HS6ST2-expressing cells, for example. In the present invention, the "contact" is also accomplished by administering an antibody to a non-human animal implanted with an HS6ST2-expressing cell or an animal having a cancer cell endogenously expressing HS6ST2.

Methods for evaluating or assaying cytotoxicity induced in HS6ST2-expressing cells by contact with an anti-HS6ST2 antibody conveniently include the following methods. Methods for evaluating or assaying the cytotoxic activity in vitro include the assays described above for antibody-dependent cell-mediated cytotoxicity (ADCC) activity, complement-dependent cytotoxicity (CDC) activity or the like. Whether or not an anti-HS6ST2 antibody has ADCC activity or whether or not it has CDC activity can be determined by known methods (e.g., Current protocols in Immunology, Chapter 7. Immunologic studies in humans, Editor, John E, Coligan et al., John Wiley & Sons, Inc., (1993), etc.). To assess the activity, a binding antibody having the same isotype as the anti-HS6ST2 antibody but lacking the cytotoxic activity is used as a control antibody in the same manner as the anti-HS6ST2 antibody, whereby the anti-HS6ST2 antibody can be assessed to have the activity if it shows stronger cytotoxic activity than the control antibody.

The isotype of an antibody is defined by the sequence of the heavy chain constant region of the amino acid sequence of the antibody. In vivo, the isotype of an antibody is finally determined by class switching caused by genetic recombination on chromosomes during maturation of antibody-producing B cells. The isotype difference is reflected in the difference of physiological/pathological functions of the antibody. Specifically, the strength of cytotoxic activity is known to be influenced by not only the expression level of the antigen but also the isotype of the antibody, for example. Thus, the antibody used as control during the determination of the cytotoxic activity described above preferably has the same isotype as the test antibody.

To evaluate or determine cytotoxic activity in vivo, an HS6ST2-expressing cancer cell is intracutaneously or subcutaneously implanted into a non-human test animal, and then a test antibody is intravenously or intraperitoneally administered everyday or every several days started from the day of implantation or the following day, for example. Cytotoxic activity can be assessed by measuring the tumor size daily. Similarly to the in vitro evaluation, a control antibody having the same isotype is administered, whereby a group treated with an anti-HS6ST2 antibody can be assessed to have cytotoxic activity if the tumor size is significantly smaller than the tumor size in the group treated with the control antibody. When a mouse is used as a non-human test animal, a nude (nu/nu) mouse can be conveniently used, which is deficient in T lymphocyte functions because it genetically lacks a thymus. The use of such a mouse can avoid the participation of T lymphocytes in the test animal during the evaluation/determination of cytotoxic activity of the antibody administered.

Methods for Diagnosing Cancer

The present invention also provides methods for diagnosing cancer, characterized by detecting an HS6ST2 protein or a gene encoding an HS6ST2 protein. Remarkably increased expression of HS6ST2 has been observed in various cancer tissues or cancer cell lines. Thus, HS6ST2 is useful as a marker for specifically detecting cancer.

Therefore, the present invention provides a method for diagnosing cancer, comprising the steps of:
(a) providing a sample collected from a subject, and
(b) detecting an HS6ST2 protein or HS6ST2 gene contained in the sample of (a).

In one embodiment of the method of the present invention, cancer is diagnosed by detecting an HS6ST2 protein in a sample. The detection of an HS6ST2 protein is preferably performed by using an antibody that recognizes the HS6ST2 protein.

A specific example of the diagnostic method of the present invention includes a method for diagnosing cancer, comprising the steps of:
(a) providing a sample collected from a subject, and
(b) detecting an HS6ST2 protein contained in the collected sample using an antibody that binds to the HS6ST2 protein.

As used herein, the term "detection" encompasses quantitative or qualitative detection. For example, qualitative detection includes the following determinations.

Determination of whether or not an HS6ST2 protein simply exists;
Determination of whether or not an HS6ST2 protein exists in a predetermined amount or more;
Determination of the amount of an HS6ST2 protein in comparison to the amount in another sample (e.g., control sample, etc.), etc.

On the other hand, quantitative detection includes determination of the concentration of an HS6ST2 protein, determination of the amount of an HS6ST2 protein, etc.

The test sample in the present invention is not specifically limited so far as it is likely to contain an HS6ST2 protein. Specifically, a sample collected from an organism such as a mammal is preferred. A sample collected from a human is more preferred. Specific examples of test samples include, for example, blood, interstitial fluid, plasma, extravascular fluid, cerebrospinal fluid, synovial fluid, pleural fluid, serum, lymph fluid, saliva, urine, tissue, etc. A preferred sample is derived from a fixed specimen of a tissue or cell collected from an organism or a cell culture.

The cancer diagnosed by the present invention is not specifically limited, but may be any cancer. Specifically, lung adenocarcinoma, lung cancer, liver cancer, ovarian cancer, squamous cell lung carcinoma and the like are included. In the present invention, both primary and metastatic lesions of these cancers can be diagnosed.

In the present invention, cancer is diagnosed on the basis of the level of a protein if it is detected in a test sample. Specifically, a subject is diagnosed to have cancer or to be more likely to have cancer in future if the amount of an HS6ST2 protein detected in a test sample is higher than the amount in a negative control or a healthy normal. Thus, the present invention relates to a method for diagnosing cancer, comprising the steps of:

(1) detecting the expression level of HS6ST2 in a biological sample collected from a subject, and
(2) indicating that the subject has cancer if the expression level of HS6ST2 detected in (1) is higher than a control.

As used herein, the term "control" refers to a sample that provides a basis for comparison, and includes a biological sample from a negative control or a healthy normal. The negative control can be obtained by collecting a biological sample from a healthy normal and optionally mixing multiple such samples. The expression level of HS6ST2 in the control can be detected in parallel with the expression level of HS6ST2 in a biological sample from a subject. Alternatively, a standard expression level in healthy normals can be statistically determined by detecting the expression levels of HS6ST2 in biological samples from a large number of healthy normals in advance. Specifically, the mean±2×standard deviation (S.D.) or the mean±3×standard deviation (S.D.) can be used as a standard level, for example. Statistically, the mean±2×standard deviation (S.D.) and the mean±3×standard deviation (S.D.) include 80% and 90% of the levels in healthy normals, respectively.

Alternatively, the expression level of HS6ST2 in a control can be established by using a ROC curve. The ROC curve (receiver operating characteristic curve) is a graph showing detection sensitivity on the ordinate and false positive rate (i.e., "1—specificity") on the abscissa. In the present invention, a ROC curve can be obtained by plotting changes in sensitivity and false positive rate in response to continuous variation of a reference value for determining the expression level of HS6ST2 in a biological sample.

The "reference value" for obtaining a ROC curve is a numerical value temporarily used for statistical analysis. The "reference value" for obtaining a ROC curve is normally continuously varied in the range capable of covering all selectable reference values. For example, the reference value can be varied between the minimum and the maximum of the measured values of HS6ST2 in a population analyzed.

Based on the resulting ROC curve, a standard value promising a desired detection sensitivity and precision can be selected. A standard value statistically established by a ROC curve or the like is also known as a cut-off value. In a cancer detection method based on a cut-off value, the expression level of HS6ST2 detected in the step (1) above is compared with a cut-off value in (2). If the expression level of HS6ST2 detected in (1) is higher than the cut-off value, cancer is detected in the subject.

In the present invention, the expression level of HS6ST2 can be determined by any method. Specifically, the expression level of HS6ST2 can be known by evaluating the amount of mRNA of HS6ST2, the amount of the HS6ST2 protein, and biological activity of the HS6ST2 protein. The amount of mRNA of HS6ST2 or the protein can be determined by the methods as described herein.

In the present invention, an especially preferred subject is a human. When a non-human animal is a subject, the HS6ST2 protein of the animal species is detected.

The method for detecting an HS6ST2 protein contained in a test sample is not specifically limited, but it is preferably detected by an immunological method using an anti-HS6ST2 antibody, as shown below:

Radioimmunoassay (RIA),
Enzyme immunoassay (EIA),
Fluorescent immunoassay (FIA),
Luminescent immunoassay (LIA),
Immunoprecipitation (IP),
Turbidimetric immunoassay (TIA),
Western blotting (WB),
Immunohistochemistry (IHC),
Single radial immunodiffusion (SRID).

Among these methods, immunohistochemistry (IHC) is one of preferred immunoassays for cancer diagnosis, comprising the step of detecting an HS6ST2 protein on a fixed section of a tissue or cell collected from a patient suffering from cancer. The immunological methods listed above including immunohistochemistry (IHC) are known to those skilled in the art.

Thus, cancer cells or cancer tissues can be detected by anti-HS6ST2 antibodies because HS6ST2 is a membrane protein showing increased expression specifically in cancer cells. Cancer cells contained in cells or tissues collected from organisms can be detected by the immunohistological analysis described above.

In another preferred embodiment, in vivo cancer tissues can also be detected by anti-HS6ST2 antibodies. Thus, the present invention relates to a method for detecting cancer, comprising the steps of: (1) administering an HS6ST2 protein-binding antibody conjugated to a label such as a radioisotope to a subject, and (2) detecting accumulation of the label. To track the antibody administered in vivo, the antibody can be detectably labeled. For example, the in vivo behavior of the antibody labeled with a fluorescent or luminescent substance or a radioisotope can be tracked. The antibody labeled with a fluorescent or luminescent substance can be observed by endoscopy or abdominoscopy. The localization of the antibody can be imaged by tracking the radioactivity of a radioisotope. In the present invention, in vivo localization of an anti-HS6ST2 antibody indicates the presence of a cancer cell.

Positron-emitting radionuclides can be employed as radioisotopes for labeling antibodies in order to detect cancer in vivo. For example, antibodies can be labeled with positron-emitting radionuclides such as 18F, 55Co, 64Cu, 66Ga, 68Ga, 76Br, 89Zr, and 124I. For labeling anti-HS6ST2 antibodies with these positron-emitting radionuclides, known methods can be employed (Acta Oncol. 32, 825-830, 1993).

After an anti-HS6ST2 antibody labeled with a positron-emitting radionuclide is administered to a human or an animal, the radiation emitted by the radionuclide is externally measured by PET (positron emission tomography) and converted into an image by computed tomography. PET is a system for non-invasively collecting data about in vivo behavior of drugs or the like. PET allows the intensity of radiation to be quantitatively imaged as a signal intensity. An antigen molecule highly expressed in specific cancer can be detected without collecting a sample from a patient by using PET as described above. Anti-HS6ST2 antibodies can also be radioactively labeled with short-lived nuclides using positron-emitting radionuclides such as 11C, 13N, 15O, 18F, 45Ti, etc., in addition to the nuclides mentioned above.

Research and development are being devoted to finding techniques for producing short-lived nuclides by medical cyclotrons using the nuclides above, or preparing short-lived radioactive labeling compounds, etc. These techniques enable anti-HS6ST2 antibodies to be labeled with various radioisotopes. An anti-HS6ST2 antibody administered to a patient accumulates at primary and metastatic lesions according to the specificity of the anti-HS6ST2 antibody to a pathological tissue at each site. If the anti-HS6ST2 antibody is labeled with a positron-emitting radionuclide, the presence of the primary and metastatic lesions can be detected by localization of the radioactivity by detecting the radioactivity. For use in diagnosis, an activity value of gamma or positron emission of 25-4000 keV can be conveniently used. Therapeutic effects can also be expected by selecting a suitable nuclide and administering it in larger amounts. To provide radiation-based anticancer effects, nuclides giving a gamma or positron emission dose of 70-700 keV can be used.

In another embodiment of the method of the present invention, the expression of the gene for HS6ST2 is detected. In the present invention, the gene to be detected is not specifically limited, but preferably mRNA. As used herein, the term "detection" encompasses quantitative or qualitative detection. For example, qualitative detection includes the following determination operations.

Determination of whether or not mRNA of HS6ST2 simply exists;
Determination of whether or not mRNA of HS6ST2 exists in a predetermined amount or more;
Determination of the amount of mRNA of HS6ST2 in comparison to the amount in another sample (e.g., control sample, etc.), etc.

On the other hand, quantitative detection includes determination of the concentration of mRNA of HS6ST2, determination of the amount of mRNA of HS6ST2, etc.

Any sample likely to contain mRNA of HS6ST2 can be used as a test sample in the present invention. A sample collected from an organism such as a mammal is preferred, and a sample collected from a human is more preferred. Specific examples of test samples include, for example, blood, interstitial fluid, plasma, extravascular fluid, cerebrospinal fluid, synovial fluid, pleural fluid, serum, lymph fluid, saliva, urine, tissue, etc. Preferably, a sample derived from a fixed specimen of a tissue or cell collected from an organism or a cell culture is also included in test samples of the present invention.

When a sample derived from a fixed specimen of a tissue or cell collected from an organism or a cell culture is used, in situ hybridization is conveniently used. In situ hybridization has been developed as a technique for assessing the presence of specific DNA or RNA in a cell or tissue or the distribution and intensity of its expression. It is based on the principle that a probe nucleic acid having a nucleotide sequence complementary to a specific nucleic acid sequence in a cell specifically forms a complex with it. In situ hybridization is used for the detection of DNA and RNA in cells because the probe has been labeled with a radioisotope (RI) or an antigenic substance (hapten) or the like in advance so that the hybridized target can be identified by detecting the label. For labeling the probe, RI-labeling can be conveniently used. As a more preferred example, fluorescent labeling with a non-radioactive substance such as a hapten including biotin or digoxigenin can be used. As an especially preferred example, a detection method based on fluorescent in situ hybridization known as FISH is used.

The cancer diagnosed herein is not specifically limited. Specifically, lung adenocarcinoma, lung cancer, liver cancer, ovarian cancer, squamous cell lung carcinoma and the like are included. In the present invention, both primary and metastatic lesions of these cancers can be diagnosed.

In the present invention, the subject can be any animal species that expresses the HS6ST2 gene. An especially preferred subject is a human. When a non-human animal is a subject, the HS6ST2 protein of the animal species is detected.

A specific embodiment of the detection method is as follows. First, a sample is prepared from a subject. Then, mRNA of HS6ST2 contained in the sample is detected. In the present invention, cDNA synthesized from mRNA can also be detected. In the present invention, the possibility of cancer is indicated if mRNA of HS6ST2 or HS6ST2-encoding cDNA is detected in a test sample. For example, a subject is diagnosed to have cancer or to be more likely to have cancer in future if the amount of mRNA of HS6ST2 or HS6ST2-encoding cDNA detected in a test sample is higher than the amount in a negative control or a healthy normal.

Methods for detecting mRNA are known. Specifically, Northern blotting, RT-PCR, DNA array, etc. can be applied to the present invention, for example.

The detection method of the present invention described above can be automated by using various automatic inspection equipments. Automation enables quick inspection of a number of samples.

Reagents, Kits

The present invention also provides diagnostics or kits for diagnosing cancer, comprising a reagent for detecting an HS6ST2 protein in a test sample. The diagnostics of the present invention comprise at least an anti-HS6ST2 antibody.

Kits for diagnosing cancer can be provided by combining a reagent for diagnosing cancer of the present invention with other components used for the detection of HS6ST2. Thus, the present invention relates to kits for diagnosing cancer, which comprise an antibody that binds to HS6ST2, and a reagent for detecting binding of the antibody to HS6ST2, and optionally may further comprise a control sample consisting of a biological sample containing HS6ST2. The kits of the present invention may further comprise instructional materials for indicating assay procedures.

The following examples further illustrate the present invention, but these examples are given for merely illustrative purposes and should not be construed to limit the technical scope of the present invention.

EXAMPLES

Example 1

Analysis of the Expression of HS6ST2 mRNA by Human Exon 1.0 ST Array

Using Human Exon 1.0 ST Array (Affymetrix), the expression of HS6ST2 mRNA was analyzed in clinical cancer specimens, cancer cell lines and various normal tissues. Human Exon 1.0 ST Array contains at least one probe set per exon for each gene so that it provides expression data for multiple probe sets per gene. This seems to increase reliability of expression data as compared with the previous expression arrays of Affymetrix essentially containing only one probe set per gene.

The samples used were total RNAs derived from tumor sites of 41 cases of isolated lung adenocarcinoma tissues, tumor sites of 13 cases of isolated small cell lung carcinoma tissues, normal sites of 2 cases of isolated lung adenocarcinoma tissues, normal sites of 10 cases of isolated colorectal cancer tissues, normal site of 1 case of isolated breast cancer tissue, 24 lung adenocarcinoma cell lines, a large cell lung carcinoma cell line, 2 squamous cell lung carcinoma cell lines, 5 small cell lung carcinoma cell lines, 89 non-lung cancer cell lines, and 69 normal tissues. The cancer cell lines were purchased from ATCC, JCRB or RIKEN, while total RNAs derived from the normal tissues were purchased from Clontech, Ambion, Stratagene, Cell Applications, Panomics, Chemicon and Biochain Institute. Total RNA was purified from the tumor and normal sites of isolated clinical cancer tissues (informed consent given) and the cancer cell lines by using Trizol (Invitrogen) following the manufacturer's protocol. Expression analysis was performed by using 1 µg of total RNA following GeneChip Whole Transcript (WT) Sense Target Labeling Assay Manual (Affymetrix). For data digitalization, ExACT (Exon Array Computational Tool) software (Affymetrix) was used.

Figure 1B:
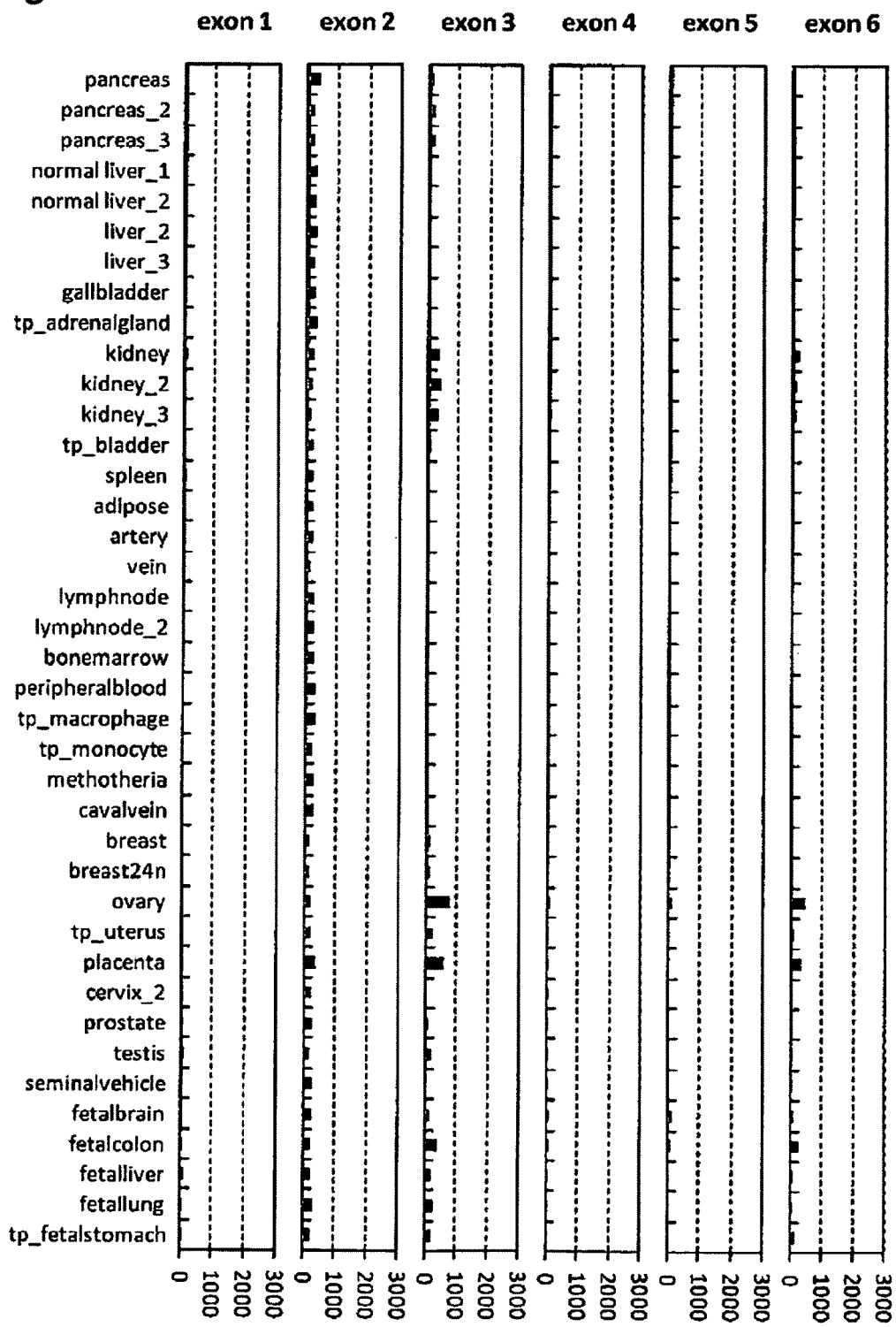
FIG. 1B is a diagram showing expression profiles of HS6ST2 in normal tissues.
Figure 2A:
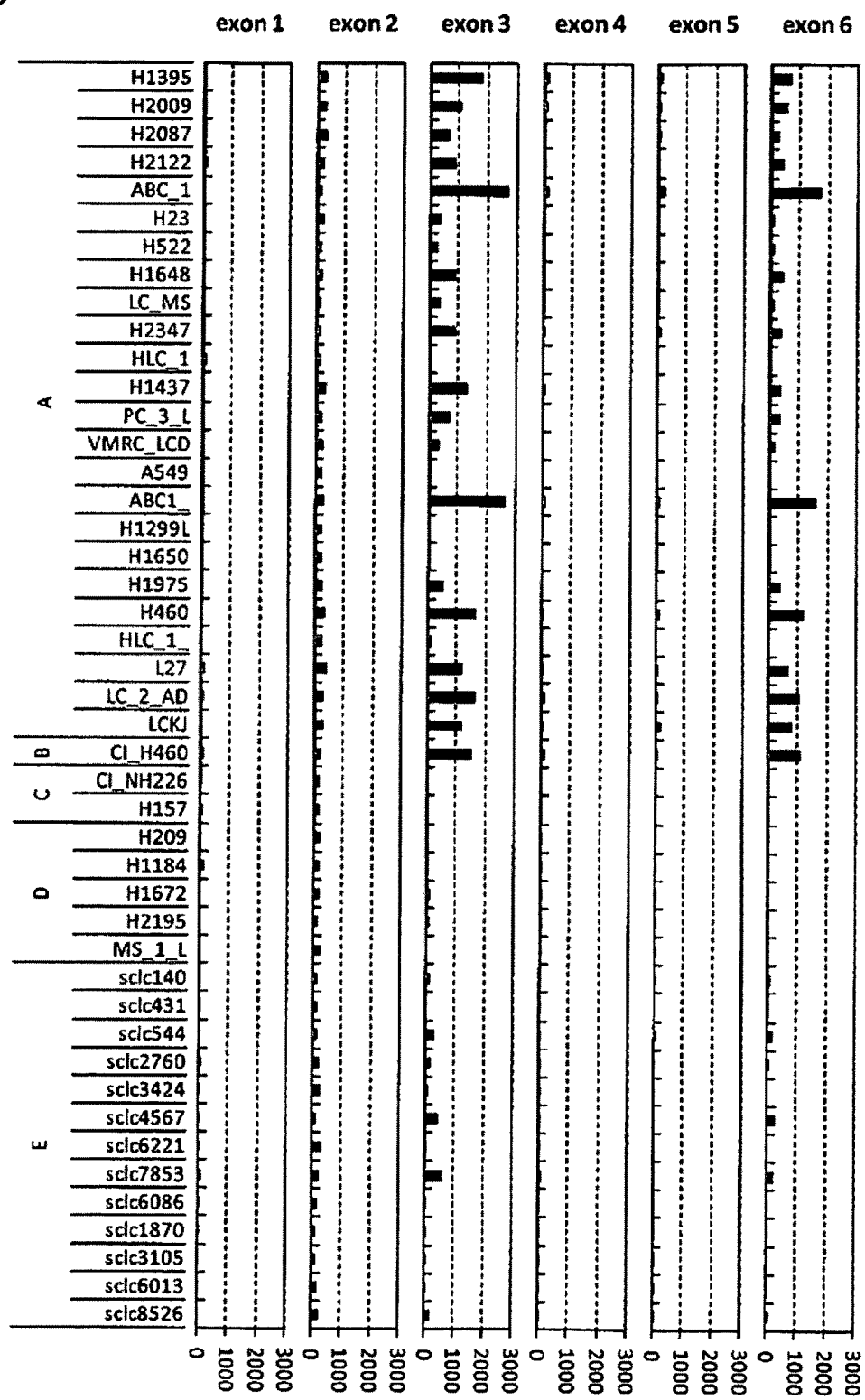
FIG. 2A is a diagram showing expression profiles of HS6ST2 in lung cancer cell lines and tumor sites of isolated lung cancer tissues. On the ordinate, A-F represent lung adenocarcinoma cell lines, a large cell lung carcinoma cell line, squamous cell lung carcinoma cell lines, small cell lung carcinoma cell lines, tumor sites of isolated small cell lung carcinoma tissues, and tumor sites of isolated lung adenocarcinoma tissues, respectively.
Figure 2B:
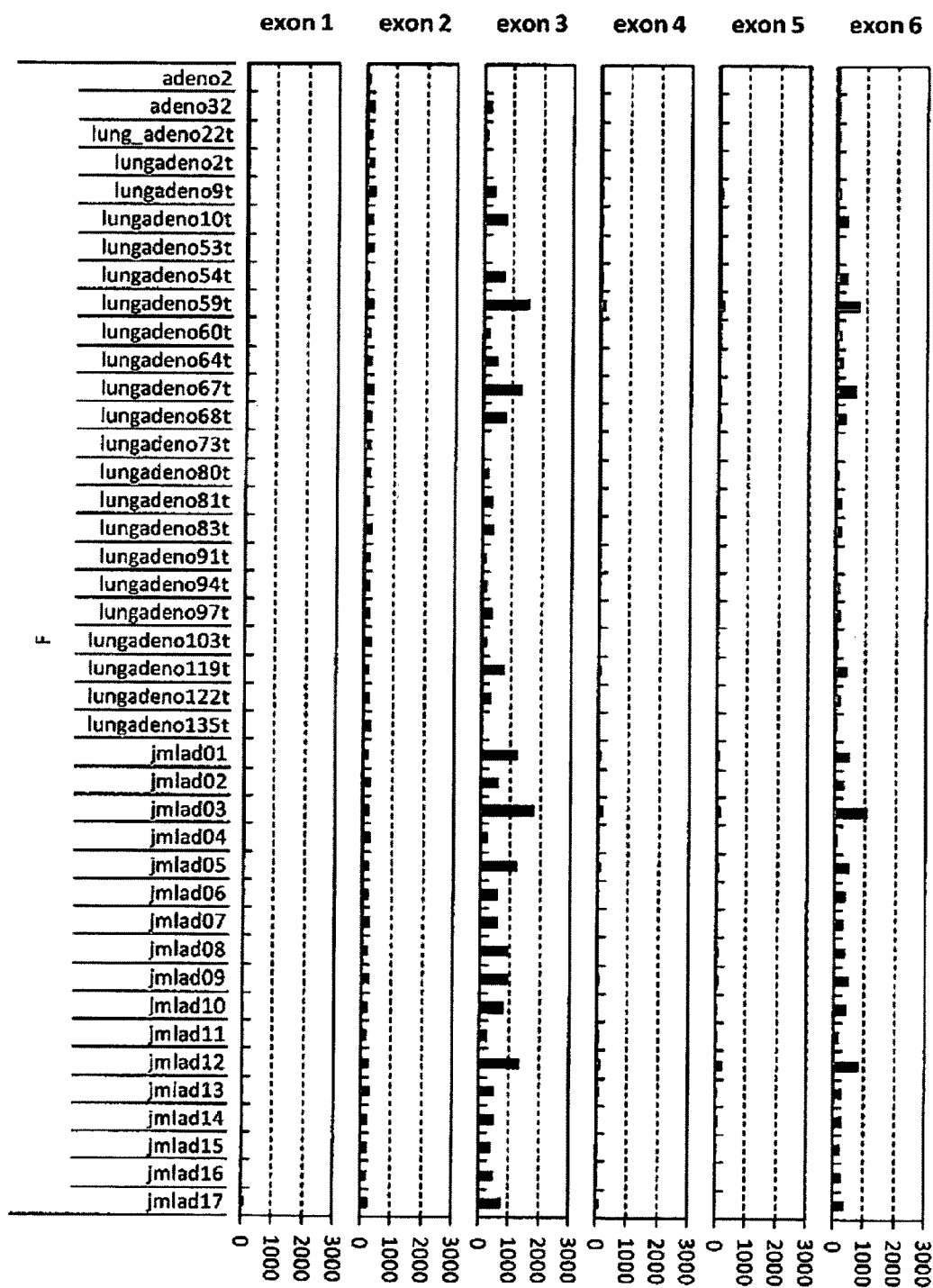
FIG. 2B is a diagram showing expression profiles of HS6ST2 in lung cancer cell lines and tumor sites of isolated lung cancer tissues. On the ordinate, A-F represent lung adenocarcinoma cell lines, a large cell lung carcinoma cell line, squamous cell lung carcinoma cell lines, small cell lung carcinoma cell lines, tumor sites of isolated small cell lung carcinoma tissues, and tumor sites of isolated lung adenocarcinoma tissues, respectively.
Figure 3A:
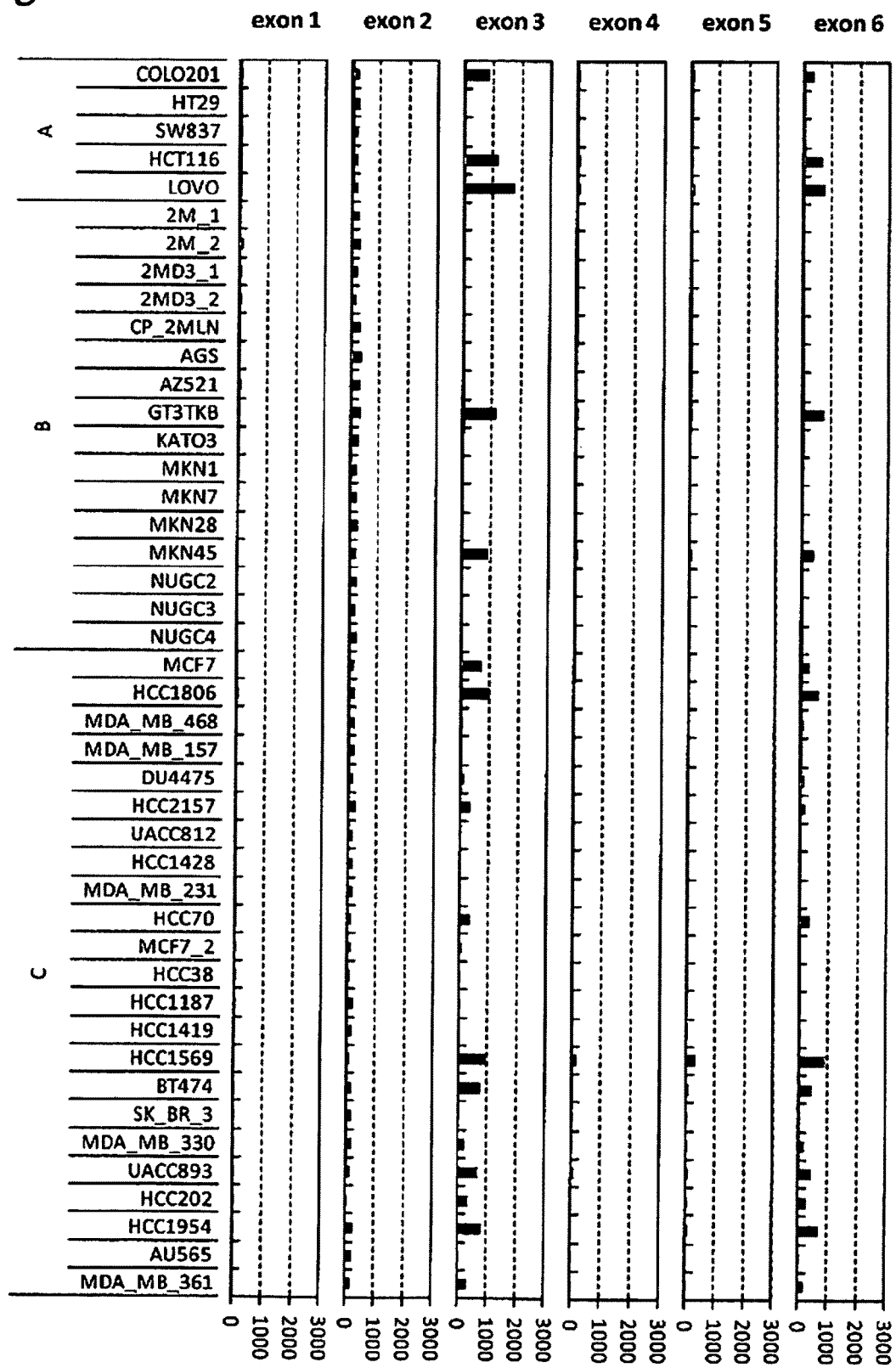
FIG. 3A is a diagram showing expression profiles of HS6ST2 in non-lung cancer cell lines. On the ordinate, A-H represent colorectal cancer cell lines, stomach cancer cell lines, breast cancer cell lines, ovarian cancer cell lines, a uterine body cancer cell line, lymphoma cell lines, myeloma cell lines, and liver cancer cell lines, respectively.
Figure 3B:
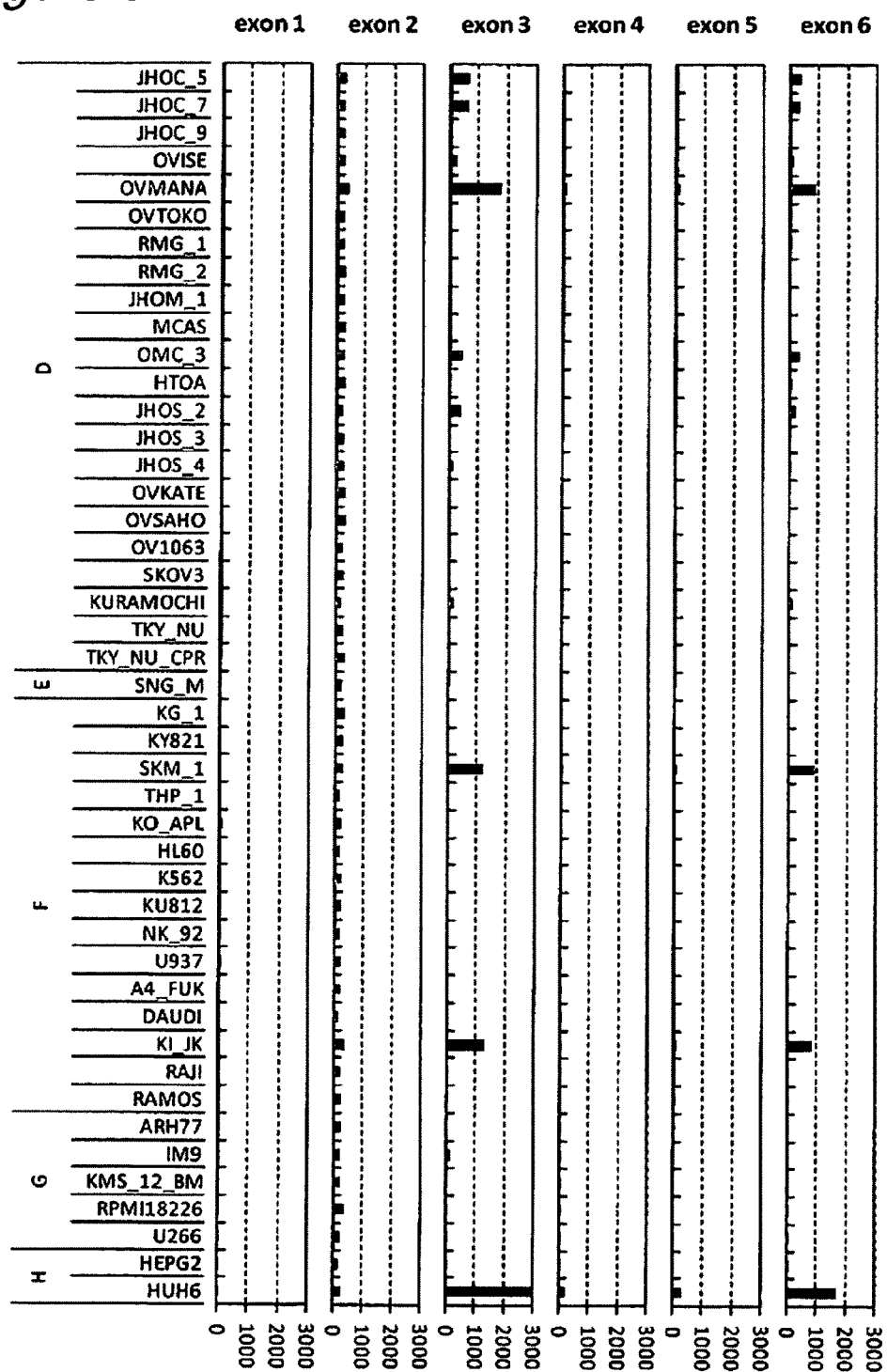
FIG. 3B is a diagram showing expression profiles of HS6ST2 in cell lines other than lung cancer. On the ordinate, A-H represent colorectal cancer cell lines, stomach cancer cell lines, breast cancer cell lines, ovarian cancer cell lines, a uterine body cancer cell line, lymphoma cell lines, myeloma cell lines, and liver cancer cell lines, respectively.

The core probe sets for HS6ST2 in Human Exon 1.0 ST Array include one for exon 1 (probe set ID: 4022257), five for exon 2 (4022252, 4022253, 4022254, 4022255, 4022256), one for exon 3 (4022247), one for exon 4 (4022221), two for exon 5 (4022212, 4022213), and seven for exon 6 (4022194, 4022195, 4022196, 4022197, 4022198, 4022199, 1022200). Expression data for the exons to which multiple core probe sets correspond were the averages of values for all core probe sets of these exons. The probe set ID 4022253 showed negative values in all samples and therefore, it was considered to be unreliable and excluded from data analysis. Expression data from normal tissues were shown in FIG. 1A and FIG. 1B; expression data from lung cancer cell lines and tumor sites of isolated lung cancer tissues were shown in FIG. 2A and FIG. 2B; and expression data from non-lung cancer cell lines were shown in FIG. 3A and FIG. 3B.

As determined from expression data, exons 1 and 2 seemed to be unexpressed or reflect dead probe sets. As previously reported (Biosynthesis of heparan sulphate with diverse structures and functions: two alternatively spliced forms of human heparan sulphate 6-O-sulphotransferase-2 having different expression patterns and properties. Biochem J. 2003. 371:131), exons 4 and 5 seemed to be expressed in brain only. Thus, expression data for exons 3 and 6 were reviewed to show expression in normal tissues from brain, ovary, placenta and kidney, but also show similar or higher levels of expression in tumor sites of isolated lung adenocarcinoma tissues, tumor sites of isolated small cell lung carcinoma tissues, lung adenocarcinoma cell lines, and large cell lung carcinoma cell lines. Especially, they are highly expressed in lung adenocarcinoma at high frequency, indicating that HS6ST2 can be a potential therapeutic target molecule or diagnostic marker for lung adenocarcinoma.

Example 2

Preparation of Antibodies to HS6ST2

2-1. Cloning of HS6ST2

As shown in Example 1, a variant of HS6ST2 lacking exons 4 and 5 seemed to be expressed in cancer cells. The gene sequence of this variant has been deposited in RefSeq under NM_147175. Its amino acid sequence has been deposited in UniProt under Q96MM7-1. On the other hand, a variant of Q96MM7-1 lacking amino acids 1-146 has been deposited under Q96MM7-2. Q96MM7-2 corresponds to a protein whose translation starts at the eleventh nucleotide of exon 3. As shown in Example 1, the expression of exons 1 and 2 was not observed in Human Exon 1.0 ST Array and the first cloned HS6ST2 had an amino acid sequence corresponding to Q96MM7-2 (Biosynthesis of heparan sulphate with diverse structures and functions: two alternatively spliced forms of human heparan sulphate 6-O-sulphotransferase-2 having different expression patterns and properties. Biochem J. 2003. 371:131), suggesting that Q96MM7-2 is dominantly expressed. Thus, Q96MM7-2 was designated as HS6ST2_N-short and cloned. First, total RNA was isolated from the cancer cell line HuH6 (RIKEN) using Trizol (Invitrogen) following the manufacturer's protocol, and cDNA was constructed using SuperScript III Reverse Transcriptase (Invitrogen) following the manufacturer's protocol. This cDNA was used as a template with a primer of SEQ ID NO: 1 (the 5'-end sequence of HS6ST2_N-short) and a primer of SEQ ID NO: 2 (the 3'-end sequence of HS6ST2_N-short excluding the stop codon) to perform PCR amplification, and the amplified product was cloned into a TOPO vector (TOPO_HS6ST2_N-short) using TOPO TA Cloning Kit (Invitrogen). The PCR amplification was performed using Pyrobest DNA Polymerase (Takara Bio) in a solution containing 3 μL of 10× Pyrobest buffer II, 3 μL of dNTP mixture, 3 μL of HuH6 cDNA, 1 μL of the primer of SEQ ID NO: 1 (50 μM), 1 μL of the primer of SEQ ID NO: 2 (50 μM), 0.5 μL of Pyrobest DNA Polymerase and 18.5 μL of nuclease-free water, at 94° C. for 1 min, and 35 cycles×(94° C. for 30 sec, 62° C. for 30 sec, 72° C. for 1.5 min). One μL of this PCR product was used as a template to perform PCR reamplification in the same manner. The sequence of TOPO_HS6ST2_N-short was determined to confirm that it was the same as RefSeq Accession No. NM_147175.

2-2. Preparation of a CHO Cell Line Expressing HS6ST2_N-Short

HS6ST2_N-short cDNA was cloned into a mammalian cell expression vector (pMCDN2_ctV5). The expression vector pMCDN2_ctV5 is a vector capable of inducing expression under control of the mouse CMV promoter (GenBank Accession No. U68299) and bearing the neomycin resistance gene. Further, a V5 tag sequence is added to the 3'-end of the inserted gene of interest. The V5 tag is a 14-amino acid sequence of GKPIPNPLLGLDST recognized by anti-V5 antibodies (Invitrogen). The sequence of the expression vector pMCDN2_ctV5 consisting of EcoRI recognition sequence—Kozak sequence—start codon—multicloning site (NheI, SalI, NotI)—V5 tag sequence—stop codon is shown in SEQ ID NO: 3. PCR amplification was performed using a primer of SEQ ID NO: 4 (EcoRI recognition sequence—Kozak sequence—the 5'-end sequence of HS6ST2_N-short) and a primer of SEQ ID NO: 5 (NotI recognition sequence—the 3'-end sequence of HS6ST2_N-short excluding the stop codon) with TOPO_HS6ST2_N-short as a template. The amplified fragment was digested with EcoRI and NotI, and cloned into the EcoRI/NotI sites of pMCDN2_ctV5 (pMCDN2_HS6ST2_N-short_ctV5). The nucleotide sequence of pMCDN2_HS6ST2_N-short_ctV5 from the start codon to the stop codon is shown in SEQ ID NO: 6, and its amino acid sequence is shown in SEQ ID NO: 7.

The PvuI digest of pMCDN2_HS6ST2_N-short_ctV5 was transformed into the CHO DG44 cell line by electroporation. A CHO cell line stably expressing C-terminal V5 tagged HS6ST2_N-short (HS6ST2_N-short_ctV5_CHO) was established by selecting the transformed cell line with 500 μg/mL Geneticin (Invitrogen). The culture medium used was CHO-S-SFM II medium (Invitrogen) containing 500 μg/mL Geneticin, HT supplement (Invitrogen) and penicillin/streptomycin (Invitrogen) (hereinafter referred to as CHO medium).

2-3. Preparation of an Expression Vector for DNA Immunization

HS6ST2_N-short cDNA was cloned into a mammalian cell expression vector (pMC). pMC is a vector capable of inducing expression under control of the mouse CMV promoter. PCR amplification was performed using the primer of SEQ ID NO: 4 and a primer of SEQ ID NO: 8 (SalI recognition sequence—stop codon—the 3'-end sequence of HS6ST2_N-short excluding the stop codon) with pMCDN2_HS6ST2_N-short_ctV5 as a template. The amplified fragment was digested with EcoRI and SalI, and cloned into the EcoRI/SalI sites of pMC (pMC_HS6ST2_N-short).

2-4. Preparation of Soluble HS6ST2 Protein

An expression vector was prepared for secreted HS6ST2 (sHS6ST2_FLAG), which is a protein containing a signal sequence (a 24-amino acid sequence of MRPSGTAGAAL-LALLAALCPASRA) of an epidermal growth factor receptor (EGFR, RefSeq Accession No. NM_005228) in place of the transmembrane domain (16 amino acids 8-23 of LLLALVM-LFLFAVIVL) deleted from the N-terminus of HS6ST2_N-short and further containing a FLAG tag sequence (a 8-amino acid sequence of DYKDDDDK recognized by anti-FLAG antibodies) at the C-terminus. PCR amplification was performed using a primer of SEQ ID NO: 9 (the 3'-end sequence of the EGFR signal sequence—the sequence downstream of the transmembrane domain of HS6ST2_N-short) and a primer of SEQ ID NO: 10 (NotI recognition sequence—stop codon—FLAG tag sequence—the 3'-end sequence of HS6ST2_N-short excluding the stop codon) with pMCDN2_HS6ST2_N-short_ctV5 as a template. This PCR product was used as a template with a primer of SEQ ID NO: 11 (EcoRI recognition sequence—Kozak sequence—the 5'-end sequence of the EGFR signal sequence) and the primer of SEQ ID NO: 10 to perform PCR amplification. The amplified fragment was digested with EcoRI and NotI, and cloned into the EcoRI/NotI sites of pMCDN2 (pMCDN2_sHS6ST2_FLAG). pMCDN2 is a vector capable of inducing expression under control of the mouse CMV promoter and bearing the neomycin resistance gene. The nucleotide sequence of pMCDN2_sHS6ST2_FLAG from the start codon to the stop codon is shown in SEQ ID NO: 12, and its amino acid sequence is shown in SEQ ID NO: 13.

The PvuI digest of pMCDN2_sHS6ST2_FLAG was transformed into the CHO DG44 cell line by electroporation. A CHO cell line stably expressing sHS6ST2_FLAG (sHS6ST2_FLAG_CHO) was established by selecting the transformed cell line with Geneticin (500 μg/mL). The culture medium used was CHO medium.

From the culture supernatants of the established sHS6ST2_FLAG_CHO cells was purified sHS6ST2_FLAG. The culture supernatants were applied to an anti-FLAG antibody-conjugated affinity gel (Sigma) and washed with binding buffer (50 mM Tris HCl, pH7.6, 150 mM NaCl), and then eluted with elution buffer (0.1 M glycine HCl, pH3.5). The eluate was immediately neutralized with neutralization buffer (1M Tris HCl, pH8.0), and then replaced with Dulbecco's phosphate-buffered saline (PBS, Invitrogen) using PD10 column (GE Healthcare). The concentration of purified sHS6ST2_FLAG was determined by using DC Protein Assay Kit I (Bio-Rad) following the manufacturer's protocol. Bovine γ-globulin included in the kit was used as a standard.

2-5. Preparation of Anti-HS6ST2 Antibodies

BALB/c mice (female, 6 weeks of age, Charles River Laboratories Japan, Inc.) were subjected to DNA immunization twice a week in total of 11 times using Helios Gene Gun (Bio-Rad) following the manufacturer's protocol. For the DNA immunization, the expression vector pMC_HS6ST2_N-short was used. Subsequent to the DNA immunization, 40 μg of sHS6ST2_FLAG emulsified in Freund's complete adjuvant (Becton Dickinson) was administered subcutaneously. After two weeks, 40 μg of sHS6ST2_FLAG emulsified in Freund's incomplete adjuvant (Becton Dickinson) was administered subcutaneously. After another one week, 50 μg of sHS6ST2_FLAG was administered into the tail vein. After 3 days, spleen cells were isolated and mixed with the mouse myeloma cell line P3-X63Ag8U1 (P3U1, ATCC) in 2:1, and PEG1500 (Roche Diagnostics) was gradually added to prepare hybridomas. After centrifugation in RPMI1640 medium (Invitrogen), PEG1500 was removed by removing the supernatant. Then, the hybridomas were suspended in HAT medium (RPMI1640 medium containing 10% fetal bovine serum (FBS), penicillin-streptomycin, 1×HAT media supplement (Sigma), 0.5× BM-Condimed H1 Hybridoma Cloning Supplement (Roche Diagnostics)), and plated on eight 96-well plates at a density of 1×10⁵ P3U1 cells/well. After incubation at 37° C. in a 5% $CO_2$ incubator for 7 days, the plates were screened using the culture supernatants. Screening was performed by assaying binding of antibodies contained in the culture supernatants to HS6ST2_N-short_ctV5_CHO cells and CHO cells of the parent strain using a flow cytometer (FACS Calibur, Becton Dickinson). Hybridomas that specifically bound to HS6ST2_N-short_ctV5_CHO cells were continuously cultured and screened again in the same manner, and then monocloned by limiting dilution. Thus, clones A1, A6 and A10 were established as antibodies that specifically bind to HS6ST2.

Subsequently, a second immunization was performed. To BALB/c mice (female, 6 weeks of age) was administered subcutaneously 100 μg of sHS6ST2_FLAG emulsified in Freund's complete adjuvant. After 15 days and 23 days, 50 μg of sHS6ST2_FLAG emulsified in Freund's incomplete adjuvant was administered subcutaneously. One day after the final immunization, 50 μg of sHS6ST2_FLAG was administered into the tail vein of one animal, and after 3 days, hybridomas were prepared. Thirty-six days after the final immunization, 50 μg of sHS6ST2_FLAG was administered into the tail vein of another animal, and after 3 days, hybridomas were prepared. After screening in the same manner, clones B5, B6, C8 and C10 were established as antibodies that specifically bind to HS6ST2.

These hybridomas were cultured in HAT medium containing Ultra Low IgG FBS (Invitrogen) instead of FBS, and antibodies were purified from the culture supernatants using HiTrap Protein G HP 1 mL column (GE Healthcare). The purified antibodies were isotyped using IsoStrip (Roche), showing that all were mouse IgG1. The concentrations of the antibodies were determined using DC Protein Assay Kit I (Bio-Rad). Bovine γ-globulin included in the kit was used as a standard. The purification of antibodies, isotyping and determination of the concentration of the antibodies were performed following the manufacturer's protocol.

Example 3

Evaluation of Binding of Anti-HS6ST2 Antibodies to Mouse HS6ST2

3-1. Cloning of Mouse HS6ST2

Two variants of mouse HS6ST2, i.e., transcript variant 1 (NM_001077202) and transcript variant 2 (NM_015819) have been deposited in RefSeq. A variant corresponding to HS6ST2_N-short lacking N-terminal 146 amino acids and exons 4, 5 is transcript variant 2. Thus, transcript variant 2 was used as mouse HS6ST2 (mHS6ST2) and cloned. PCR amplification was performed using Marathon-Ready mouse spleen cDNA (Clontech) as a template with a primer of SEQ ID NO: 14 (EcoRI recognition sequence—Kozak sequence—the 5'-end sequence of mHS6ST2) and a primer of SEQ ID NO: 15 (NotI recognition sequence—the 3'-end sequence of mHS6ST2), and the amplified product was cloned into pGEM-T Easy vector using pGEM-T Easy Vector Systems (Promega) (pGEM-T_mHS6ST2). PCR amplification was performed using KOD Plus Ver.2 (Toyobo) in a solution containing 5 μL of 10×KOD Plus Ver.2 buffer, 5 μL of dNTP mixture, 4 μL of 25 mM $MgSO_4$, 1.5 μL of the primer of SEQ ID NO: 14 (10 μM), 1.5 μL of the primer of SEQ ID NO: 15 (10 μM), 4 μL of mouse spleen cDNA, 1 μL of KOD Plus Polymerase, and 28 μL of nuclease-free water, at 94° C. for 2 min, 5 cycles×(98° C. for 10 sec, 72° C. for 30 sec, 68° C. for 3 min), 5 cycles×(98° C. for 10 sec, 70° C. for 30 sec, 68° C. for 3 min), and 27 cycles×(98° C. for sec, 68° C. for 3 min).

The sequence of pGEM-T_mHS6ST2 was determined to confirm that it was the same as transcript variant 2 (RefSeq Accession No. NM_015819).

3-2. Preparation of a CHO Cell Line Expressing mHS6ST2

Into a mammalian cell expression vector (pMCDN2_ntHA) was cloned mHS6ST2 cDNA. pMCDN2_ntHA is a vector capable of inducing expression under control of the mouse CMV promoter and bearing the neomycin resistance gene. An HA tag sequence is added to the 5'-end of the inserted gene of interest. The HA tag sequence is an HA epitope sequence (YPYDVPDYA) derived from the hemagglutinin protein of influenza and recognized by HA-specific antibodies. The sequence of the expression vector pMCDN2_ntHA consisting of EcoRI recognition sequence—Kozak sequence—start codon—HA tag sequence—multicloning site (NheI, SalI, NotI)—stop codon is shown in SEQ ID NO: 16. PCR amplification was performed using a primer of SEQ ID NO: 17 (NheI recognition sequence—the 5'-end sequence of mHS6ST2 excluding the start codon) and the primer of SEQ ID NO: 15 with pGEM-T_mHS6ST2 as a template. The amplified fragment was digested with NheI and NotI, and cloned into the NheI/NotI sites of pMCDN2_ntHA (pMCDN2_mHS6ST2_ntHA).

Subsequently, mHS6ST2 cDNA was cloned into a mammalian cell expression vector (pMCDN2_ctV5). PCR amplification was performed using the primer of SEQ ID NO: 17 and a primer of SEQ ID NO: 18 (NotI recognition sequence—the 3'-end sequence of mHS6ST2 excluding the stop codon) with pMCDN2_mHS6ST2_ntHA as a template. The amplified fragment was digested with NheI and NotI, and cloned into the NheI/NotI sites of pMCDN2_ctV5 (pMCDN2_mHS6ST2_ctV5). The nucleotide sequence of pMCDN2_mHS6ST2_ctV5 from the start codon to the stop codon is shown in SEQ ID NO: 19, and its amino acid sequence is shown in SEQ ID NO: 20.

The PvuI digest of pMCDN2_mHS6ST2_ctV5 was transformed into the CHO DG44 cell line by electroporation. A CHO cell line stably expressing C-terminal V5 tagged mHS6ST2 (mHS6ST2_ctV5_CHO) was established by selecting the transformed cell line with Geneticin (500 μg/mL). The culture medium used was CHO medium.

3-3. Evaluation of Binding of Anti-HS6ST2 Antibodies to mHS6ST2

Binding of the anti-HS6ST2 antibodies prepared in Example 2 to mHS6ST2 was evaluated by flow cytometry. The cells used were mHS6ST2_ctV5_CHO, HS6ST2_N-short_ctV5_CHO as a positive control, and the CHO DG44 cell line as a negative control.

Each anti-HS6ST2 antibody or mouse IgG1 (mIgG1, BD Biosciences Pharmingen) as a negative control was added to a final concentration of 2 μg/mL into 96-well U-bottom plates (Becton Dickinson) containing 5×10⁴ cells suspended in PBS (FACS buffer) supplemented with 0.5% bovine serum albumin and 0.1% $NaN_3$. After reaction on ice for 1 hour, the cells were washed with FACS buffer. Then, an FITC-labeled anti-mouse antibody (Goat F(ab')₂ Fragment Anti-mouse IgG (H+L)-FITC, Beckman Coulter) was added as a secondary antibody, and the mixture was reacted on ice for 1 hour. The cells were washed with FACS buffer, and then suspended in FACS buffer containing 10 μg/mL propidium iodide (PI) (Sigma) and assayed by a flow cytometer (FACS Calibur, Becton Dickinson). The assay data were analyzed by CELLQuest software (Becton Dickinson), and the geo-mean of FITC fluorescent intensity was calculated for the PI-negative population of viable cells.

Figure 4:
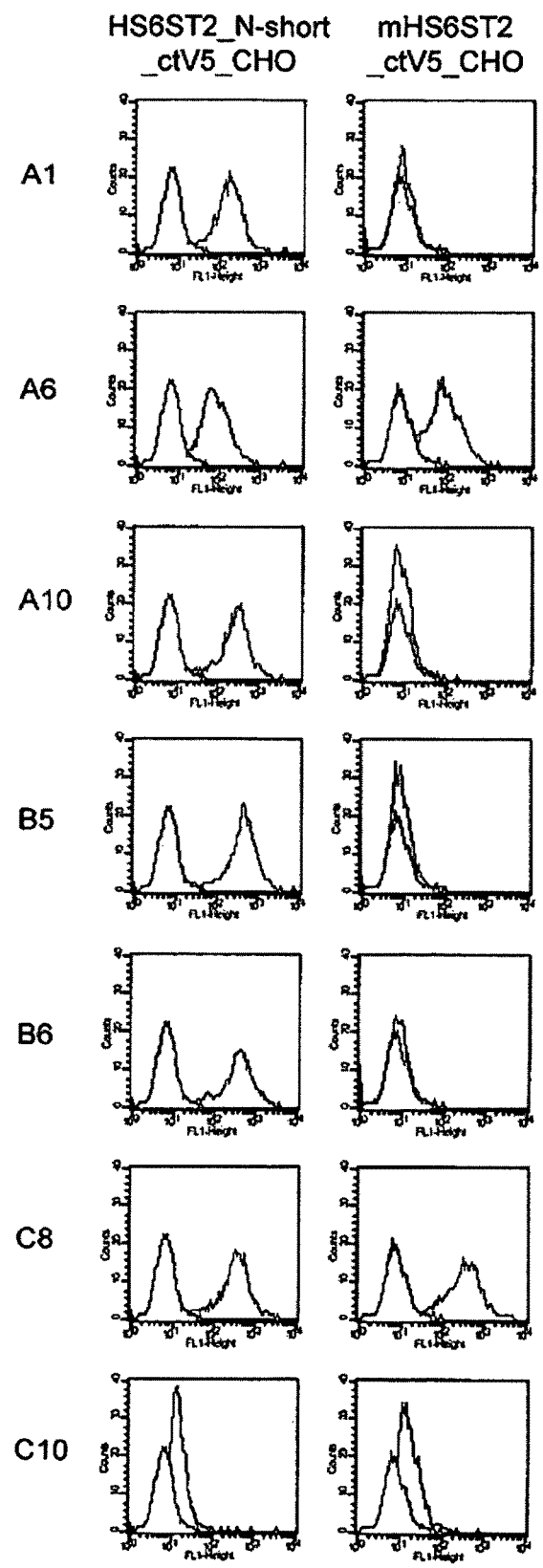
FIG. 4 is a diagram showing the results of flow cytometric analysis by which binding of anti-HS6ST2 antibodies to HS6ST2_N-short_ctV5_CHO and mHS6ST2_ctV5_CHO was evaluated. Black solid lines represent anti-HS6ST2 antibodies, while gray solid lines represent mIgG1.

Clones A6, C8 and C10 bound to mHS6ST2_ctV5_CHO, but clones A1, A10, B5 and B6 did not (FIG. 4). All antibodies bound to HS6ST2_N-short_ctV5_CHO. They did not bind to the parent strain CHO DG44 cells line.

Then, the primary antibodies were serially diluted 5-fold from the concentration of 10 μg/mL in 6 steps, revealing that the anti-HS6ST2 antibodies A6 and C8 equally bound to mHS6ST2_ctV5_CHO and HS6ST2_N-short_ctV5_CHO (FIG. 5). This demonstrated that the anti-HS6ST2 antibodies A6, C8 and C10 bind to mHS6ST2, but A1, A10, B5, and B6 do not bind to it. It was also shown that A6 and C8 equally bind to HS6ST2 and mHS6ST2.

Example 4

Analysis of Epitopes of Anti-HS6ST2 Antibodies

In order to analyze epitopes of the anti-HS6ST2 antibodies prepared in Example 2, the region downstream of the transmembrane domain of HS6ST2_N-short (16 amino acids 8-23 of LLLALVMLFLFAVIVL) was divided into three parts to prepare the respective glutathione S-transferase (GST) fusion proteins. GST_HS6ST2_N, GST_HS6ST2_mid and GST_HS6ST2S are proteins containing an N-terminal GST and a C-terminal His tag added to a stretch of amino acids 24-175, a stretch of amino acids 166-317, and a stretch of amino acids 308-459 of HS6ST2_N-short, respectively. The His tag is a tag peptide consisting of six consecutive histidine residues.

In order to prepare GST_HS6ST2_N, cDNA corresponding to the stretch of amino acids 24-175 of HS6ST2_N-short was cloned into a GST fusion protein expression vector (pGEX-6P-1, GE Healthcare). PCR amplification was performed using a primer of SEQ ID NO: 21 (EcoRI recognition sequence—the 5'-end sequence of the stretch of amino acids 24-175 of HS6ST2_N-short) and a primer of SEQ ID NO: 22 (NotI recognition sequence—stop codon—His tag sequence—the 3'-end sequence of the stretch of amino acids 24-175 of HS6ST2_N-short) with pMCDN2_HS6ST2_N-short_ctV5 as a template. The amplified product was digested with EcoRI and NotI, and cloned into the EcoRI/NotI sites of pGEX-6P-1 (pGEX_GST_HS6ST2_N). Similarly, GST_HS6ST2_mid was cloned using primers of SEQ ID NO: 23 and SEQ ID NO: 24, and GST_HS6ST2_C was cloned using primers of SEQ ID NO: 25 and SEQ ID NO: 26, respectively (pGEX_GST_HS6ST2_mid, pGEX_GST_HS6ST2_C).

Then, the sequence of GST_HS6ST2_C was divided in two parts to prepare the respective GST fusion proteins. GST_HS6ST2_C1 and GST_HS6ST2_C2 are proteins containing an N-terminal GST and a C-terminal His tag added to a stretch of amino acids 308-393 and a stretch of amino acids 379-459, respectively. GST_HS6ST2_C1 was cloned using primers of SEQ ID NO: 25 and SEQ ID NO: 27 (pGEX_GST_HS6ST2_C1). GST_HS6ST2_C2 was cloned using primers of SEQ ID NO: 26 and SEQ ID NO: 28 (pGEX_GST_HS6ST2_C2).

GST_HS6ST2_N, GST_HS6ST2_mid, GST_HS6ST2_C, GST_HS6ST2_C1 and GST_HS6ST2_C2 were expressed in BL21 (DE3) Competent Cells (Takara Bio), and the whole cell lysates were resolved by SDS-PAGE electrophoresis and then transferred to PVDF membranes (Immobilon-P, Millipore) and Western blotted with the anti-HS6ST2 antibodies. The anti-HS6ST2 antibodies were used at 10 μg/mL, while the secondary antibody (HRP-anti mIgG, GE Healthcare) was used as a 3000-fold dilution, and blots were detected with ECL Western Blotting Detection Reagents (GE Healthcare). As a result, the anti-HS6ST2 antibodies A1, A10, B5, B6 and C8 bound to GST_HS6ST2_C2, A6 bound to GST_HS6ST2_C1, and C10 bound to GST_HS6ST2_N. This demonstrated that the anti-HS6ST2 antibodies A1, A10, B5, B6 and C8 bind to a stretch of amino acids 379-459, A6 binds to a stretch of amino acids 308-393, and C10 binds to a stretch of amino acids 24-175 of HS6ST2_N-short, respectively.

Example 5

Evaluation of Antibody-Dependent Cellular Cytotoxicity (ADCC) Activity of Anti-HS6ST2 Antibodies ADCC activity of the anti-HS6ST2 antibodies prepared in Example 2 was assayed. The target cells used were HS6ST2_N-short_ctV5_CHO cells. In the presence of Chromium-51 (GE Healthcare), $1 \times 10^6$ HS6ST2_N-short_ctV5_CHO cells were cultured for 1 hour. After washing, the cells were prepared at $2 \times 10^5$ cells/mL in CHO medium and added to 96-well plates at 50 μL/well. Then, each anti-HS6ST2 antibody prepared at 4 μg/mL in CHO medium or mIgG1 (BD Biosciences Pharmingen) as a negative control was added at 50 μL/well. After standing at room temperature for 15 minutes, 100 μL/well of an effector cell prepared at $5 \times 10^5$ cells/mL in CHO medium was added. The effector cell used was a recombinant cell obtained by forcibly expressing a chimeric protein containing the extracellular domain of mouse Fc-gamma receptor 3 (RefSeq Accession No. NM_010188) and the transmembrane domain and intracellular domain of human gamma-chain (RefSeq Accession No. NM_004106) in NK-92 cells (ATCC) (Japanese Patent Application No. 2007-20155, WO2008/093688). After the plates were incubated at 37° C. in a 5% $CO_2$ for 4 hours, 100 μL/well of the culture supernatants were harvested and assayed for radioactivity (cpm) using a gamma counter (1480 WIZARD 3", Wallac) to determine the specific chromium release (%) using the following equation.

$$\text{Specific chromium release (\%)} = (A-C) \times 100/(B-C)$$

where A represents radioactivity in each well, B represents the average of radioactivity in wells containing the cells lysed with Nonidet P-40 at a final concentration of 1%, and C represents the average of radioactivity in wells containing the target cells alone. B and C were assayed in triplicate, and the other was assayed in duplicate, and the average and standard deviation of the specific chromium release were calculated.

Figure 6:
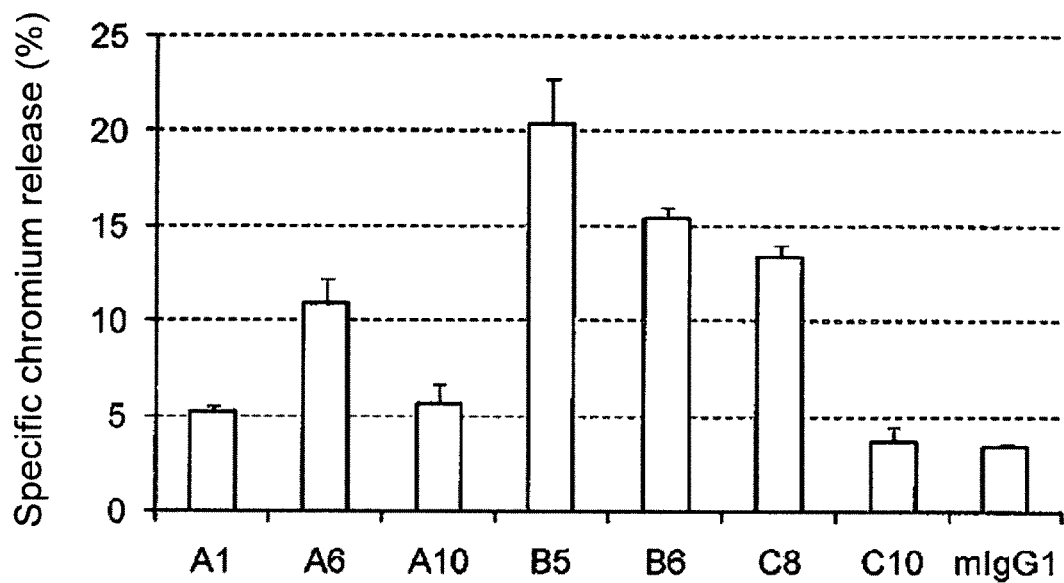
FIG. 6 is a diagram showing the results of evaluation of ADCC activity of anti-HS6ST2 antibodies against HS6ST2_N-short_ctV5_CHO.

The results showed that the anti-HS6ST2 antibodies A6, B5, B6 and C8 have ADCC activity (FIG. 6).

Example 6

Evaluation of Antitumor Activity of Anti-HS6ST2 Antibodies Using Mab-ZAP

Potential of the anti-HS6ST2 antibodies prepared in Example 2 as immunotoxins was evaluated using Mab-ZAP (Advanced Targeting Systems). Mab-ZAP is a goat anti-mouse IgG antibody conjugated to saporin. Saporin is a toxin that inhibits protein synthesis in ribosomes. When a mouse antibody that binds to an antigen on cell surfaces and Mab-ZAP are simultaneously added to a culture system, Mab-ZAP is also taken up by the cells to inhibit proliferation of the cells if the mouse antibody is taken up by the cells.

The target cells used were HS6ST2_N-short_ctV5_CHO cells. HS6ST2_N-short_ctV5_CHO cells prepared at $1 \times 10^5$ cells/mL in CHO medium were plated on 96-well plates at a density of 50 μL/well, and incubated at 37° C. in a 5% $CO_2$ incubator. On the following day, each anti-HS6ST2 antibody and Mab-ZAP were added at 100 μL/well, and incubation was continued for further 2 days. The anti-HS6ST2 antibodies were added to a final concentration of 20 ng/mL, while Mab-ZAP was added to a final concentration of 100 ng/mL. As a negative control, mIgG1 (BD Biosciences Pharmingen) was used. After incubation, 10 μL/well of a viable cell counting reagent SF (NACALAI TESQUE, INC.) was added, and after incubation for further 1.5 hours, the absorbance at 450 nm-655 nm was determined. The experiment was done in duplicate, and the average and standard deviation of the absorbance were calculated.

Figure 7:
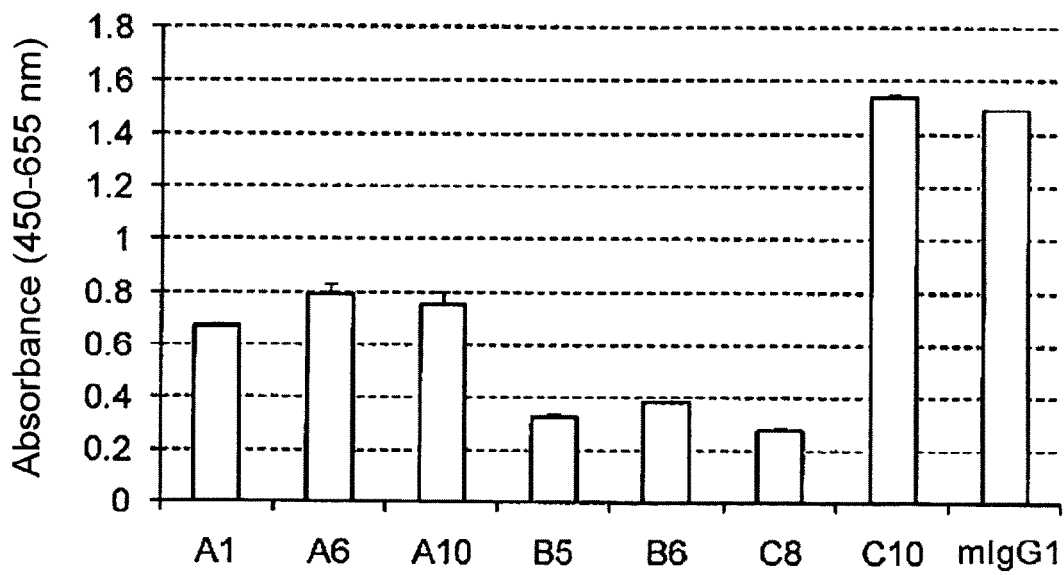
FIG. 7 is a diagram showing the results of evaluation of cytostatic activity of anti-HS6ST2 antibodies against HS6ST2_N-short_ctV5_CHO using Mab-ZAP.

All anti-HS6ST2 antibodies except for C10 inhibited cell growth in the presence of Mab-ZAP (FIG. 7). Especially, B5, B6 and C8 showed strong effects, indicating that immunotoxins targeting HS6ST2 are useful as antitumor agents.

Example 7

Evaluation of Binding Activity to HS6ST2 Variants 7-1. Cloning of an HS6ST2 Variant There exists a variant of HS6ST2 containing an N-terminal amino acid extension (UniProt Q96MM7-1, RefSeq Accession No. NM_147175). This variant designated as HS6ST2_N-long was found to bind to the anti-HS6ST2 antibodies prepared in Example 2.

The open reading frame of HS6ST2_N-short contains an NheI recognition sequence near the 5'-terminus. Thus, the previously cloned sequence of HS6ST2_N-short was used for the region downstream of this NheI recognition sequence, and the upstream sequence of HS6ST2_N-long was newly cloned. First, total RNA was isolated from the cancer cell line HuH6 (RIKEN) using Trizol (Invitrogen) following the manufacturer's protocol, and cDNA was constructed using SuperScript III Reverse Transcriptase (Invitrogen) following the manufacturer's protocol. This cDNA was used as a template with a primer of SEQ ID NO: 29 (the 5'-UTR sequence of HS6ST2_N-long) and a primer of SEQ ID NO: 30 (the sequence downstream of the NheI recognition sequence of HS6ST2_N-short) to perform PCR amplification, and the amplified product was cloned into pGEM-T Easy vector using pGEM-T Easy Vector Systems (Promega) (pGEM-T_HS6ST2_N). The PCR amplification was performed using KOD Plus Ver.2 (Toyobo) in a solution containing 5 μL of 10×KOD Plus Ver.2 buffer, 5 μL of dNTP mixture, 3 μL of 25 mM $MgSO_4$, 1 μL of the primer of SEQ ID NO: 29 (10 μM), 1 μL of the primer of SEQ ID NO: 30 (10 μM), 2 μL of HuH6 cDNA, 1 μL of KOD Plus Polymerase, and 33 μL of nuclease-free water, at 94° C. for 2 min, 35 cycles x (94° C. for 30 sec, 58° C. for 30 sec, 68° C. for 1 min), and 68° C. for 3 min. The sequence of pGEM-T_HS6ST2_N was determined to confirm that it was the same as the sequence of the relevant region of RefSeq Accession No. NM_147175.

PCR amplification was performed using pGEM-T_HS6ST2_N as a template with a primer of SEQ ID NO: 31 (EcoRI recognition sequence—Kozak sequence—the 5'-end sequence of HS6ST2_N-long) and the primer of SEQ ID NO: 30, and the amplified product was cloned into a TOPO vector using TOPO TA Cloning Kit (Invitrogen) (TOPO_HS6ST2_N). TOPO_HS6ST2_N was digested with EcoRI and NheI, and cloned into the EcoRI/NheI sites of pMCDN2_HS6ST2_N-short_ctV5 to prepare an expression vector for C-terminal V5 tagged HS6ST2_N-long (pMCDN2_HS6ST2_N-long_ctV5). The nucleotide sequence of pMCDN2_HS6ST2_N-long_ctV5 from the start codon to the stop codon is shown in SEQ ID NO: 32, and its amino acid sequence is shown in SEQ ID NO: 33.

7-2. Preparation of a CHO Cell Line Expressing HS6ST2_N-Long

The PvuI digest of pMCDN2_HS6ST2_N-long_ctV5 was transformed into the CHO DG44 cell line by electroporation. A CHO cell line stably expressing C-terminal V5 tagged HS6ST2_N-long (HS6ST2_N-long_ctV5_CHO) was established by selecting the transformed cell line with Geneticin (500 μg/mL). The culture medium used was CHO medium.

7-3. Evaluation of Binding of the Anti-HS6ST2 Antibodies to HS6ST2_N-Long

Binding activity of the anti-HS6ST2 antibodies prepared in Example 2 to HS6ST2_N-long was evaluated by flow cytometry. The cells used were HS6ST2_N-long_ctV5_CHO cells and HS6ST2_N-short_ctV5_CHO cells as a positive control, and evaluated in the same manner as in Example 3. The primary antibodies were used at a concentration of 10 μg/mL.

Figure 8:
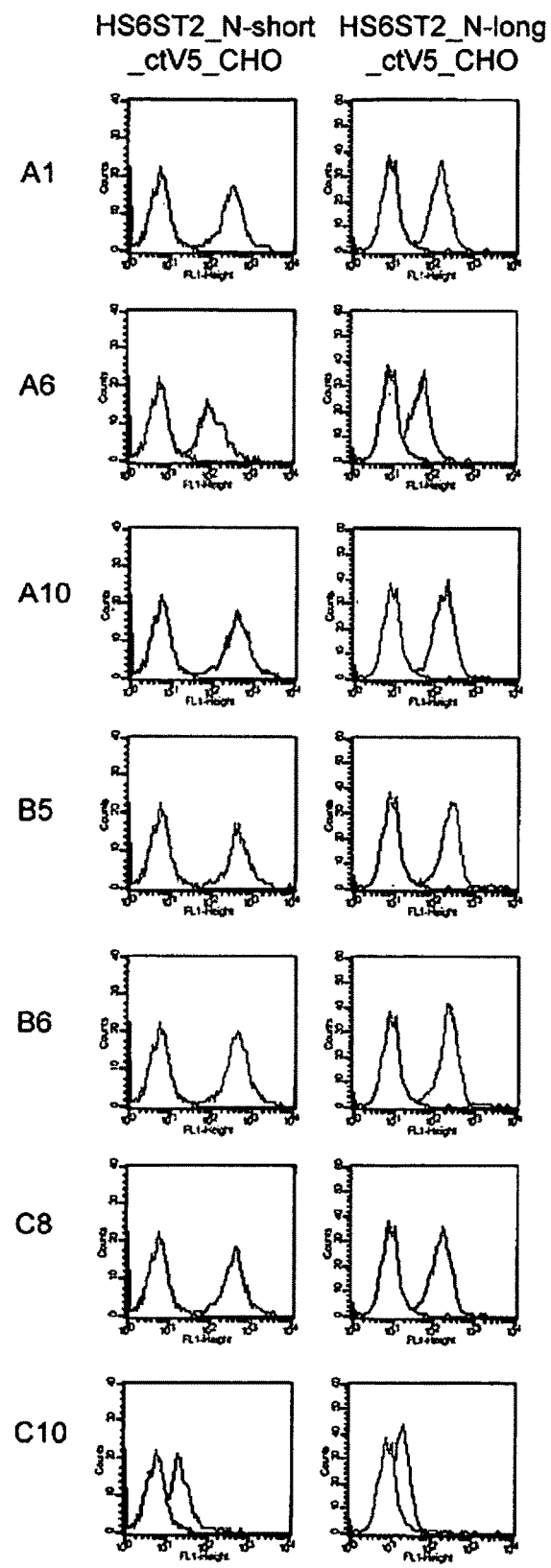
FIG. 8 is a diagram showing the results of flow cytometric analysis by which binding of anti-HS6ST2 antibodies to HS6ST2_N-short_ctV5_CHO and HS6ST2_N-long_ctV5_CHO was evaluated. Black solid lines represent anti-HS6ST2 antibodies, while gray solid lines represent mIgG1.

As a result, all antibodies equally bound to HS6ST2_N-short_ctV5_CHO cells and HS6ST2_N-long_ctV5_CHO cells, showing that they equally recognize the two variants (FIG. 8).

Example 8

Expression Analysis of HS6ST2 in Cancer Cell Lines 8-1. Expression Analysis of HS6ST2 by Flow Cytometry Using an anti-HS6ST2 antibody prepared in Example 2, the expression of HS6ST2 on the plasma membrane of cancer cell lines was analyzed by flow cytometry. The primary antibody used was the anti-HS6ST2 antibody B6 or mIgG1 (BD Biosciences Pharmingen) as a negative control, and the cells used were the lung adenocarcinoma cell line ABC-1 and the liver cancer cell line HuH6 that showed the highest expression of HS6ST2 in Human Exon 1.0 ST Array (Example 1). Flow cytometry was performed in the same manner as in Example 3, and the primary antibody was used at a concentration of 10 μg/mL. As a result, the expression of HS6ST2 was observed on the plasma membrane of both cell lines (FIG. 9).

8-2. Establishment of an HS6ST2 Detection System by Western Blotting

Western blotting using an anti-HS6ST2 antibody prepared in Example 2 was evaluated. First, $1 \times 10^6$ HS6ST2_N-short_ctV5_CHO cells and HS6ST2_N-long_ctV5_CHO cells were washed with PBS, then lysed with 100 μL of lysis buffer (50 mM Tris-HCl, pH7.4, 150 mM NaCl, 1 mM EDTA, 1% Triton X-100, Protease Inhibitor Cocktail (Sigma)) to prepare whole cell lysates. They were treated with N-Glycosidase F (PNGaseF, New England Biolabs) to remove N-glycans. The samples were resolved by SDS-PAGE electrophoresis using Multigel II Mini (8/16, COSMO BIO), then transferred to PVDF membranes (Immobilon-P, Millipore) and Western blotted with the anti-HS6ST2 antibody C10 or anti-V5 tag antibody (Invitrogen). The anti-HS6ST2 antibody C10 was used at 5 μg/mL and the anti-V5 tag antibody was used as a 1:5000 dilution, and reacted at room temperature for 1 hour. An HRP-conjugated anti-mouse IgG antibody (GE Healthcare) was used as a secondary antibody, and reacted at room temperature for 1 hour. Finally, bands were detected by color development with ECL Western Blotting Detection Reagents (GE Healthcare) followed by exposure to X-ray film.

Figure 10:
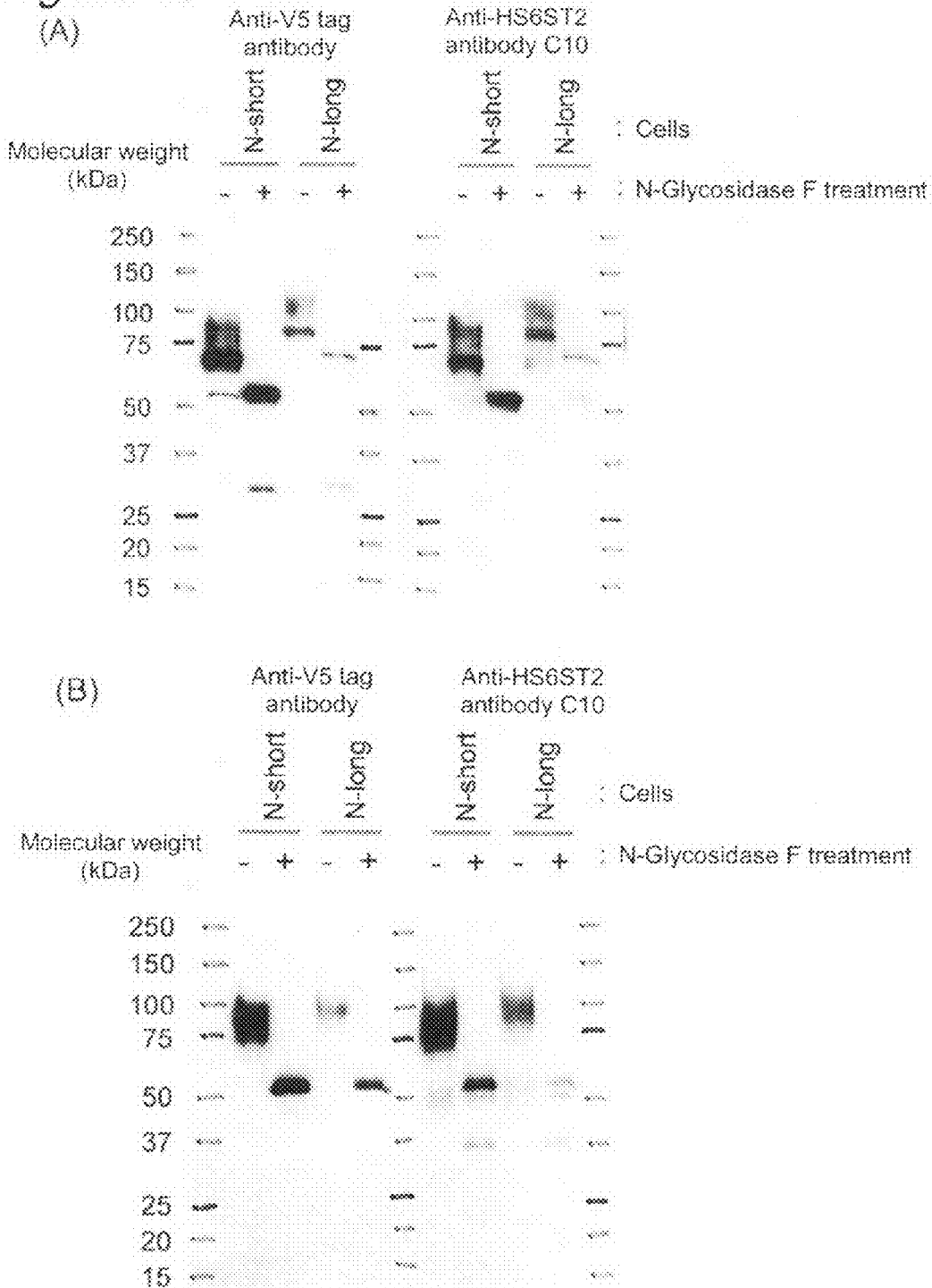
FIG. 10 is a diagram showing the results of Western blotting of HS6ST2_N-short_ctV5_CHO and HS6ST2_N-long_ctV5_CHO using the anti-HS6ST2 antibody C10 and anti-V5 tag antibody. The whole cell lysates (A) or culture supernatants (B) of HS6ST2_N-short_ctV5_CHO(N-short) or HS6ST2_N-long_ctV5_CHO(N-long) were used as samples to compare the results in the presence and absence of N-Glycosidase F treatment.

The molecular weights of HS6ST2_N-short_ctV5 and HS6ST2_N-long_ctV5 deduced from their amino acid sequences are 55 kDa and 71 kDa, respectively. Bands of the deduced molecular weights appeared after N-glycans were removed by N-Glycosidase F (FIG. 10A). The anti-HS6ST2 antibody C10 showed similar bands to those of the anti-V5 tag antibody, indicating that it can be used for Western blotting.

Then, soluble HS6ST2 secreted in the culture supernatants of HS6ST2_N-short_ctV5_CHO cells and HS6ST2_N-long_ctV5_CHO cells was detected by Western blotting. When the culture supernatants of HS6ST2_N-short_ctV5_CHO cells and HS6ST2_N-long_ctV5_CHO cells were treated with N-Glycosidase F, and Western blotted with the anti-HS6ST2 antibody C10 and anti-V5 tag antibody, bands appeared around 50-60 kDa (FIG. 10B). HS6ST2_N-short and HS6ST2_N-long showed the same molecular weight, suggesting that both were cleaved at the same site. The fact that they are secreted suggested the possibility of cleavage downstream of the transmembrane domain (16 amino acids of LLLALVMLFLFAVIVL at residues 8-23 or 154-169 from the N-terminus of HS6ST2_N-short or HS6ST2_N-long). HS6ST1 is also known to be cleaved downstream of the transmembrane domain (Molecular characterization and expression of heparan-sulfate 6-sulfotransferase. J Biol. Chem. 1998. 273:9208).

8-3. Expression Analysis of HS6ST2 by Western Blotting

The expression of HS6ST2 in lung adenocarcinoma cell lines and an ovarian cancer cell line and the molecular weight of the expressed protein, and its secretion into culture supernatants were determined by Western blotting using the anti-HS6ST2 antibody C10. Whole cell lysates prepared from the lung adenocarcinoma cell lines A549 and ABC-1 (both from JCRB Cell Bank) as well as NCI-H441 and NCI-H1781 (both from ATCC), and the ovarian cancer cell line OVMANA (JCRB Cell Bank) were treated with N-Glycosidase F, and Western blotted. The protein content of the whole cell lysates was determined by DC Protein Assay Kit I (Bio-Rad) after they were run at 15 μg/lane except for A549 at 10 μg/lane. As a result, HS6ST2 was expressed in the lung adenocarcinoma cell lines ABC-1, NCI-H441 and NCI-H1781 and the ovarian cancer cell line OVMANA (FIG. 11A). All of them showed a molecular weight of 50-60 kDa after N-Glycosidase F treatment, suggesting that they correspond to the N-short variant. A549 was used as a negative control because it is a cell line that was shown not to express HS6ST2 in Example 1.

Then, HS6ST2 in the culture supernatants of these cells was assayed. The culture supernatants were filtered through a 0.22 μm filter, then concentrated to 1:50 using Amicon Ultra (10 kDa cut, Millipore) and used for Western blotting (FIG. 11B). To prevent the influence of protein contained in FBS, the cancer cell lines cultured in 10-cm Petri dishes were incubated overnight in a FBS-free medium (5 mL) and the resulting culture supernatants were used. As a result, soluble HS6ST2 was detected in the culture supernatants of the cancer cell lines, indicating that soluble HS6ST2 can be a potential diagnostic marker for cancer. The cells remaining after harvesting the culture supernatants were lysed with lysis buffer and the protein content was determined by DC Protein Assay Kit I (Bio-Rad) to show that the protein levels per dish in A549, ABC-1, NCI-H441, NCI-1781 and OVMANA were 1.4, 2.1, 1.8, 1.9 and 2.0 mg, respectively and that the number of cells was nearly equal.

Example 9

Figure 12:
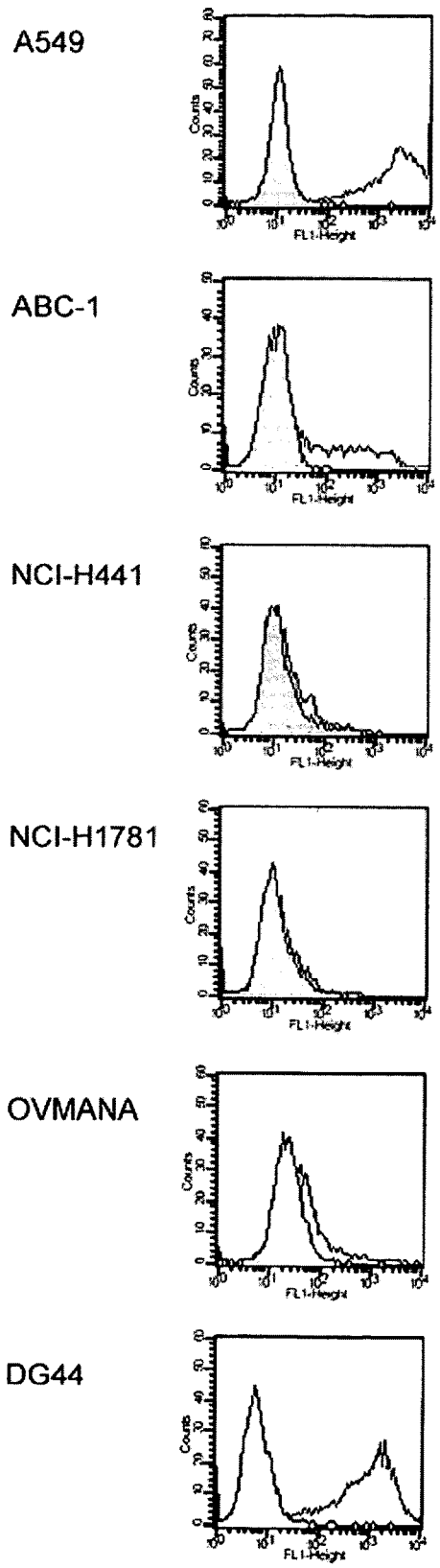
FIG. 12 is a diagram showing the results of flow cytometric analysis by which the expression of heparan sulfate on the plasma membrane was evaluated. Black solid lines represent an anti-heparan sulfate antibody, while gray solid lines represent mIgM.

Binding of Soluble HS6ST2 to Heparan Sulfate and Anti-Tumor Effects of Anti-HS6ST2 Antibodies 9-1. Binding of Soluble HS6ST2 to Heparan Sulfate It was demonstrated that soluble HS6ST2 secreted from cells binds to heparan sulfate on the plasma membrane. First, the expression of heparan sulfate on the plasma membrane was evaluated by flow cytometry in the same manner as in Example 3. The cells used were the lung adenocarcinoma cell lines A549, ABC-1, NCI-H441 and NCI-H1781, the ovarian cancer cell line OVMANA and the CHO DG44 cell line. An anti-heparan sulfate antibody (HepSS-1, SEIKAGAKU BIOBUSINESS CORPORATION) was used as a primary antibody and mouse IgM (mIgM, BD Biosciences Pharmingen) was used as a negative control at a concentration of 20 μg/mL (NCI-H441, NCI-H1781) or 40 μg/mL (A549, ABC-1, OVMANA, DG44). As a result, A549, ABC-1 and DG44 were shown to express heparan sulfate (FIG. 12).

Figure 13:
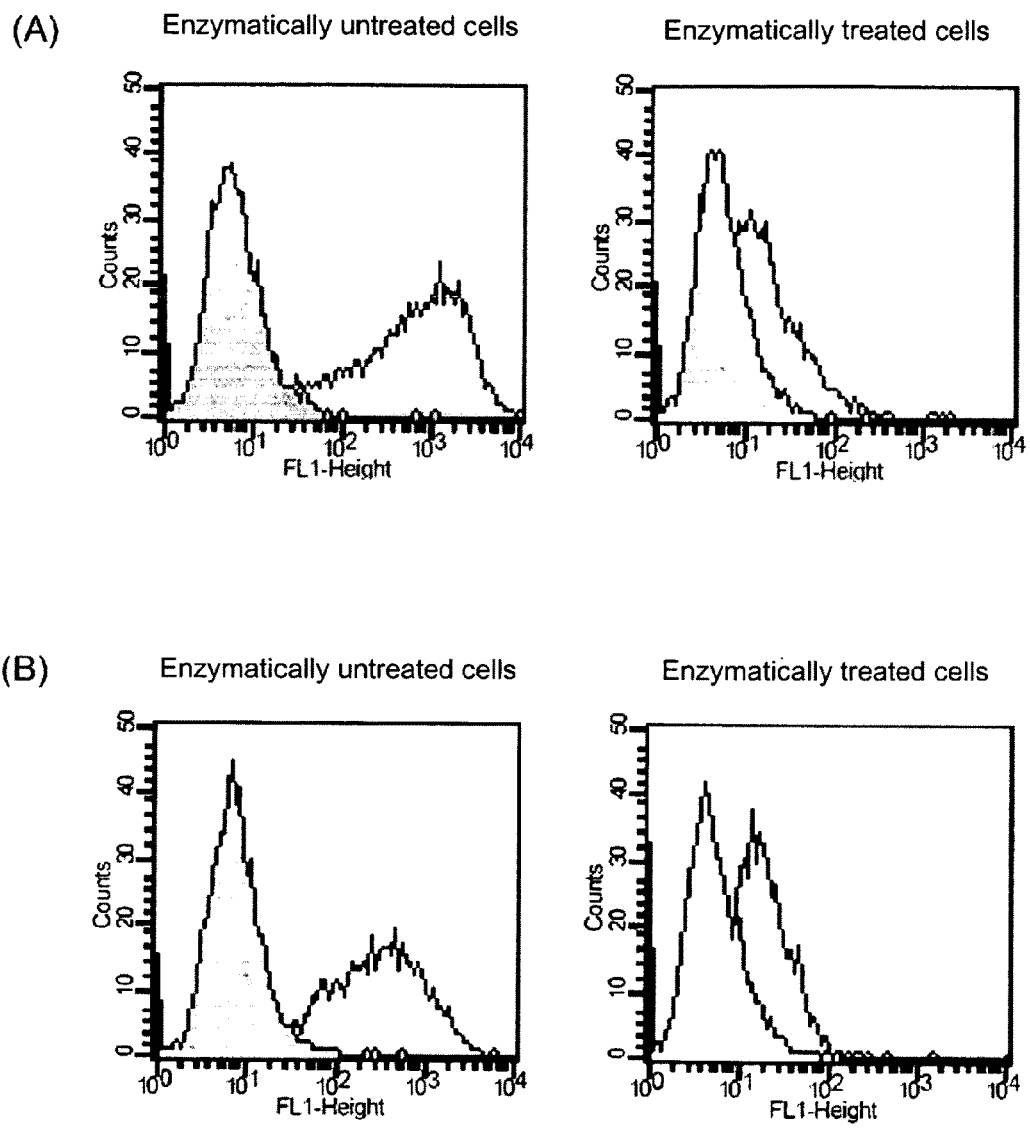
FIG. 13 is a diagram showing the results of flow cytometric analysis by which binding of sHS6ST2_FLAG to heparan sulfate was evaluated. In (A), heparan sulfate in DG44 cells was enzymatically degraded and the expression level of heparan sulfate was compared in the presence and absence of the enzymatic treatment. Black solid lines represent an anti-heparan sulfate antibody, while gray solid lines represent mIgM. In (B), binding of sHS6ST2_FLAG to DG44 cells was compared in the presence and absence of the enzymatic treatment. Black solid lines represent the anti-HS6ST2 antibody C8, while gray solid lines represent mIgG1.

Then, heparan sulfate on the plasma membrane was enzymatically degraded to evaluate binding of soluble HS6ST2 to cells. $1 \times 10^6$ DG44 cells were cultured in 3 mL of CHO-S-SFM II medium containing 1 mU/mL heparinase, heparitinase I and heparitinase II (all from SEIKAGAKU BIOBUSINESS CORPORATION), HT supplement, and penicillin/streptomycin at 37° C. for 2 hours. Heparinase, heparitinase I and heparitinase II are enzymes that specifically degrade heparan sulfate. The expression of heparan sulfate significantly decreased in enzymatically treated cells (FIG. 13A).

Then, binding of soluble HS6ST2 (sHS6ST2_FLAG) to DG44 cells was evaluated. DG44 cells were enzymatically treated, and then reacted with sHS6ST2_FLAG prepared at 50 μg/mL in FACS buffer at 4° C. for 3 hours. After washing, the cells were analyzed by flow cytometry in the same manner as in Example 3. The anti-HS6ST2 antibody C8 was used as a primary antibody and mIgG1 (BD Biosciences Pharmingen) was used as a negative control. As a result, sHS6ST2_FLAG bound to enzymatically untreated DG44 cells but scarcely bound to enzymatically treated DG44 cells, showing that sHS6ST2_FLAG specifically binds to heparan sulfate (FIG. 13B).

9-2. Evaluation of Binding of Soluble HS6ST2 to Cancer Cells and Anti-Tumor Activity Using Mab-ZAP Binding of sHS6ST2_FLAG to the lung adenocarcinoma cell line A549 that showed high expression of heparan sulfate was evaluated. A549 cells were reacted with 100, 20, 4, 0.8, and 0 μg/mL of sHS6ST2_FLAG on ice for 2 hours, and then analyzed by flow cytometry, revealing concentration-dependent binding of sHS6ST2_FLAG (FIG. 14A).

Then, antitumor activity of an anti-HS6ST2 antibody targeting sHS6ST2_FLAG bound to A549 cells was assayed in the presence of Mab-ZAP. A549 cells were prepared at a density of $1 \times 10^4$ cells/mL in DMEM medium (Invitrogen) containing 10% FBS and penicillin/streptomycin, and plated on 96-well plates at 50 μL/well. Here, wells containing 50 μg/mL sHS6ST2_FLAG or not were prepared. After incubation at 37° C. in 5% $CO_2$ incubator for 1 day, the culture supernatants were removed and the anti-HS6ST2 antibody C8 and Mab-ZAP were added to 100 μL/well. C8 was added at final concentrations of 500, 100, 20, 4, and 0 ng/mL, and Mab-ZAP was added at a final concentration of 500 ng/mL. After incubation for further 3 days, 10 μL/well of a viable cell counting reagent SF (NACALAI TESQUE, INC.) was added, and after incubation for 4 hours, the absorbance at 450 nm-655 nm was determined. The experiment was done in duplicate, and the average and standard deviation of the absorbance were calculated. As a result, the growth of sHS6ST2_FLAG-bound cells was inhibited by the anti-HS6ST2 antibody C8 in a concentration-dependent manner (FIG. 14B). Consequently, it was demonstrated that the anti-HS6ST2 antibody shows antitumor effects targeting soluble HS6ST2.

Example 10

Determination of Soluble HS6ST2 by ELISA

In view of the potential of soluble HS6ST2 as a diagnostic marker for cancer as suggested from its secretion by cancer cell lines in Example 8, an ELISA system for detecting soluble HS6ST2 was constructed. The anti-HS6ST2 antibodies A6, B5 and C8 were used. B5 and C8 bind to a stretch of amino acids 379-459, and A6 binds to a stretch of amino acids 308-393 of HS6ST2_N-short (Example 4). Further, C8 binds to mHS6ST2, but B5 does not (Example 3). Thus, the three antibodies seemed to bind at different sites.

Figure 15:
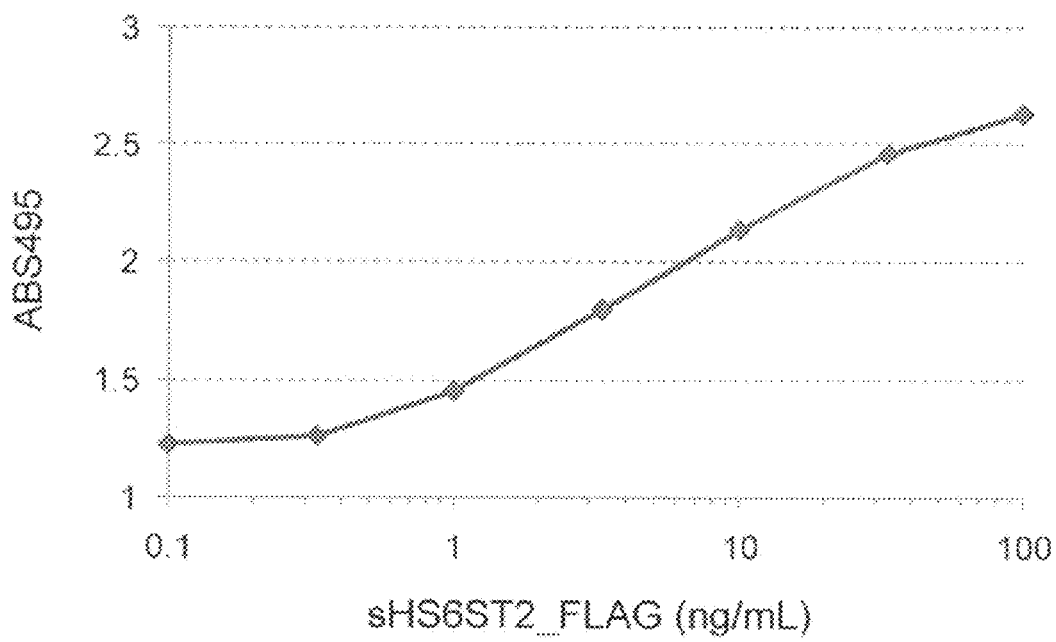
FIG. 15 is a diagram showing a calibration curve of an ELISA system by which soluble HS6ST2 is detected.

First, the anti-HS6ST2 antibodies B5 and C8 were biotinylated (B5-biotin, C8-biotin) by using Biotin Protein Labeling Kit (Roche) following the manufacturer's protocol. The concentrations of the biotinylated antibodies were determined by using DC Protein Assay Kit I (Bio-Rad). The anti-HS6ST2 antibody A6 was prepared at 5 µg/mL in coating buffer (0.1M $NaHCO_3$, pH9.6, 0.02% $NaN_3$), and added to 96-well plates for ELISA (F96 Cert. Maxisorp, Nunc) at 100 µL/well. The antibody was bound to the plates by standing at room temperature for 1 hour. After the supernatants were removed, 200 µL/well of dilution buffer (50 mM Tris-HCl, pH8.1, 150 mM NaCl, 1 mM $MgCl_2$, 0.05% Tween 20, 1% bovine serum albumin, 0.02% $NaN_3$) was added and the plates were blocked by standing at room temperature for 1 hour. After the supernatants were removed, 50 µL/well of each sample was added and the mixture was reacted at room temperature for 1 hour. The samples used were culture supernatants of the lung adenocarcinoma cell line ABC-1 and culture supernatants of HS6ST2_N-short_ctV5_CHO cells diluted 1:500 in RPMI1640 medium containing 10% FBS. After the plates were washed three times with rinse buffer (50 mM Tris-HCl, pH7.6, 150 mM NaCl, 0.05% Tween 20), 100 µL/well of dilution buffer containing 3 µg/mL B5-biotin and 3 µg/mL C8-biotin was added, and the mixture was reacted at room temperature for 1 hour. After the plates were washed three times with rinse buffer, 100 µL/well of streptavidin-conjugated alkaline phosphatase (ZyMax Streptavidin-AP, Invitrogen) diluted 1:1000 in dilution buffer was added and the mixture was reacted at room temperature for 1 hour. After the plates were washed three times with rinse buffer, ELISA Amplification System (Invitrogen) was used for color development following the manufacturer's protocol and the absorbance at 495 nm was determined. A calibration curve was prepared using sHS6ST2_FLAG diluted with 10% FBS-RPMI1640 medium. The results of ELISA showed that the concentrations of soluble HS6ST2 in the culture supernatants of the lung adenocarcinoma cell line ABC-1 and HS6ST2_N-short_ctV5_CHO cells were 9.5 ng/mL and 1.8 µg/mL, respectively. The calibration curve is shown in FIG. 15.

Figure 16:
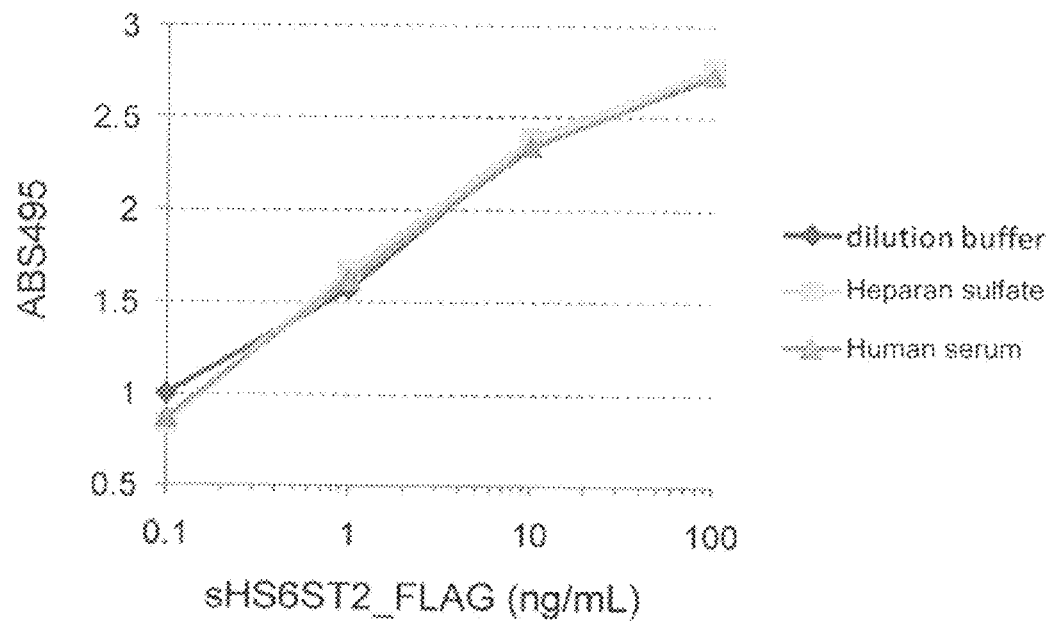
FIG. 16 is a diagram showing that heparan sulfate or human serum does not influence the ELISA system.

Diagnostic markers for cancer can preferably be measured by using peripheral blood. The presence of heparan sulfate in blood (Soluble syndecan-1 and serum basic fibroblast growth factor are new prognostic factors in lung cancer. Cancer Res 62:5210 (2002), Serum and urinary concentrations of heparan sulfate in patients with diabetic nephropathy. Kidney Int 56:650 (1999), Isolation and characterization of glycosaminoglycans in human plasma. J Clin Invest 76:1984 (1985)) implied that soluble HS6ST2 might bind to heparan sulfate in blood to inhibit detection by ELISA. Thus, ELISA was evaluated in the presence of human serum or heparan sulfate. sHS6ST2_FLAG was prepared at 1 µg/mL in dilution buffer, or dilution buffer containing 100 µg/mL heparan sulfate (SEIKAGAKU BIOBUSINESS CORPORATION) or human serum (COSMO BIO), and allowed to stand at room temperature for 1 hour. Then, it was serially diluted 10-fold in dilution buffer from 100 ng/mL in 4 steps and assayed by ELISA, revealing color development even in the presence of heparan sulfate or human serum (FIG. 16). This demonstrated that the established ELISA system is not influenced by human serum.

Example 11

Analysis of the Expression of HS6ST2 in Lung Cancer by Immunohistochemical Staining In view of the increased expression of the HS6ST2 gene in lung adenocarcinoma (Example 1), the expression of the HS6ST2 protein in lung cancer was analyzed by immunohistochemical staining. Each specimen was fixed in 4% paraformaldehyde and embedded in a paraffin block by the AMeX method, from which 5 µm sections were prepared. These sections were immunohistochemically stained with Ventana HX Discovery System (Ventana Medical Systems) as follows. Each section was deparaffinized and then washed, and heated at 100° C. for 30 minutes using Cell Conditioner #1 (Ventana Medical Systems), and then reacted with 3.0% hydrogen peroxide solution (Inhibitor D, Ventana Medical Systems) at 37° C. for 4 minutes to remove endogenous peroxidase. After washing, Protein Block (Dako) was added, and the mixture was reacted at room temperature for 30 minutes to remove non-specific reactions. After washing, 25 µg/mL of the anti-HS6ST2 antibody C10 was added as a primary antibody and the mixture was reacted at room temperature for 2 hours. After washing, a secondary antibody (Ventana Universal Secondary Antibody, Ventana Medical Systems) was added and the mixture was reacted at room temperature for 30 minutes. After washing, Blocker D (Ventana Medical Systems) was added and the mixture was reacted at room temperature for 2 minutes to remove non-specific reactions, after which streptavidin horseradish peroxidase (Ventana Medical Systems) was added and the mixture was reacted at 37° C. for 16 minutes. After washing, a mixture of diaminobenzidine (DAB map solution, Ventana Medical Systems) and hydrogen peroxide solution (DAB map solution, Ventana Medical Systems) was added and reacted at 42° C. for 8 minutes for color development of the substrate. Further, color development was enhanced with Copper sulfate solution (Ventana Medical Systems). Further washing was followed by nuclear staining with hematoxylin, dehydration, penetration and encapsulation.

Figure 17:
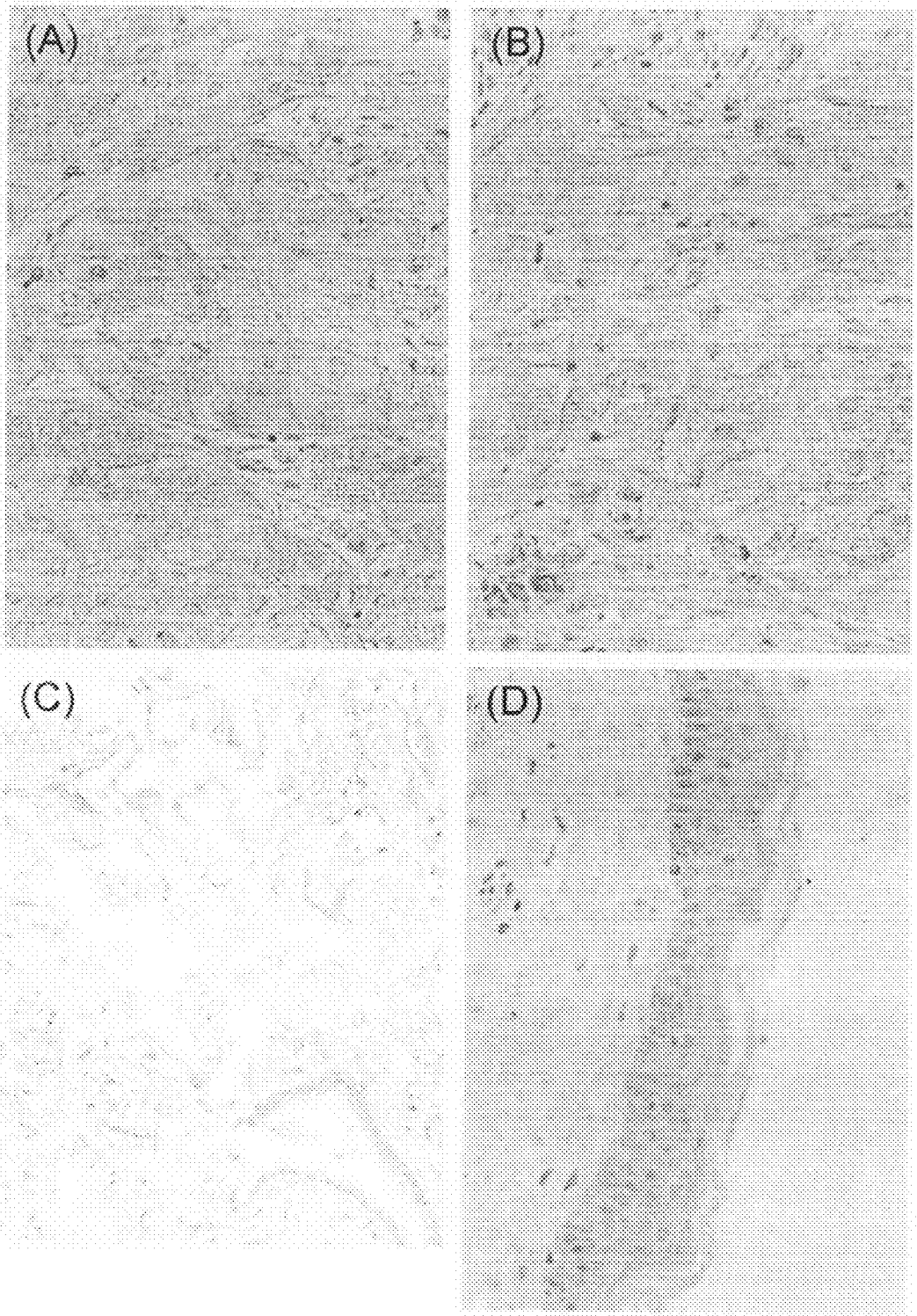
FIG. 17 is a diagram showing the results of immunohistochemical staining by which the expression of the HS6ST2 protein was analyzed in clinical lung adenocarcinoma (A), clinical squamous cell lung carcinoma (B), normal tissue adjacent to lung cancer (C), and skin (D).

As a result of immunohistochemical staining, positive responses were observed in the cytoplasm and the plasma membrane in 10 of 10 cases of clinical lung adenocarcinoma samples and 8 of 8 cases of clinical squamous cell lung carcinoma samples. Positive responses were observed in the cytoplasm and the plasma membrane in macrophages and bronchial epithelial cells from normal lung tissues. Positive responses were observed in the cytoplasm in lung vascular endothelial cells. Positive responses were observed in the cytoplasm in epithelial cells of skin, glandular cells of pituitary gland and tubular epithelium of kidney from normal organs other than lung (testis, endometrium, skin, ovary, heart, bladder, liver, cerebral cortex, cervix, spleen, bone marrow, thymus, lymph node, adrenal gland, thyroid, pituitary gland, pancreas, breast, stomach, large intestine, kidney, prostate) (FIG. 17). Thus, HS6ST2 is located at very high frequency in the plasma membrane in clinical lung adenocarcinoma and clinical squamous cell lung carcinoma, suggesting that it is promising as a target molecule of antibody drugs. Macrophages and bronchial epithelial cells of lung are known to express heparan sulfate (Heterogeneity of heparan sulfates in human lung. Am J Respir Cell Mol. Biol. 2004. 30:166), implying the possibility that soluble HS6ST2 secreted from cancer cells might have bound to it.

Example 12

Determination of the Gene Sequences of the Variable Regions of Anti-HS6ST2 Antibodies The nucleic acid sequences and amino acid sequences of the variable regions of the anti-HS6ST2 antibodies prepared in Example 2 were determined. Total RNA was purified from 1×10⁶ hybridoma cells producing each antibody by using Trizol (Invitrogen) following the manufacturer's protocol. One µg is of total RNA was used with SMART RACE cDNA Amplification Kit (Clontech), a synthetic oligonucleotide MHC-IgG1 (SEQ ID NO: 34) complementary to the mouse IgG1 constant region sequence, and a synthetic oligonucleotide MLC-kappa (SEQ ID NO: 35) complementary to the mouse κ chain constant region sequence to amplify by PCR sequences from the sites corresponding to the oligonucleotide sequences to the 5'-cDNA ends of the heavy and light chain cDNAs of the antibody. The amplified products were cloned into pGEM-T Easy vector using pGEM-T Easy Vector Systems (Promega) to determine the cDNA sequences. The sequence ID numbers of the variable region sequences of the antibodies were listed in the table below.

TABLE 1

| Antibody | | Nucleotide sequence (SEQ ID NO) | Amino acid sequence (SEQ ID NO) |
|---|---|---|---|
| A1 | Heavy chain variable region | 36 | 37 |
|  | Light chain variable region | 38 | 39 |
| A6 | Heavy chain variable region | 40 | 41 |
|  | Light chain variable region | 42 | 43 |
| A10 | Heavy chain variable region | 44 | 45 |
|  | Light chain variable region | 46 | 47 |
| B5 | Heavy chain variable region | 48 | 49 |
|  | Light chain variable region | 50 | 51 |
| B6 | Heavy chain variable region | 52 | 53 |
|  | Light chain variable region | 54 | 55 |
| C8 | Heavy chain variable region | 56 | 57 |
|  | Light chain variable region | 58 | 59 |
| C10 | Heavy chain variable region | 60 | 61 |
|  | Light chain variable region | 62 | 63 |

The amino acid sequences of the CDRs of these variable regions are shown in the table below.

TABLE 2

| Antibody | | | Amino acid sequence | SEQ ID NO |
|---|---|---|---|---|
| A1 | Heavy chain | CDR1 | YYWLG | 64 |
|  |  | CDR2 | DIYPGSGNTYYNEKFKG | 65 |
|  |  | CDR3 | RAYYYNQVFFDH | 66 |
|  | Light chain | CDR1 | KASENVVTYVS | 67 |
|  |  | CDR2 | GASNRYT | 68 |
|  |  | CDR3 | GQGYSYPYT | 69 |
| A6 | Heavy chain | CDR1 | DYYMH | 70 |
|  |  | CDR2 | WIDPENDDTEYAPKFQG | 71 |
|  |  | CDR3 | GYYGSGFAY | 72 |
|  | Light chain | CDR1 | KSSQSLLNSGNQKNYLT | 73 |
|  |  | CDR2 | WASIRES | 74 |
|  |  | CDR3 | QNDYSYPLT | 75 |
| A10 | Heavy chain | CDR1 | DTYMH | 76 |
|  |  | CDR2 | RIDPANGNTKFDPKFQG | 77 |
|  |  | CDR3 | NLLRAMDY | 78 |
|  | Light chain | CDR1 | KSSQSLLYSSNQKNYLA | 79 |
|  |  | CDR2 | WASTRES | 80 |
|  |  | CDR3 | LQYFTYPFT | 81 |
| B5 | Heavy chain | CDR1 | RYAMS | 82 |
|  |  | CDR2 | SIVSGDKTYYPDSVKG | 83 |
|  |  | CDR3 | ELGYFDV | 84 |
|  | Light chain | CDR1 | RSSQSLVHSNGNTYLH | 85 |
|  |  | CDR2 | KVSNRFS | 86 |
|  |  | CDR3 | SQSIHVPPLT | 87 |
| B6 | Heavy chain | CDR1 | DYYMH | 88 |
|  |  | CDR2 | WIDPDNGDTEYAPKFQG | 89 |
|  |  | CDR3 | GNGNYWFAY | 90 |
|  | Light chain | CDR1 | RSSQSLVHSNGNTYLH | 91 |
|  |  | CDR2 | KVSNRFS | 92 |
|  |  | CDR3 | SQTTLVPYT | 93 |

TABLE 3

| | | | | |
|---|---|---|---|---|
| C8 | Heavy chain | CDR1 | DYYMH | 94 |
|  |  | CDR2 | WIDPDNDDTEYAPKFQG | 95 |
|  |  | CDR3 | GNGNYWFAY | 96 |
|  | Light chain | CDR1 | RSSQSLVHSNGNTYLH | 97 |
|  |  | CDR2 | KVSNRFS | 98 |
|  |  | CDR3 | SQTTLVPYT | 99 |
| C10 | Heavy chain | CDR1 | DSWMH | 100 |
|  |  | CDR2 | EIRPNSGKTNYNEKFKG | 101 |
|  |  | CDR3 | TYMSHFDY | 102 |
|  | Light chain | CDR1 | RSSKSLLHSNGITYLY | 103 |
|  |  | CDR2 | QMSNLAP | 104 |
|  |  | CDR3 | AQNLELPFT | 105 |

The invention claimed is:

1. An isolated monoclonal antibody that binds to an HS6ST2 protein wherein said antibody recognizes amino acids 308-459 of an HS6ST2 protein having an amino acid sequence of SEQ ID NO: 107.

2. The isolated monoclonal antibody of claim 1 which has cytotoxic activity.

3. The isolated monoclonal antibody of claim 1 which is conjugated to a cytotoxic agent.

4. The isolated monoclonal antibody of claim 1 which binds to HS6ST2 bound to heparan sulfate.

5. The isolated monoclonal antibody of claim 1 which binds to HS6ST2 expressed on the plasma membrane.

6. The isolated monoclonal antibody of claim 1 characterized in that it is any one of the following antibodies: (1) an antibody (A1) comprising a heavy chain variable region including a heavy chain CDR1 having the amino acid sequence of SEQ ID NO: 64, a heavy chain CDR2 having the amino acid sequence of SEQ ID NO: 65, and a heavy chain CDR3 having the amino acid sequence of SEQ ID NO: 66; (2) an antibody (A6) comprising a heavy chain variable region including a heavy chain CDR1 having the amino acid sequence of SEQ ID NO: 70, a heavy chain CDR2 having the amino acid sequence of SEQ ID NO: 71, and a heavy chain CDR3 having the amino acid sequence of SEQ ID NO: 72; (3) an antibody (A10) comprising a heavy chain variable region including a heavy chain CDR1 having the amino acid sequence of SEQ ID NO: 76, a heavy chain CDR2 having the amino acid sequence of SEQ ID NO: 77, and a heavy chain CDR3 having the amino acid sequence of SEQ ID NO: 78; (4) an antibody (B5) comprising a heavy chain variable region including a heavy chain CDR1 having the amino acid sequence of SEQ ID NO: 82, a heavy chain CDR2 having the amino acid sequence of SEQ ID NO: 83, and a heavy chain CDR3 having the amino acid sequence of SEQ ID NO: 84; (5) an antibody (B6) comprising a heavy chain variable region including a heavy chain CDR1 having the amino acid sequence of SEQ ID NO: 88, a heavy chain CDR2 having the amino acid sequence of SEQ ID NO: 89, and a heavy chain CDR3 having the amino acid sequence of SEQ ID NO: 90; (6) an antibody (C8) comprising a heavy chain variable region including a heavy chain CDR1 having the amino acid sequence of SEQ ID NO: 94, a heavy chain CDR2 having the amino acid sequence of SEQ ID NO: 95, and a heavy chain CDR3 having the amino acid sequence of SEQ ID NO: 96; (7) an antibody (A1) comprising a light chain variable region including a light chain CDR1 having the amino acid sequence of SEQ ID NO: 67, a light chain CDR2 having the amino acid sequence of SEQ ID NO: 68, and a light chain CDR3 having the amino acid sequence of SEQ ID NO: 69; (8) an antibody (A6) comprising a light chain variable region including a light chain CDR1 having the amino acid sequence of SEQ ID NO: 73, a light chain CDR2 having the amino acid sequence of SEQ ID NO: 74, and a light chain CDR3 having the amino acid sequence of SEQ ID NO: 75; (9) an antibody (A10) comprising a light chain variable region including a light chain CDR1 having the amino acid sequence of SEQ ID NO: 79, a light chain CDR2 having the amino acid sequence of SEQ ID NO: 80, and a light chain CDR3 having the amino acid sequence of SEQ ID NO: 81; (10) an antibody (B5) comprising a light chain variable region including a light chain CDR1 having the amino acid sequence of SEQ ID NO: 85, a light chain CDR2 having the amino acid sequence of SEQ ID NO: 86, and a light chain CDR3 having the amino acid sequence of SEQ ID NO: 87; (11) an antibody (B6) comprising a light chain variable region including a light chain CDR1 having the amino acid sequence of SEQ ID NO: 91, a light chain CDR2 having the amino acid sequence of SEQ ID NO: 92, and a light chain CDR3 having the amino acid sequence of SEQ ID NO: 93; (12) an antibody (C8) comprising a light chain variable region including a light chain CDR1 having the amino acid sequence of SEQ ID NO: 97, a light chain CDR2 having the amino acid sequence of SEQ ID NO: 98, and a light chain CDR3 having the amino acid sequence of SEQ ID NO: 99; (13) an antibody (A1) comprising the heavy chain variable region of (1) and the light chain variable region of (8); (14) an antibody (A6) comprising the heavy chain variable region of (2) and the light chain variable region of (9); (15) an antibody (A10) comprising the heavy chain variable region of (3) and the light chain variable region of (10); (16) an antibody (B5) comprising the heavy chain variable region of (4) and the light chain variable region of (11); (17) an antibody (B6) comprising the heavy chain variable region of (5) and the light chain variable region of (12); (18) an antibody (C8) comprising the heavy chain variable region of (6) and the light chain variable region of (13); (19) an antibody that binds to the same epitope of an HS6ST2 protein as the antibody of any one of (1) to (18) binds to.

7. The isolated antibody of claim 1 which recognizes amino acids 379-459, or amino acids 308-393 of an HS6ST2 protein having the amino acid sequence of SEQ ID NO: 107.

8. A pharmaceutical composition comprising the isolated antibody of claim 1 as an active ingredient.

9. The pharmaceutical composition of claim 8, which is an anticancer agent.

* * * * *

SEQUENCE LISTING

<160> NUMBER OF SEQ ID NOS: 116

<210> SEQ ID NO 1
<211> LENGTH: 23
<212> TYPE: DNA
<213> ORGANISM: Artificial
<220> FEATURE:
<223> OTHER INFORMATION: A nucleotide sequence of a forward primer for cloning of HS6ST2_N-short (HS6ST-8, p54).

<400> SEQUENCE: 1
atggatgaga aatccaacaa gct                                          23

<210> SEQ ID NO 2

```
<211> LENGTH: 22
<212> TYPE: DNA
<213> ORGANISM: Artificial
<220> FEATURE:
<223> OTHER INFORMATION: A nucleotide sequence of a reverse primer for
      cloning of HS6ST2_N-short (HS6ST2-2, p33).

<400> SEQUENCE: 2
acgccatttc tctacactgc ct                                              22

<210> SEQ ID NO 3
<211> LENGTH: 94
<212> TYPE: DNA
<213> ORGANISM: Artificial
<220> FEATURE:
<223> OTHER INFORMATION: A partial nucleotide sequence of pMCDN2_ctV5
      expression vector.

<400> SEQUENCE: 3
gaattccacc atggctagcg tcgactacag cggccgcggt aagcctatcc ctaaccctct     60
cctcggtctc gattctacgc gtaccggtta gtaa                                 94

<210> SEQ ID NO 4
<211> LENGTH: 35
<212> TYPE: DNA
<213> ORGANISM: Artificial
<220> FEATURE:
<223> OTHER INFORMATION: A nucleotide sequence of a forward primer for
      pMCDN2_HS6ST2_N-short_ctV5 (HS6ST2-9, p65).

<400> SEQUENCE: 4
cctgaattcc accatggatg agaaatccaa caagc                                35

<210> SEQ ID NO 5
<211> LENGTH: 34
<212> TYPE: DNA
<213> ORGANISM: Artificial
<220> FEATURE:
<223> OTHER INFORMATION: A nucleotide sequence of a reverse primer for
      pMCDN2_HS6ST2_N-short_ctV5 (HS6ST2-10, p65).

<400> SEQUENCE: 5
tttgcggccg ctacgccatt tctctacact gcct                                 34

<210> SEQ ID NO 6
<211> LENGTH: 1443
<212> TYPE: DNA
<213> ORGANISM: Artificial
<220> FEATURE:
<223> OTHER INFORMATION: A nucleotide sequence of
      pMCDN2_HS6ST2_N-short_ctV5.

<400> SEQUENCE: 6
atggatgaga aatccaacaa gctgctgcta gctttggtga tgctcttcct atttgccgtg     60
atcgtcctcc aatacgtgtg ccccggcaca gaatgccagc tcctccgcct gcaggcgttc    120
agctccccgg tgccggaccc gtaccgctcg aggatgagag ctccgccag  gttcgtgccc    180 cgctacaatt tcacccgcgg cgacctcctg cgcaaggtag acttcgacat caagggcgat    240
gacctgatcg tgttcctgca catccagaag accgggggca ccactttcgg ccgccacttg    300
gtgcgtaaca tccagctgga gcagccgtgc gagtgccgcg tgggtcagaa gaaatgcact    360
tgccaccggc cgggtaagcg ggaaacctgg ctcttctcca ggttctccac gggctggagc    420
tgcgggttgc acgccgactg gaccgagctc accagctgtg tgccctccgt ggtggacggc    480
```

-continued

```
aagcgcgacg ccaggctgag accgtccagg aacttccact acatcaccat cctccgagac    540
ccagtgtccc ggtacttgag tgagtggagg catgtccaga gaggggcaac atggaaagca    600
tccctgcatg tctgcgatgg aaggcctcca acctccgaag agctgcccag ctgctacact    660
ggcgatgact ggtctggctg cccctcaaa gagtttatgg actgtcccta caatctagcc      720
aacaaccgcc aggtgcgcat gctctccgac ctgaccctgg taggctgcta caacctctct    780
gtcatgcctg aaaagcaaag aaacaaggtc cttctggaaa gtgccaagtc aaatctgaag    840
cacatggcgt tcttcggcct cactgagttt cagcggaaga cccaatatct gtttgagaaa    900
accttcaaca tgaactttat ttcgccattt acccagtata ataccactag ggcctctagt    960
gtagagatca atgaggaaat tcaaaagcgt attgagggac tgaattttct ggatatggag    1020
ttgtacagct atgccaaaga cctttttttg cagaggtatc agtttatgag cagaaagag     1080 catcaggagg ccaggcgaaa gcgtcaggaa caacgcaaat ttctgaaggg aaggctcctt    1140
cagacccatt tccagagcca gggtcagggc cagagccaga atccgaatca gaatcagagt    1200
cagaacccaa atccgaatgc caatcagaac ctgactcaga atctgatgca gaatctgact    1260
cagagtttga gccagaagga gaaccgggaa agcccgaagc agaactcagg caaggagcag    1320
aatgataaca ccagcaatgg caccaacgac tacataggca gtgtagagaa atggcgtagc    1380
ggccgcggta agcctatccc taaccctctc ctcggtctcg attctacgcg taccggttag    1440
taa                                                                  1443
```

<210> SEQ ID NO 7
<211> LENGTH: 479
<212> TYPE: PRT
<213> ORGANISM: Artificial
<220> FEATURE:
<223> OTHER INFORMATION: An amino acid sequence coded by a nucleotide
      sequence of pMCDN2_HS6ST2_N-short_ctV5.

<400> SEQUENCE: 7

```
Met Asp Glu Lys Ser Asn Lys Leu Leu Leu Ala Leu Val Met Leu Phe
1               5                   10                  15

Leu Phe Ala Val Ile Val Leu Gln Tyr Val Cys Pro Gly Thr Glu Cys
            20                  25                  30

Gln Leu Leu Arg Leu Gln Ala Phe Ser Ser Pro Val Pro Asp Pro Tyr
        35                  40                  45

Arg Ser Glu Asp Glu Ser Ser Ala Arg Phe Val Pro Arg Tyr Asn Phe
    50                  55                  60

Thr Arg Gly Asp Leu Leu Arg Lys Val Asp Phe Asp Ile Lys Gly Asp
65                  70                  75                  80

Asp Leu Ile Val Phe Leu His Ile Gln Lys Thr Gly Gly Thr Thr Phe
                85                  90                  95

Gly Arg His Leu Val Arg Asn Ile Gln Leu Glu Gln Pro Cys Glu Cys
            100                 105                 110

Arg Val Gly Gln Lys Lys Cys Thr Cys His Arg Pro Gly Lys Arg Glu
        115                 120                 125

Thr Trp Leu Phe Ser Arg Phe Ser Thr Gly Trp Ser Cys Gly Leu His
    130                 135                 140

Ala Asp Trp Thr Glu Leu Thr Ser Cys Val Pro Ser Val Val Asp Gly
145                 150                 155                 160

Lys Arg Asp Ala Arg Leu Arg Pro Ser Arg Asn Phe His Tyr Ile Thr
                165                 170                 175

Ile Leu Arg Asp Pro Val Ser Arg Tyr Leu Ser Glu Trp Arg His Val
```

```
                180                 185                 190
Gln Arg Gly Ala Thr Trp Lys Ala Ser Leu His Val Cys Asp Gly Arg
            195                 200                 205

Pro Pro Thr Ser Glu Glu Leu Pro Ser Cys Tyr Thr Gly Asp Asp Trp
    210                 215                 220

Ser Gly Cys Pro Leu Lys Glu Phe Met Asp Cys Pro Tyr Asn Leu Ala
225                 230                 235                 240

Asn Asn Arg Gln Val Arg Met Leu Ser Asp Leu Thr Leu Val Gly Cys
            245                 250                 255

Tyr Asn Leu Ser Val Met Pro Glu Lys Gln Arg Asn Lys Val Leu Leu
            260                 265                 270

Glu Ser Ala Lys Ser Asn Leu Lys His Met Ala Phe Phe Gly Leu Thr
            275                 280                 285

Glu Phe Gln Arg Lys Thr Gln Tyr Leu Phe Glu Lys Thr Phe Asn Met
            290                 295                 300

Asn Phe Ile Ser Pro Phe Thr Gln Tyr Asn Thr Thr Arg Ala Ser Ser
305                 310                 315                 320

Val Glu Ile Asn Glu Glu Ile Gln Lys Arg Ile Glu Gly Leu Asn Phe
            325                 330                 335

Leu Asp Met Glu Leu Tyr Ser Tyr Ala Lys Asp Leu Phe Leu Gln Arg
            340                 345                 350

Tyr Gln Phe Met Arg Gln Lys Glu His Gln Glu Ala Arg Arg Lys Arg
            355                 360                 365

Gln Glu Gln Arg Lys Phe Leu Lys Gly Arg Leu Leu Gln Thr His Phe
    370                 375                 380

Gln Ser Gln Gly Gln Gly Gln Ser Gln Asn Pro Asn Gln Asn Gln Ser
385                 390                 395                 400

Gln Asn Pro Asn Pro Asn Ala Asn Gln Asn Leu Thr Gln Asn Leu Met
            405                 410                 415

Gln Asn Leu Thr Gln Ser Leu Ser Gln Lys Glu Asn Arg Glu Ser Pro
            420                 425                 430

Lys Gln Asn Ser Gly Lys Glu Gln Asn Asp Asn Thr Ser Asn Gly Thr
            435                 440                 445

Asn Asp Tyr Ile Gly Ser Val Glu Lys Trp Arg Ser Gly Arg Gly Lys
            450                 455                 460

Pro Ile Pro Asn Pro Leu Leu Gly Leu Asp Ser Thr Arg Thr Gly
465                 470                 475

<210> SEQ ID NO 8
<211> LENGTH: 29
<212> TYPE: DNA
<213> ORGANISM: Artificial
<220> FEATURE:
<223> OTHER INFORMATION: A nucleotide sequence of a reverse primer for
      pMC_HS6ST2_N-short (HS6ST2-taaR, p25).

<400> SEQUENCE: 8
attgtcgact taacgccatt tctctacac                                   29

<210> SEQ ID NO 9
<211> LENGTH: 65
<212> TYPE: DNA
<213> ORGANISM: Artificial
<220> FEATURE:
<223> OTHER INFORMATION: A nucleotide sequence of a forward primer for
      pMCDN2_sHS6ST2_FLAG (HS6ST2-11, p81).

<400> SEQUENCE: 9
```

```
gctcctggcg ctgctggctg cgctctgccc ggcgagtcgg gctcaatacg tgtgccccgg    60
cacag                                                                65

<210> SEQ ID NO 10
<211> LENGTH: 63
<212> TYPE: DNA
<213> ORGANISM: Artificial
<220> FEATURE:
<223> OTHER INFORMATION: A nucleotide sequence of a reverse primer for
      pMCDN2_sHS6ST2_FLAG (HS6ST2-13, p81).

<400> SEQUENCE: 10
tttgcggccg ctcacttgtc atcgtcgtcc ttgtagtcac gccatttctc tacactgcct    60
atg                                                                  63

<210> SEQ ID NO 11
<211> LENGTH: 62
<212> TYPE: DNA
<213> ORGANISM: Artificial
<220> FEATURE:
<223> OTHER INFORMATION: A nucleotide sequence of a forward primer for
      pMCDN2_sHS6ST2_FLAG (HS6ST2-12, p81).

<400> SEQUENCE: 11
tttgaattcc accatgcgac cctccgggac ggccggggca cgctcctgg cgctgctggc    60 tg                                                                   62

<210> SEQ ID NO 12
<211> LENGTH: 1407
<212> TYPE: DNA
<213> ORGANISM: Artificial
<220> FEATURE:
<223> OTHER INFORMATION: A nucleotide sequence of pMCDN2_sHS6ST2_FLAG.

<400> SEQUENCE: 12
atgcgaccct ccgggacggc cggggcagcg ctcctggcgc tgctggctgc gctctgcccg    60
gcgagtcggg ctcaatacgt gtgccccggc acagaatgcc agctcctccg cctgcaggcg   120
ttcagctccc cggtgccgga cccgtaccgc tcggaggatg agagctccgc caggttcgtg   180
ccccgctaca atttcacccg cggcgacctc ctgcgcaagg tagacttcga catcaagggc   240
gatgacctga tcgtgttcct gcacatccag aagaccgggg gcaccacttt cggccgccac   300
ttggtgcgta acatccagct ggagcagccg tgcgagtgcc gcgtgggtca agaaaatgc    360 acttgccacc ggccgggtaa gcgggaaacc tggctcttct ccaggttctc cacgggctgg   420
agctgcgggt tgcacgccga ctggaccgag ctcaccagct gtgtgccctc cgtggtggac   480
ggcaagcgcg acgccaggct gagaccgtcc aggaacttcc actacatcac catcctccga   540
gacccagtgt cccggtactt gagtgagtgg aggcatgtcc agagaggggc aacatggaaa   600
gcatccctgc atgtctgcga tggaaggcct ccaacctccg aagagctgcc agctgctac    660 actggcgatg actggtctgg ctgccccctc aaagagttta tggactgtcc ctacaatcta   720
gccaacaacc gccaggtgcg catgctctcc gacctgaccc tggtaggctg ctacaacctc   780
tctgtcatgc ctgaaaagca agaaacaag gtccttctgg aaagtgccaa gtcaaatctg   840
aagcacatgg cgttcttcgg cctcactgag tttcagcgga agacccaata tctgtttgag   900
aaaaccttca acatgaactt tatttcgcca tttacccagt ataataccac tagggcctct   960
agtgtagaga tcaatgagga aattcaaaag cgtattgagg gactgaattt tctggatatg  1020
```

```
gagttgtaca gctatgccaa agaccttttt ttgcagaggt atcagtttat gaggcagaaa    1080
gagcatcagg aggccaggcg aaagcgtcag gaacaacgca aatttctgaa gggaaggctc    1140
cttcagaccc atttccagag ccagggtcag ggccagagcc agaatccgaa tcagaatcag    1200
agtcagaacc caaatccgaa tgccaatcag aacctgactc agaatctgat gcagaatctg    1260
actcagagtt tgagccagaa ggagaaccgg gaaagcccga agcagaactc aggcaaggag    1320
cagaatgata acaccagcaa tgccaccaac gactacatag gcagtgtaga gaaatggcgt    1380
gactacaagg acgacgatga caagtga                                        1407
```

<210> SEQ ID NO 13
<211> LENGTH: 468
<212> TYPE: PRT
<213> ORGANISM: Artificial
<220> FEATURE:
<223> OTHER INFORMATION: An amino acid sequence coded by a nucleotide
      sequence of pMCDN2_s HS6ST2_FLAG.

<400> SEQUENCE: 13

```
Met Arg Pro Ser Gly Thr Ala Gly Ala Ala Leu Leu Ala Leu Leu Ala
1               5                   10                  15

Ala Leu Cys Pro Ala Ser Arg Ala Gln Tyr Val Cys Pro Gly Thr Glu
            20                  25                  30

Cys Gln Leu Leu Arg Leu Gln Ala Phe Ser Ser Pro Val Pro Asp Pro
        35                  40                  45

Tyr Arg Ser Glu Asp Glu Ser Ser Ala Arg Phe Val Pro Arg Tyr Asn
    50                  55                  60

Phe Thr Arg Gly Asp Leu Leu Arg Lys Val Asp Phe Asp Ile Lys Gly
65                  70                  75                  80

Asp Asp Leu Ile Val Phe Leu His Ile Gln Lys Thr Gly Gly Thr Thr
                85                  90                  95

Phe Gly Arg His Leu Val Arg Asn Ile Gln Leu Glu Gln Pro Cys Glu
            100                 105                 110

Cys Arg Val Gly Gln Lys Lys Cys Thr Cys His Arg Pro Gly Lys Arg
        115                 120                 125

Glu Thr Trp Leu Phe Ser Arg Phe Ser Thr Gly Trp Ser Cys Gly Leu
    130                 135                 140

His Ala Asp Trp Thr Glu Leu Thr Ser Cys Val Pro Ser Val Val Asp
145                 150                 155                 160

Gly Lys Arg Asp Ala Arg Leu Arg Pro Ser Arg Asn Phe His Tyr Ile
                165                 170                 175

Thr Ile Leu Arg Asp Pro Val Ser Arg Tyr Leu Ser Glu Trp Arg His
            180                 185                 190

Val Gln Arg Gly Ala Thr Trp Lys Ala Ser Leu His Val Cys Asp Gly
        195                 200                 205

Arg Pro Pro Thr Ser Glu Glu Leu Pro Ser Cys Tyr Thr Gly Asp Asp
    210                 215                 220

Trp Ser Gly Cys Pro Leu Lys Glu Phe Met Asp Cys Pro Tyr Asn Leu
225                 230                 235                 240

Ala Asn Asn Arg Gln Val Arg Met Leu Ser Asp Leu Thr Leu Val Gly
                245                 250                 255

Cys Tyr Asn Leu Ser Val Met Pro Glu Lys Gln Arg Asn Lys Val Leu
            260                 265                 270

Leu Glu Ser Ala Lys Ser Asn Leu Lys His Met Ala Phe Phe Gly Leu
        275                 280                 285
```

Thr Glu Phe Gln Arg Lys Thr Gln Tyr Leu Phe Glu Lys Thr Phe Asn
290                 295                 300

Met Asn Phe Ile Ser Pro Phe Thr Gln Tyr Asn Thr Thr Arg Ala Ser
305                 310                 315                 320

Ser Val Glu Ile Asn Glu Glu Ile Gln Lys Arg Ile Glu Gly Leu Asn
            325                 330                 335

Phe Leu Asp Met Glu Leu Tyr Ser Tyr Ala Lys Asp Leu Phe Leu Gln
                340                 345                 350

Arg Tyr Gln Phe Met Arg Gln Lys Glu His Gln Glu Ala Arg Arg Lys
            355                 360                 365

Arg Gln Glu Gln Arg Lys Phe Leu Lys Gly Arg Leu Leu Gln Thr His
370                 375                 380

Phe Gln Ser Gln Gly Gln Gly Gln Ser Gln Asn Pro Asn Gln Asn Gln
385                 390                 395                 400

Ser Gln Asn Pro Asn Pro Asn Ala Asn Gln Asn Leu Thr Gln Asn Leu
            405                 410                 415

Met Gln Asn Leu Thr Gln Ser Leu Ser Gln Lys Glu Asn Arg Glu Ser
                420                 425                 430

Pro Lys Gln Asn Ser Gly Lys Glu Gln Asn Asp Asn Thr Ser Asn Gly
            435                 440                 445

Thr Asn Asp Tyr Ile Gly Ser Val Glu Lys Trp Arg Asp Tyr Lys Asp
450                 455                 460

Asp Asp Asp Lys
465

<210> SEQ ID NO 14
<211> LENGTH: 34
<212> TYPE: DNA
<213> ORGANISM: Artificial
<220> FEATURE:
<223> OTHER INFORMATION: A nucleotide sequence of a forward primer for
      cloning of mHS6ST2 (mHS6ST2-EcoR1, p3).

<400> SEQUENCE: 14
tatgaattcc accatggatg agaaatctaa caag                               34

<210> SEQ ID NO 15
<211> LENGTH: 29
<212> TYPE: DNA
<213> ORGANISM: Artificial
<220> FEATURE:
<223> OTHER INFORMATION: A nucleotide sequence of a reverse primer for
      cloning of mHS6ST2 (mHS6ST2-Not1, p3).

<400> SEQUENCE: 15
atagcggccg cttagcgcca tgtctctac                                     29

<210> SEQ ID NO 16
<211> LENGTH: 67
<212> TYPE: DNA
<213> ORGANISM: Artificial
<220> FEATURE:
<223> OTHER INFORMATION: A partial nucleotide sequence of pMCDN2_ntHA
      expression vector.

<400> SEQUENCE: 16
gaattccacc atgtacccat acgatgttcc agattacgct agcgtcgact acagcggccg   60
ctgatag                                                             67

<210> SEQ ID NO 17

```
<211> LENGTH: 30
<212> TYPE: DNA
<213> ORGANISM: Artificial
<220> FEATURE:
<223> OTHER INFORMATION: A nucleotide sequence of a forward primer for
      pMDCN2_mHS6ST2_ntHA (mHS6ST2-Nhe1, p3).

<400> SEQUENCE: 17
taagctagcg atgagaaatc taacaagctg                                        30

<210> SEQ ID NO 18
<211> LENGTH: 33
<212> TYPE: DNA
<213> ORGANISM: Artificial
<220> FEATURE:
<223> OTHER INFORMATION: A nucleotide sequence of a reverse primer for
      pMCDN2_mHS6ST2_ctV5 (NotI-mHS6ST2, p89).

<400> SEQUENCE: 18
gcggccgctg cgccatgtct ctacgctccc tat                                    33

<210> SEQ ID NO 19
<211> LENGTH: 1470
<212> TYPE: DNA
<213> ORGANISM: Artificial
<220> FEATURE:
<223> OTHER INFORMATION: A nucleotide sequence of pMCDN2_mHS6ST2_ctV5.

<400> SEQUENCE: 19
atggctagcg atgagaaatc taacaagctg ctgctggctt tggtgatgct cttcctattt        60
gcggtgatcg tcctccaata cgtgtgcccc ggcacagaat gccagctcct ccgcctgcag       120
gcgttcagct ccccggtgcc ggatccgtac cgctcggagg atgagagttc ggccaggttt       180
gtaccccgct acaatttcag ccgcggcgat ctcctgcgca aggtagactt cgacatcaag       240
ggcgatgacc tgatcgtgtt cctgcacatc agaagactg gggcaccac ttttggccgt         300 cacctggtgc gcaacatcca gctggagcag ccatgtgagt gccgcgtggg gcagaagaaa       360
tgcacttgcc accggccggg taagagggag acctggctct ctccaggtt ctccaccggc        420 tggagctgcg ggctgcatgc cgactggacc gagctcacca gctgcgtgcc ggcggtggtg       480
gatggcaagc gcgacgccag gctgagacct tccaggaact tccattacat taccatcctg      540
agagacccag tgtcacggta cttgagtgaa tggaggcatg tccagagagg agcaacttgg       600
aaagcatccc tgcacgtctg tgatggaagg ccccaaacct ctgaagagct gcccagctgc       660
tacaccggtg atgactggtc tggatgccct ctcaaagagt tcatgactg tccctataat        720 ctggccaaca accgccaagt tcgcatgcta tctgacctga ctctagtggg atgctacaac       780
ctctctgtca tgcctgaaaa gcaaagaaac aaagtccttc tggaaagtgc caaatccaat      840
ctgaagcaca tggcgttctt tggcctcact gagtttcagc gcaagaccca gtacctgttt       900
gagaagacct tcaacatgaa ctttatctcg ccgtttaccc agtataatac cactagggcc      960
tctagtgttg agatcaatga ggaaatccaa aagcgtattg agggactgaa ttttctggat      1020
atggagttgt acagctatgc taaagacctc tttctgcaaa ggtatcagtt catgaggcag     1080
aaagaacatc aggatgccag gcggaagcgt caggagcaac gcaaatttct gaagggaagg     1140
ttccttcaga cccatttcca gagtcagagt cagggtcaga gccagagcca gagtccaggt     1200
cagaatctga gtcagaatcc aaatcctaac ccaaatcaga acctgactca gaacctgagt     1260
cacaatctga ctccgagttc aaatcccaat tcgacccaga gggagaaccg gggaagtcag     1320
aagcagggct caggccaggg acaaggtgat agcggcacca gcaatggcac caatgactac     1380
```

```
ataggagcg tagagacatg gcgcagcggc cgcggtaagc ctatccctaa ccctctcctc    1440
ggtctcgatt ctacgcgtac cggttagtaa                                   1470
```

<210> SEQ ID NO 20
<211> LENGTH: 488
<212> TYPE: PRT
<213> ORGANISM: Artificial
<220> FEATURE:
<223> OTHER INFORMATION: An amino acid sequence coded by a nucleotide
      sequence of pMCDN2_mHS6ST2_ctV5.

<400> SEQUENCE: 20

```
Met Ala Ser Asp Glu Lys Ser Asn Lys Leu Leu Leu Ala Leu Val Met
1               5                   10                  15

Leu Phe Leu Phe Ala Val Ile Val Leu Gln Tyr Val Cys Pro Gly Thr
            20                  25                  30

Glu Cys Gln Leu Leu Arg Leu Gln Ala Phe Ser Ser Pro Val Pro Asp
        35                  40                  45

Pro Tyr Arg Ser Glu Asp Glu Ser Ser Ala Arg Phe Val Pro Arg Tyr
    50                  55                  60

Asn Phe Ser Arg Gly Asp Leu Leu Arg Lys Val Asp Phe Asp Ile Lys
65                  70                  75                  80

Gly Asp Asp Leu Ile Val Phe Leu His Ile Gln Lys Thr Gly Gly Thr
                85                  90                  95

Thr Phe Gly Arg His Leu Val Arg Asn Ile Gln Leu Glu Gln Pro Cys
            100                 105                 110

Glu Cys Arg Val Gly Gln Lys Lys Cys Thr Cys His Arg Pro Gly Lys
        115                 120                 125

Arg Glu Thr Trp Leu Phe Ser Arg Phe Ser Thr Gly Trp Ser Cys Gly
    130                 135                 140

Leu His Ala Asp Trp Thr Glu Leu Thr Ser Cys Val Pro Ala Val Val
145                 150                 155                 160

Asp Gly Lys Arg Asp Ala Arg Leu Arg Pro Ser Arg Asn Phe His Tyr
                165                 170                 175

Ile Thr Ile Leu Arg Asp Pro Val Ser Arg Tyr Leu Ser Glu Trp Arg
            180                 185                 190

His Val Gln Arg Gly Ala Thr Trp Lys Ala Ser Leu His Val Cys Asp
        195                 200                 205

Gly Arg Pro Pro Thr Ser Glu Glu Leu Pro Ser Cys Tyr Thr Gly Asp
    210                 215                 220

Asp Trp Ser Gly Cys Pro Leu Lys Glu Phe Met Asp Cys Pro Tyr Asn
225                 230                 235                 240

Leu Ala Asn Asn Arg Gln Val Arg Met Leu Ser Asp Leu Thr Leu Val
                245                 250                 255

Gly Cys Tyr Asn Leu Ser Val Met Pro Glu Lys Gln Arg Asn Lys Val
            260                 265                 270

Leu Leu Glu Ser Ala Lys Ser Asn Leu Lys His Met Ala Phe Phe Gly
        275                 280                 285

Leu Thr Glu Phe Gln Arg Lys Thr Gln Tyr Leu Phe Glu Lys Thr Phe
    290                 295                 300

Asn Met Asn Phe Ile Ser Pro Phe Thr Gln Tyr Asn Thr Thr Arg Ala
305                 310                 315                 320

Ser Ser Val Glu Ile Asn Glu Glu Ile Gln Lys Arg Ile Glu Gly Leu
                325                 330                 335
```

```
Asn Phe Leu Asp Met Glu Leu Tyr Ser Tyr Ala Lys Asp Leu Phe Leu
                340                 345                 350

Gln Arg Tyr Gln Phe Met Arg Gln Lys Glu His Gln Asp Ala Arg Arg
            355                 360                 365

Lys Arg Gln Glu Gln Arg Lys Phe Leu Lys Gly Arg Phe Leu Gln Thr
        370                 375                 380

His Phe Gln Ser Gln Ser Gln Gly Gln Ser Gln Ser Gln Ser Pro Gly
385                 390                 395                 400

Gln Asn Leu Ser Gln Asn Pro Asn Pro Asn Pro Gln Asn Leu Thr
                405                 410                 415

Gln Asn Leu Ser His Asn Leu Thr Pro Ser Ser Asn Pro Asn Ser Thr
                420                 425                 430

Gln Arg Glu Asn Arg Gly Ser Gln Lys Gln Gly Ser Gln Gly Gln
                435                 440                 445

Gly Asp Ser Gly Thr Ser Asn Gly Thr Asn Asp Tyr Ile Gly Ser Val
            450                 455                 460

Glu Thr Trp Arg Ser Gly Arg Gly Lys Pro Ile Pro Asn Pro Leu Leu
465                 470                 475                 480

Gly Leu Asp Ser Thr Arg Thr Gly
                485

<210> SEQ ID NO 21
<211> LENGTH: 29
<212> TYPE: DNA
<213> ORGANISM: Artificial
<220> FEATURE:
<223> OTHER INFORMATION: A nucleotide sequence of a forward primer for
      GST_HS6ST2_N (GST_hHS6ST2_N F, p27).

<400> SEQUENCE: 21
attgaattcc aatacgtgtg ccccggcac                                   29

<210> SEQ ID NO 22
<211> LENGTH: 58
<212> TYPE: DNA
<213> ORGANISM: Artificial
<220> FEATURE:
<223> OTHER INFORMATION: A nucleotide sequence of a reverse primer for
      GST_HS6ST2_N (GST_hHS6ST2_N R, p27).

<400> SEQUENCE: 22
ttagcggccg cttatcaatg atgatgatga tgatggatgt agtggaagtt cctggacg   58

<210> SEQ ID NO 23
<211> LENGTH: 30
<212> TYPE: DNA
<213> ORGANISM: Artificial
<220> FEATURE:
<223> OTHER INFORMATION: A nucleotide sequence of a forward primer for
      GST_HS6ST2_mid.

<400> SEQUENCE: 23
attgaattcc tgagaccgtc caggaacttc                                  30

<210> SEQ ID NO 24
<211> LENGTH: 62
<212> TYPE: DNA
<213> ORGANISM: Artificial
<220> FEATURE:
<223> OTHER INFORMATION: A nucleotide sequence of a reverse primer for
      GST_HS6ST2_mid.

<400> SEQUENCE: 24
```

```
ttagcggccg cttatcaatg atgatgatga tgatgcctag tggtattata ctgggtaaat    60
gg                                                                   62
```

<210> SEQ ID NO 25
<211> LENGTH: 35
<212> TYPE: DNA
<213> ORGANISM: Artificial
<220> FEATURE:
<223> OTHER INFORMATION: A nucleotide sequence of a forward primer for
      GST_HS6ST2_C.

<400> SEQUENCE: 25

```
attgaattct cgccatttac ccagtataat accac                                35
```

<210> SEQ ID NO 26
<211> LENGTH: 56
<212> TYPE: DNA
<213> ORGANISM: Artificial
<220> FEATURE:
<223> OTHER INFORMATION: A nucleotide sequence of a reverse primer for
      GST_HS6ST2_C.

<400> SEQUENCE: 26

```
ttagcggccg cttatcaatg atgatgatga tgatgacgcc atttctctac actgcc         56
```

<210> SEQ ID NO 27
<211> LENGTH: 52
<212> TYPE: DNA
<213> ORGANISM: Artificial
<220> FEATURE:
<223> OTHER INFORMATION: A nucleotide sequence of a reverse primer for
      GST_HS6ST2_C1 (GST_hHS6ST2_C R2, p46).

<400> SEQUENCE: 27

```
ttagcggccg cttatcaatg atgatgatga tgatgctggc tctggccctg ac             52
```

<210> SEQ ID NO 28
<211> LENGTH: 30
<212> TYPE: DNA
<213> ORGANISM: Artificial
<220> FEATURE:
<223> OTHER INFORMATION: A nucleotide sequence of a forward primer for
      GST_HS6ST2_C2 (GST_hHS6ST2_C F2, p46).

<400> SEQUENCE: 28

```
attgaattcc tccttcagac ccatttccag                                      30
```

<210> SEQ ID NO 29
<211> LENGTH: 20
<212> TYPE: DNA
<213> ORGANISM: Artificial
<220> FEATURE:
<223> OTHER INFORMATION: A nucleotide sequence of a forward primer for
      cloning of HS6ST2_N-long (HS6ST2 RT F4, p82).

<400> SEQUENCE: 29

```
ggcgtgaggc attattatat                                                 20
```

<210> SEQ ID NO 30
<211> LENGTH: 19
<212> TYPE: DNA
<213> ORGANISM: Artificial
<220> FEATURE:
<223> OTHER INFORMATION: A nucleotide sequence of a reverse primer for
      cloning of HS6ST2 N-long (HS6ST2 RT R2, p82).

<400> SEQUENCE: 30
caaataggaa gagcatcac                                                19

<210> SEQ ID NO 31
<211> LENGTH: 31
<212> TYPE: DNA
<213> ORGANISM: Artificial
<220> FEATURE:
<223> OTHER INFORMATION: A nucleotide sequence of a forward primer for
      cloning of HS6ST2 N-long (HS6ST2 ecoRI RT F5, p106).

<400> SEQUENCE: 31
aagaattccc accatggcac tgcctgcgtg t                                  31

<210> SEQ ID NO 32
<211> LENGTH: 1881
<212> TYPE: DNA
<213> ORGANISM: Artificial
<220> FEATURE:
<223> OTHER INFORMATION: A nucleotide sequence of
      pMCDN2_HS6ST2_N-long_ctV5.

<400> SEQUENCE: 32
atggcactgc ctgcgtgtgc agtccgggag ttcgagccgc cgcggcaacc ggagcgagga      60
gcgcccgtcc gcaccacctg tccccgccgg cattccagag tagaggccga attggcagcg     120
agccggcccg ggtcggtcgc cgcctcagtt cgcgcgggcc ctcctagggg tgtgtctcac     180
ggattccaca cccggccgct cctggacaag ccccgaaagg cgtcttcttc cctggcggga     240
gccgcgtgcg ccccgctttt cgcgctgctg tcccggggcc gccgcaggcg gatgcacgtc     300
ctcaggcgac gctgggacct gggctccctc tgccgggccc tgctcactcg gggcctggcc     360
gccctgggcc actcgctgaa gcacgtgctc ggtgcgatct tctccaagat tttcggcccc     420
atggccagcg tcgggaacat ggatgagaaa tccaacaagc tgctgctagc tttggtgatg     480
ctcttcctat ttgccgtgat cgtcctccaa tacgtgtgcc ccggcacaga atgccagctc     540
ctccgcctgc aggcgttcag ctccccggtg ccggacccgt accgctcgga ggatgagagc     600
tccgccaggt tcgtgccccg ctacaatttc acccgcggcg acctcctgcg caaggtagac     660
ttcgacatca agggcgatga cctgatcgtg ttcctgcaca tccagaagac cggggggcacc     720 actttcggcc gccacttggt gcgtaacatc cagctggagc agccgtgcga gtgccgcgtg     780
ggtcagaaga aatgcacttg ccaccggccg ggtaagcggg aaacctggct cttctccagg     840
ttctccacgg gctggagctg cgggttgcac gccgactgga ccgagctcac cagctgtgtg     900
ccctccgtgg tggacggcaa gcgcgacgcc aggctgagac cgtccaggaa cttccactac     960
atcaccatcc tccgagaccc agtgtccgg tacttgagtg agtggaggca tgtccagaga    1020
ggggcaacat ggaaagcatc cctgcatgtc tgcgatggaa ggcctccaac ctccgaagag    1080
ctgcccagct gctacactgg cgatgactgg tctggctgcc ccctcaaaga gtttatggac    1140
tgtccctaca tctagccaa caaccgccag gtgcgcatgc tctccgacct gaccctggta    1200
ggctgctaca acctctctgt catgcctgaa agcaaagaa acaaggtcct tctggaaagt    1260
gccaagtcaa atctgaagca catggcgttc ttcggcctca ctgagtttca gcggaagacc    1320
caatatctgt ttgagaaaac cttcaacatg aactttattt cgccatttac ccagtataat    1380
accactaggg cctctagtgt agagatcaat gaggaaattc aaaagcgtat tgagggactg    1440
aattttctgg atatggagtt gtacagctat gccaaagacc ttttttttgca gaggtatcag    1500 tttatgaggc agaaagagca tcaggaggcc aggcgaaagc gtcaggaaca acgcaaattt    1560

```
ctgaaggggaa ggctccttca gacccatttc cagagccagg gtcagggcca gagccagaat    1620
ccgaatcaga atcagagtca gaacccaaat ccgaatgcca atcagaacct gactcagaat    1680
ctgatgcaga atctgactca gagtttgagc cagaaggaga accgggaaag cccgaagcag    1740
aactcaggca aggagcagaa tgataacacc agcaatggcc caacgactac ataggcagt     1800 gtagagaaat ggcgtagcgg ccgcggtaag cctatcccta accctctcct cggtctcgat    1860
tctacgcgta ccggttagta a                                               1881
```

<210> SEQ ID NO 33
<211> LENGTH: 625
<212> TYPE: PRT
<213> ORGANISM: Artificial
<220> FEATURE:
<223> OTHER INFORMATION: An amino acid sequence coded by a nucleotide sequence of pMCDN2_HS6ST2_N-long_ctV5.

<400> SEQUENCE: 33

```
Met Ala Leu Pro Ala Cys Ala Val Arg Glu Phe Glu Pro Pro Arg Gln
1               5                   10                  15

Pro Glu Arg Gly Ala Pro Val Arg Thr Thr Cys Pro Arg Arg His Ser
            20                  25                  30

Arg Val Glu Ala Glu Leu Ala Ala Ser Arg Pro Gly Ser Val Ala Ala
        35                  40                  45

Ser Val Arg Ala Gly Pro Pro Arg Gly Val Ser Gly Phe His Thr
    50                  55                  60

Arg Pro Leu Leu Asp Lys Pro Lys Ala Ser Ser Ser Leu Ala Gly
65                  70                  75                  80

Ala Ala Cys Ala Pro Leu Phe Ala Leu Leu Ser Arg Gly Arg Arg
            85                  90                  95

Arg Met His Val Leu Arg Arg Arg Trp Asp Leu Gly Ser Leu Cys Arg
            100                 105                 110

Ala Leu Leu Thr Arg Gly Leu Ala Ala Leu Gly His Ser Leu Lys His
        115                 120                 125

Val Leu Gly Ala Ile Phe Ser Lys Ile Phe Gly Pro Met Ala Ser Val
    130                 135                 140

Gly Asn Met Asp Glu Lys Ser Asn Lys Leu Leu Leu Ala Leu Val Met
145                 150                 155                 160

Leu Phe Leu Phe Ala Val Ile Val Leu Gln Tyr Val Cys Pro Gly Thr
                165                 170                 175

Glu Cys Gln Leu Leu Arg Leu Gln Ala Phe Ser Ser Pro Val Pro Asp
            180                 185                 190

Pro Tyr Arg Ser Glu Asp Glu Ser Ser Ala Arg Phe Val Pro Arg Tyr
        195                 200                 205

Asn Phe Thr Arg Gly Asp Leu Leu Arg Lys Val Asp Phe Asp Ile Lys
    210                 215                 220

Gly Asp Asp Leu Ile Val Phe Leu His Ile Gln Lys Thr Gly Gly Thr
225                 230                 235                 240

Thr Phe Gly Arg His Leu Val Arg Asn Ile Gln Leu Glu Gln Pro Cys
                245                 250                 255

Glu Cys Arg Val Gly Gln Lys Lys Cys Thr Cys His Arg Pro Gly Lys
            260                 265                 270

Arg Glu Thr Trp Leu Phe Ser Arg Phe Ser Thr Gly Trp Ser Cys Gly
        275                 280                 285

Leu His Ala Asp Trp Thr Glu Leu Thr Ser Cys Val Pro Ser Val Val
```

```
Asp Gly Lys Arg Asp Ala Arg Leu Arg Pro Ser Arg Asn Phe His Tyr
305                 310                 315                 320
Ile Thr Ile Leu Arg Asp Pro Val Ser Arg Tyr Leu Ser Glu Trp Arg
                325                 330                 335
His Val Gln Arg Gly Ala Thr Trp Lys Ala Ser Leu His Val Cys Asp
            340                 345                 350
Gly Arg Pro Pro Thr Ser Glu Glu Leu Pro Ser Cys Tyr Thr Gly Asp
        355                 360                 365
Asp Trp Ser Gly Cys Pro Leu Lys Glu Phe Met Asp Cys Pro Tyr Asn
    370                 375                 380
Leu Ala Asn Asn Arg Gln Val Arg Met Leu Ser Asp Leu Thr Leu Val
385                 390                 395                 400
Gly Cys Tyr Asn Leu Ser Val Met Pro Glu Lys Gln Arg Asn Lys Val
                405                 410                 415
Leu Leu Glu Ser Ala Lys Ser Asn Leu Lys His Met Ala Phe Phe Gly
            420                 425                 430
Leu Thr Glu Phe Gln Arg Lys Thr Gln Tyr Leu Phe Glu Lys Thr Phe
        435                 440                 445
Asn Met Asn Phe Ile Ser Pro Phe Thr Gln Tyr Asn Thr Thr Arg Ala
    450                 455                 460
Ser Ser Val Glu Ile Asn Glu Glu Ile Gln Lys Arg Ile Glu Gly Leu
465                 470                 475                 480
Asn Phe Leu Asp Met Glu Leu Tyr Ser Tyr Ala Lys Asp Leu Phe Leu
                485                 490                 495
Gln Arg Tyr Gln Phe Met Arg Gln Lys Glu His Gln Glu Ala Arg Arg
            500                 505                 510
Lys Arg Gln Glu Gln Arg Lys Phe Leu Lys Gly Arg Leu Leu Gln Thr
        515                 520                 525
His Phe Gln Ser Gln Gly Gln Gly Gln Ser Gln Asn Pro Asn Gln Asn
    530                 535                 540
Gln Ser Gln Asn Pro Asn Pro Asn Ala Asn Gln Asn Leu Thr Gln Asn
545                 550                 555                 560
Leu Met Gln Asn Leu Thr Gln Ser Leu Ser Gln Lys Glu Asn Arg Glu
                565                 570                 575
Ser Pro Lys Gln Asn Ser Gly Lys Glu Gln Asn Asp Asn Thr Ser Asn
            580                 585                 590
Gly Thr Asn Asp Tyr Ile Gly Ser Val Glu Lys Trp Arg Ser Gly Arg
        595                 600                 605
Gly Lys Pro Ile Pro Asn Pro Leu Leu Gly Leu Asp Ser Thr Arg Thr
    610                 615                 620
Gly
625
```

<210> SEQ ID NO 34
<211> LENGTH: 21
<212> TYPE: DNA
<213> ORGANISM: Artificial
<220> FEATURE:
<223> OTHER INFORMATION: A nucleotide sequence of MHC-IgG1, a synthetic
  oligonucleotide complementary to mouse IgG1 constant region
  sequence.

<400> SEQUENCE: 34
gggccagtgg atagacagat g          21

<210> SEQ ID NO 35
<211> LENGTH: 23
<212> TYPE: DNA
<213> ORGANISM: Artificial
<220> FEATURE:
<223> OTHER INFORMATION: A nucleotide sequence of MLC-kappa, a synthetic oligonucleotide complementary to mouse kappa chain constant region sequence.

<400> SEQUENCE: 35
gctcactgga tggtgggaag atg                                            23

<210> SEQ ID NO 36
<211> LENGTH: 363
<212> TYPE: DNA
<213> ORGANISM: Mus musculus

<400> SEQUENCE: 36
caggtccagt tgcagcagtc tggagctgag ctggtgaggc ctgggacttc agtgaagatc     60
tcctgcaagg cttctggata cgccttcact tactactggc taggttgggt aaagcagagg    120
cctggacatg gacttgagtg gattggagat atttaccctg aagtggtaa tacttactac     180 aatgagaagt tcaagggcaa agccacactg actgcagaca atcctcgag cacagcctat     240 atgcagctca gtagcctgac atctgagggc tctgctgtct atttctgtgc aagaagggcc    300
tactattata accaggtctt ctttgaccac tggggccaag gcaccactct cacagtctcc    360
tca                                                                  363

<210> SEQ ID NO 37
<211> LENGTH: 121
<212> TYPE: PRT
<213> ORGANISM: Mus musculus

<400> SEQUENCE: 37

Gln Val Gln Leu Gln Gln Ser Gly Ala Glu Leu Val Arg Pro Gly Thr
1               5                   10                  15

Ser Val Lys Ile Ser Cys Lys Ala Ser Gly Tyr Ala Phe Thr Tyr Tyr
            20                  25                  30

Trp Leu Gly Trp Val Lys Gln Arg Pro Gly His Gly Leu Glu Trp Ile
        35                  40                  45

Gly Asp Ile Tyr Pro Gly Ser Gly Asn Thr Tyr Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Gly Ser Ala Val Tyr Phe Cys
                85                  90                  95

Ala Arg Arg Ala Tyr Tyr Tyr Asn Gln Val Phe Phe Asp His Trp Gly
            100                 105                 110

Gln Gly Thr Thr Leu Thr Val Ser Ser
        115                 120

<210> SEQ ID NO 38
<211> LENGTH: 321
<212> TYPE: DNA
<213> ORGANISM: Artificial
<220> FEATURE:
<223> OTHER INFORMATION: A nucleotide sequence of VL of an antibody A1.

<400> SEQUENCE: 38
aacattgtaa tgacccaatc tcccaaatcc atgtccatgt cagtaggaga gagggtcacc     60

```
ttgacctgca aggccagtga gaatgtggtt acttatgttt cctggtatca acagaaacca      120
gagcagtctc ctaaactgct gatatacggg gcatccaacc ggtacactgg ggtccccgat      180
cgcttcacag gcagtggatc tgcaacagat ttcactctga ccatcagcag tgtgcaggct      240
gaagaccttg cagattatca ctgtggacag ggttacagct atccgtacac gttcggaggg      300
gggaccaagc tggaaataaa a                                                321
```

<210> SEQ ID NO 39
<211> LENGTH: 107
<212> TYPE: PRT
<213> ORGANISM: Artificial
<220> FEATURE:
<223> OTHER INFORMATION: An amino acid sequence of VL of an antibody A1.

<400> SEQUENCE: 39

```
Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
                85                  90                  95

Thr Phe Gly Gly Gly Thr Lys Leu Glu Ile Lys
            100                 105
```

<210> SEQ ID NO 40
<211> LENGTH: 354
<212> TYPE: DNA
<213> ORGANISM: Mus musculus

<400> SEQUENCE: 40

```
gaggttcagc tgcagcagtc tggggcagag cttgtgaggt caggggcctc agtcaagttg      60
tcctgcacag cttctggctt caacattaaa gactactata tgcactgggt gaagcagagg      120
cctgaacagg gcctggagtg gattggatgg attgatcctg agaatgatga tactgaatat      180
gccccgaagt tccagggcag ggccactatg actgctgaca catcctccaa cacagcctac      240
ctgcagctca gcagcctgac atctgaggac actgccgtct attactgtaa tgcgggttac      300
tacggtagtg ggtttgctta ctggggccaa gggactctgg tcactgtctc tgca            354
```

<210> SEQ ID NO 41
<211> LENGTH: 118
<212> TYPE: PRT
<213> ORGANISM: Mus musculus

<400> SEQUENCE: 41

```
Glu Val Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45
```

```
Gly Trp Ile Asp Pro Glu Asn Asp Asp Thr Glu Tyr Ala Pro Lys Phe
 50                  55                  60

Gln Gly Arg Ala Thr Met Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Asn Ala Gly Tyr Tyr Gly Ser Gly Phe Ala Tyr Trp Gly Gln Gly Thr
                100                 105                 110

Leu Val Thr Val Ser Ala
        115

<210> SEQ ID NO 42
<211> LENGTH: 339
<212> TYPE: DNA
<213> ORGANISM: Artificial
<220> FEATURE:
<223> OTHER INFORMATION: A nucleotide sequence of VL of an antibody A6.

<400> SEQUENCE: 42
gacattgtga tgacacagtc tccatcctcc ctgactgtga cagcaggaga gaaggtcact    60
atgaggtgca gtccagtca gagtctgtta acagtggaa atcaaaagaa ctacttgacc    120
tggtaccagc agaaaccagg gcagcctcct agactgttga tctactgggc atccattagg   180
gaatctgggg tccctgatcg cttcacaggc agtggatctg gaacagattt cactctcacc   240
atcagcagtg tgcaggctga agacctggca gtttattact gtcagaatga ttatagttat   300
cctctcacgt tcggtactgg gaccaagctg gagctgaaa                          339

<210> SEQ ID NO 43
<211> LENGTH: 113
<212> TYPE: PRT
<213> ORGANISM: Artificial
<220> FEATURE:
<223> OTHER INFORMATION: An amino acid sequence of VL of an antibody A6.

<400> SEQUENCE: 43

Asp Ile Val Met Thr Gln Ser Pro Ser Ser Leu Thr Val Thr Ala Gly
 1               5                  10                  15

Glu Lys Val Thr Met Arg Cys Lys Ser Ser Gln Ser Leu Leu Asn Ser
                 20                  25                  30

Gly Asn Gln Lys Asn Tyr Leu Thr Trp Tyr Gln Gln Lys Pro Gly Gln
             35                  40                  45

Pro Pro Arg Leu Leu Ile Tyr Trp Ala Ser Ile Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Asp Tyr Ser Tyr Pro Leu Thr Phe Gly Thr Gly Thr Lys Leu Glu Leu
                100                 105                 110

Lys

<210> SEQ ID NO 44
<211> LENGTH: 351
<212> TYPE: DNA
<213> ORGANISM: Mus musculus

<400> SEQUENCE: 44
gaggttcagc tgcagcagtc tggggcagag cttgtgaagc caggggcctc agtcaagttg    60
```

-continued

```
tcctgcacag cttctggctt caacattaaa gacacctata tgcactgggt gaagcagagg    120
cctgaacagg gcctggaatg gattggaagg attgatcctg cgaatggtaa tactaaattt    180
gacccgaagt tccagggcaa ggcctctata acagcagaca catcctccaa cacagcctac    240
ctacaactca gcagcctgac atctgaggac actgccgtct attactgtgc tacgaattta    300
ttgagggcta tggactactg gggtcaagga acctcagtca ccgtctcctc a             351
```

<210> SEQ ID NO 45
<211> LENGTH: 117
<212> TYPE: PRT
<213> ORGANISM: Mus musculus

<400> SEQUENCE: 45

```
Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Lys Phe Asp Pro Lys Phe
    50                  55                  60

Gln Gly Lys Ala Ser Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Thr Asn Leu Leu Arg Ala Met Asp Tyr Trp Gly Gln Gly Thr Ser
            100                 105                 110

Val Thr Val Ser Ser
        115
```

<210> SEQ ID NO 46
<211> LENGTH: 339
<212> TYPE: DNA
<213> ORGANISM: Artificial
<220> FEATURE:
<223> OTHER INFORMATION: A nucleotide sequence of VL of an antibody A10.

<400> SEQUENCE: 46

```
gacattgtga tgtcacagtc tccatcctcc ctaactgtgt cagttggaga aaggttact     60 atgagctgca agtccagtca gagccttta tatagtagca atcaaaagaa ctacttggcc    120
tggtgccagc agataccagg gcagtctcct aaactgctga tttactgggc atccactagg    180
gaatctgggg tccctgatcg cttcgcaggc agtggatctg gacagattt cactctcacc    240 atcagcagtg tgaaggctga agacctggca gtttattact gtctgcaata tttttaccat    300
ccattcacgt tcggctcggg gacaaagttg gaaataaaa                           339
```

<210> SEQ ID NO 47
<211> LENGTH: 113
<212> TYPE: PRT
<213> ORGANISM: Artificial
<220> FEATURE:
<223> OTHER INFORMATION: An amino acid sequence of VL of an antibody
      A10.

<400> SEQUENCE: 47

```
Asp Ile Val Met Ser Gln Ser Pro Ser Ser Leu Thr Val Ser Val Gly
1               5                   10                  15
```

-continued

```
Glu Lys Val Thr Met Ser Cys Lys Ser Ser Gln Ser Leu Leu Tyr Ser
             20                  25                  30

Ser Asn Gln Lys Asn Tyr Leu Ala Trp Cys Gln Ile Pro Gly Gln
         35                  40                  45

Ser Pro Lys Leu Leu Ile Tyr Trp Ala Ser Thr Arg Glu Ser Gly Val
 50                  55                  60

Pro Asp Arg Phe Ala Gly Ser Gly Ser Gly Thr Asp Phe Thr Leu Thr
 65                  70                  75                  80

Ile Ser Ser Val Lys Ala Glu Asp Leu Ala Val Tyr Tyr Cys Leu Gln
                 85                  90                  95

Tyr Phe Thr Tyr Pro Phe Thr Phe Gly Ser Gly Thr Lys Leu Glu Ile
             100                 105                 110

Lys
```

<210> SEQ ID NO 48
<211> LENGTH: 345
<212> TYPE: DNA
<213> ORGANISM: Mus musculus

<400> SEQUENCE: 48

```
gaagtgaagc tggtggagtc tgggggaggc ttagtgaagt ctggagggtc cctgaaactc      60
tcctgtgtag tctctggatt cactttcagt agatatgcca tgtcttgggt tcgccagact     120
ccagagaaga ggctggagtg ggtcgcctcc attgttagtg gtgataagac ctactatcca     180
gacagtgtga aggccgatt caccatctcc agagataatg ccaggaacat cctgtacctg      240
caaatgagca gtctgaggtc tgaggacacg gccatgtatt actgtacaag ggaattgggg     300
tacttcgatg tctggggcgc aggaccacg gtcaccgtct cctca                      345
```

<210> SEQ ID NO 49
<211> LENGTH: 115
<212> TYPE: PRT
<213> ORGANISM: Mus musculus

<400> SEQUENCE: 49

```
Glu Val Lys Leu Val Glu Ser Gly Gly Gly Leu Val Lys Ser Gly Gly
 1               5                  10                  15

Ser Leu Lys Leu Ser Cys Val Val Ser Gly Phe Thr Phe Ser Arg Tyr
             20                  25                  30

Ala Met Ser Trp Val Arg Gln Thr Pro Glu Lys Arg Leu Glu Trp Val
         35                  40                  45

Ala Ser Ile Val Ser Gly Asp Lys Thr Tyr Tyr Pro Asp Ser Val Lys
 50                  55                  60

Gly Arg Phe Thr Ile Ser Arg Asp Asn Ala Arg Asn Ile Leu Tyr Leu
 65                  70                  75                  80

Gln Met Ser Ser Leu Arg Ser Glu Asp Thr Ala Met Tyr Tyr Cys Thr
                 85                  90                  95

Arg Glu Leu Gly Tyr Phe Asp Val Trp Gly Ala Gly Thr Thr Val Thr
             100                 105                 110

Val Ser Ser
        115
```

<210> SEQ ID NO 50
<211> LENGTH: 339
<212> TYPE: DNA
<213> ORGANISM: Artificial
<220> FEATURE:
<223> OTHER INFORMATION: A nucleotide sequence of VL of an antibody B5.

<400> SEQUENCE: 50

```
gatgttgtga tgacccaaac tccactctcc ctgcctgtca gtcttggaga tcaagcctcc    60
atctcttgca gatctagtca gagccttgta cacagtaatg aaacaccta tttacattgg   120
tacctgcaga agccaggcca gtctccgaag ctcctgatct acaaagtttc caaccgattt   180
tctggggtcc cagacaggtt cagtggcagt ggatcaggga cagatttcac actcaagatc   240
agcagagtgg aggctgagga tctgggagtt tattttttgct ctcaaagtat acatgttcct   300
ccgctcacgt tcggtgctgg gaccaagctg agctgaaa                           339
```

<210> SEQ ID NO 51
<211> LENGTH: 113
<212> TYPE: PRT
<213> ORGANISM: Artificial
<220> FEATURE:
<223> OTHER INFORMATION: An amino acid sequence of VL of an antibody B5.

<400> SEQUENCE: 51

```
Asp Val Val Met Thr Gln Thr Pro Leu Ser Leu Pro Val Ser Leu Gly
1               5                   10                  15
Asp Gln Ala Ser Ile Ser Cys Arg Ser Ser Gln Ser Leu Val His Ser
            20                  25                  30
Asn Gly Asn Thr Tyr Leu His Trp Tyr Leu Gln Lys Pro Gly Gln Ser
        35                  40                  45
Pro Lys Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Phe Cys Ser Gln Ser
                85                  90                  95
Ile His Val Pro Pro Leu Thr Phe Gly Ala Gly Thr Lys Leu Glu Leu
            100                 105                 110
Lys
```

<210> SEQ ID NO 52
<211> LENGTH: 354
<212> TYPE: DNA
<213> ORGANISM: Mus musculus

<400> SEQUENCE: 52

```
gaggttcagc tgcagcagtc tggggcagag cttgtgaggt caggggcctc agtcaagttg    60
tcctgcacag cttctggctt caacattaaa gactactata tgcactgggt gaagcagagg   120
cctgaacagg gcctgagtg gattggatgg attgatcctg acaatggtga actactgagtat   180
gccccgaagt tccagggcaa ggccactatg actgcagaca catcctccaa cacagcctac   240
ctgcagctca gcagcctgac atctgaggac actgccgtct attactgtaa tgcagggaat   300
ggtaactact ggtttgctta ctggggccaa gggactctgg tcactgtctc tgca         354
```

<210> SEQ ID NO 53
<211> LENGTH: 118
<212> TYPE: PRT
<213> ORGANISM: Mus musculus

<400> SEQUENCE: 53

```
Glu Val Gln Leu Gln Gln Ser Gly Ala Glu Leu Val Arg Ser Gly Ala
1               5                   10                  15
```

```
Ser Val Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
            35                  40                  45

Gly Trp Ile Asp Pro Asp Asn Gly Asp Thr Glu Tyr Ala Pro Lys Phe
        50                  55                  60

Gln Gly Lys Ala Thr Met Thr Ala Asp Thr Ser Ser Asn Thr Ala Tyr
 65                 70                  75                  80

Leu Gln Leu Ser Ser Leu Thr Ser Glu Asp Thr Ala Val Tyr Tyr Cys
                85                  90                  95

Asn Ala Gly Asn Gly Asn Tyr Trp Phe Ala Tyr Trp Gly Gln Gly Thr
            100                 105                 110

Leu Val Thr Val Ser Ala
            115
```

<210> SEQ ID NO 54
<211> LENGTH: 336
<212> TYPE: DNA
<213> ORGANISM: Artificial
<220> FEATURE:
<223> OTHER INFORMATION: A nucleotide sequence of VL of an antibody B6.

<400> SEQUENCE: 54

```
gatgttgtga tgacccaaac tccactctcc ctgcctgtca gtcttggaga tcaagcctcc    60
atctcctgca gatctagtca gagccttgta cacagtaatg gaaacaccta tttacattgg   120
aacctgcaga agccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tctgggagtt tatttctgct ctcaaactac acttgttccg   300
tacacgttcg gaggggggac caagctggaa ataaaa                             336
```

<210> SEQ ID NO 55
<211> LENGTH: 112
<212> TYPE: PRT
<213> ORGANISM: Artificial
<220> FEATURE:
<223> OTHER INFORMATION: An amino acid sequence of VL of an antibody B6.

<400> SEQUENCE: 55

```
Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
            20                  25                  30

Asn Gly Asn Thr Tyr Leu His Trp Asn Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
 65                 70                  75                  80

Ser Arg Val Glu Ala Glu Asp Leu Gly Val Tyr Phe Cys Ser Gln Thr
                85                  90                  95

Thr Leu Val Pro Tyr Thr Phe Gly Gly Gly Thr Lys Leu Glu Ile Lys
            100                 105                 110
```

<210> SEQ ID NO 56
<211> LENGTH: 354
<212> TYPE: DNA
<213> ORGANISM: Mus musculus

<400> SEQUENCE: 56

```
gaggttcagc tgcagcagtc tggggcagaa cttgtgaggt caggggcctc agtcaagttg    60
tcctgcacag cttctggctt caacattaaa gactactata tgcactgggt taagcagagg   120
cctgaacagg gcctggagtg gattggatgg attgatcctg acaatgatga tactgaatat   180
gccccgaagt tccagggcaa ggccactatg actgcagaca tcctccaa cacagcctac    240
ctgcagctca gcagcctgac atctgaggac actgccgtct attactgtaa tgcagggaat   300
ggtaactact ggtttgctta ctggggccaa gggactctgg tcactgtctc tgca         354
```

<210> SEQ ID NO 57
<211> LENGTH: 118
<212> TYPE: PRT
<213> ORGANISM: Mus musculus

<400> SEQUENCE: 57

```
Glu Val Gln Leu Gln Gln Ser Gly Ala Glu Leu Val Arg Ser Gly Ala
1               5                   10                  15
Ser Val Lys Leu Ser Cys Thr Ala Ser Gly Phe Asn Ile Lys Asp Tyr
            20                  25                  30
Tyr Met His Trp Val Lys Gln Arg Pro Glu Gln Gly Leu Glu Trp Ile
        35                  40                  45
Gly Trp Ile Asp Pro Asp Asn Asp Asp Thr Glu Tyr Ala Pro Lys Phe
    50                  55                  60
Gln Gly Lys Ala Thr Met Thr Ala Asp Thr Ser Ser Asn Thr Ala Tyr
65                  70                  75                  80
Leu Gln Leu Ser Ser Leu Thr Ser Glu Asp Thr Ala Val Tyr Tyr Cys
                85                  90                  95
Asn Ala Gly Asn Gly Asn Tyr Trp Phe Ala Tyr Trp Gly Gln Gly Thr
            100                 105                 110
Leu Val Thr Val Ser Ala
        115
```

<210> SEQ ID NO 58
<211> LENGTH: 336
<212> TYPE: DNA
<213> ORGANISM: Artificial
<220> FEATURE:
<223> OTHER INFORMATION: A nucleotide sequence of VL of an antibody C8.

<400> SEQUENCE: 58

```
gatgttgtga tgacccaaac tccactctcc ctgcctgtca gtcttggaga tcaagcctcc    60
atctcctgca gatctagtca gagccttgta cacagtaatg aaacaccta tttacattgg   120
aacctgcaga agccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tctgggagtt tatttctgct ctcaaactac acttgttccg   300
tacacgttcg gaggggggac caagctggaa ataaaa                              336
```

<210> SEQ ID NO 59
<211> LENGTH: 112
<212> TYPE: PRT
<213> ORGANISM: Artificial
<220> FEATURE:
<223> OTHER INFORMATION: An amino acid sequence of VL of an antibody C8.

<400> SEQUENCE: 59

-continued

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Asn Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Thr
                85                  90                  95

Thr Leu Val Pro Tyr Thr Phe Gly Gly Gly Thr Lys Leu Glu Ile Lys
            100                 105                 110

<210> SEQ ID NO 60
<211> LENGTH: 351
<212> TYPE: DNA
<213> ORGANISM: Mus musculus

<400> SEQUENCE: 60
caggtccaac tacaccagcc tgggtctgtg ctggtgaggc ctggagcttc agtgaagctg      60
tcctgcaagg cttctggcta caccttcacc gactcctgga tgcactgggc gaagcagagg     120
cctggacaag gccttgagtg gattggagag attcgtccaa atagtggtaa gactaactat     180
aatgagaagt ttaagggcaa ggccacactg actgtagaca catcctccag cacagcctac     240
gtggatctcc gcagcctgac atctgaggac tctgcggtct attattgtgt aaggacctat     300
atgtctcact ttgactactg gggccaaggc accactctca cagtctcctc a             351

<210> SEQ ID NO 61
<211> LENGTH: 117
<212> TYPE: PRT
<213> ORGANISM: Mus musculus

<400> SEQUENCE: 61

Gln Val Gln Leu His Gln Pro Gly Ser Val Leu Val Arg Pro Gly Ala
1               5                   10                  15

Ser Val Lys Leu Ser Cys Lys Ala Ser Gly Tyr Thr Phe Thr Asp Ser
            20                  25                  30

Trp Met His Trp Ala Lys Gln Arg Pro Gly Gln Gly Leu Glu Trp Ile
        35                  40                  45

Gly Glu Ile Arg Pro Asn Ser Gly Lys Thr Asn Tyr Asn Glu Lys Phe
    50                  55                  60

Lys Gly Lys Ala Thr Leu Thr Val Asp Thr Ser Ser Ser Thr Ala Tyr
65                  70                  75                  80

Val Asp Leu Arg Ser Leu Thr Ser Glu Asp Ser Ala Val Tyr Tyr Cys
                85                  90                  95

Val Arg Thr Tyr Met Ser His Phe Asp Tyr Trp Gly Gln Gly Thr Thr
            100                 105                 110

Leu Thr Val Ser Ser
        115

<210> SEQ ID NO 62
<211> LENGTH: 336
<212> TYPE: DNA
<213> ORGANISM: Artificial
<220> FEATURE:

<223> OTHER INFORMATION: A nucleotide sequence of VL of an antibody C10.

<400> SEQUENCE: 62

```
gatattgtga tgacgcaggc tgccttctcc aatccagtca ctcttggaac atcagcttcc      60
atctcgtgca ggtctagcaa gagtctccta cacagtaatg gcatcactta tttgtattgg    120
tatctgcaga agccaggcca gtctcctcag ctcctgattt atcagatgtc caaccttgcc    180
ccaggagtcc cagacagggt cagtagcagt gggtcaggaa gtgatttcac actgagaatc    240
agcagagtgg aggctgagga tgtgggtgtt tattactgtg ctcaaaatct agaacttcca    300
ttcacgttcg gctcggggac aaggttggaa ataaaa                              336
```

<210> SEQ ID NO 63
<211> LENGTH: 112
<212> TYPE: PRT
<213> ORGANISM: Artificial
<220> FEATURE:
<223> OTHER INFORMATION: An amino acid sequence of VL of an antibody C10.

<400> SEQUENCE: 63

```
Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
                20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Leu Ala Pro Gly Val Pro
        50                  55                  60

Asp Arg Val Ser Ser Gly Ser Gly Ser Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Phe Thr Phe Gly Ser Gly Thr Arg Leu Glu Ile Lys
            100                 105                 110
```

<210> SEQ ID NO 64
<211> LENGTH: 5
<212> TYPE: PRT
<213> ORGANISM: Artificial
<220> FEATURE:
<223> OTHER INFORMATION: An amino acid sequence of VH CDR1 of an antibody A1.

<400> SEQUENCE: 64

```
Tyr Tyr Trp Leu Gly
1               5
```

<210> SEQ ID NO 65
<211> LENGTH: 17
<212> TYPE: PRT
<213> ORGANISM: Artificial
<220> FEATURE:
<223> OTHER INFORMATION: An amino acid sequence of VH CDR2 of an antibody A1.

<400> SEQUENCE: 65

```
Asp Ile Tyr Pro Gly Ser Gly Asn Thr Tyr Tyr Asn Glu Lys Phe Lys
1               5                   10                  15

Gly
```

-continued

```
<210> SEQ ID NO 66
<211> LENGTH: 12
<212> TYPE: PRT
<213> ORGANISM: Artificial
<220> FEATURE:
<223> OTHER INFORMATION: An amino acid sequence of VH CDR3 of an
      antibody A1.

<400> SEQUENCE: 66

Arg Ala Tyr Tyr Tyr Asn Gln Val Phe Phe Asp His
1               5                   10

<210> SEQ ID NO 67
<211> LENGTH: 11
<212> TYPE: PRT
<213> ORGANISM: Artificial
<220> FEATURE:
<223> OTHER INFORMATION: An amino acid sequence of VL CDR1 of an
      antibody A1.

<400> SEQUENCE: 67

Lys Ala Ser Glu Asn Val Val Thr Tyr Val Ser
1               5                   10

<210> SEQ ID NO 68
<211> LENGTH: 7
<212> TYPE: PRT
<213> ORGANISM: Artificial
<220> FEATURE:
<223> OTHER INFORMATION: An amino acid sequence of VL CDR2 of an
      antibody A1.

<400> SEQUENCE: 68

Gly Ala Ser Asn Arg Tyr Thr
1               5

<210> SEQ ID NO 69
<211> LENGTH: 9
<212> TYPE: PRT
<213> ORGANISM: Artificial
<220> FEATURE:
<223> OTHER INFORMATION: An amino acid sequence of VL CDR3 of an
      antibody A1.

<400> SEQUENCE: 69

Gly Gln Gly Tyr Ser Tyr Pro Tyr Thr
1               5

<210> SEQ ID NO 70
<211> LENGTH: 5
<212> TYPE: PRT
<213> ORGANISM: Artificial
<220> FEATURE:
<223> OTHER INFORMATION: An amino acid sequence of VH CDR1 of an
      antibody A6.

<400> SEQUENCE: 70

Asp Tyr Tyr Met His
1               5

<210> SEQ ID NO 71
<211> LENGTH: 17
<212> TYPE: PRT
<213> ORGANISM: Artificial
<220> FEATURE:
<223> OTHER INFORMATION: An amino acid sequence of VH CDR2 of an
      antibody A6.

<400> SEQUENCE: 71
```

Trp Ile Asp Pro Glu Asn Asp Asp Thr Glu Tyr Ala Pro Lys Phe Gln
1               5                   10                  15

Gly

<210> SEQ ID NO 72
<211> LENGTH: 9
<212> TYPE: PRT
<213> ORGANISM: Artificial
<220> FEATURE:
<223> OTHER INFORMATION: An amino acid sequence of VH CDR3 of an
      antibody A6.

<400> SEQUENCE: 72

Gly Tyr Tyr Gly Ser Gly Phe Ala Tyr
1               5

<210> SEQ ID NO 73
<211> LENGTH: 17
<212> TYPE: PRT
<213> ORGANISM: Artificial
<220> FEATURE:
<223> OTHER INFORMATION: An amino acid sequence of VL CDR1 of an
      antibody A6.

<400> SEQUENCE: 73

Lys Ser Ser Gln Ser Leu Leu Asn Ser Gly Asn Gln Lys Asn Tyr Leu
1               5                   10                  15

Thr

<210> SEQ ID NO 74
<211> LENGTH: 7
<212> TYPE: PRT
<213> ORGANISM: Artificial
<220> FEATURE:
<223> OTHER INFORMATION: An amino acid sequence of VL CDR2 of an
      antibody A6.

<400> SEQUENCE: 74

Trp Ala Ser Ile Arg Glu Ser
1               5

<210> SEQ ID NO 75
<211> LENGTH: 9
<212> TYPE: PRT
<213> ORGANISM: Artificial
<220> FEATURE:
<223> OTHER INFORMATION: An amino acid sequence of VL CDR3 of an
      antibody A6.

<400> SEQUENCE: 75

Gln Asn Asp Tyr Ser Tyr Pro Leu Thr
1               5

<210> SEQ ID NO 76
<211> LENGTH: 5
<212> TYPE: PRT
<213> ORGANISM: Artificial
<220> FEATURE:
<223> OTHER INFORMATION: An amino acid sequence of VH CDR1 of an
      antibody A10.

<400> SEQUENCE: 76

Asp Thr Tyr Met His
1               5

```
<210> SEQ ID NO 77
<211> LENGTH: 17
<212> TYPE: PRT
<213> ORGANISM: Artificial
<220> FEATURE:
<223> OTHER INFORMATION: An amino acid sequence of VH CDR2 of an
      antibody A10.

<400> SEQUENCE: 77

Arg Ile Asp Pro Ala Asn Gly Asn Thr Lys Phe Asp Pro Lys Phe Gln
1               5                   10                  15

Gly

<210> SEQ ID NO 78
<211> LENGTH: 8
<212> TYPE: PRT
<213> ORGANISM: Artificial
<220> FEATURE:
<223> OTHER INFORMATION: An amino acid sequence of VH CDR3 of an
      antibody A10.

<400> SEQUENCE: 78

Asn Leu Leu Arg Ala Met Asp Tyr
1               5

<210> SEQ ID NO 79
<211> LENGTH: 17
<212> TYPE: PRT
<213> ORGANISM: Artificial
<220> FEATURE:
<223> OTHER INFORMATION: An amino acid sequence of VL CDR1 of an
      antibody A10.

<400> SEQUENCE: 79

Lys Ser Ser Gln Ser Leu Leu Tyr Ser Ser Asn Gln Lys Asn Tyr Leu
1               5                   10                  15

Ala

<210> SEQ ID NO 80
<211> LENGTH: 7
<212> TYPE: PRT
<213> ORGANISM: Artificial
<220> FEATURE:
<223> OTHER INFORMATION: An amino acid sequence of VL CDR2 of an
      antibody A10.

<400> SEQUENCE: 80

Trp Ala Ser Thr Arg Glu Ser
1               5

<210> SEQ ID NO 81
<211> LENGTH: 9
<212> TYPE: PRT
<213> ORGANISM: Artificial
<220> FEATURE:
<223> OTHER INFORMATION: An amino acid sequence of VL CDR3 of an
      antibody A10.

<400> SEQUENCE: 81

Leu Gln Tyr Phe Thr Tyr Pro Phe Thr
1               5

<210> SEQ ID NO 82
<211> LENGTH: 5
<212> TYPE: PRT
<213> ORGANISM: Artificial
<220> FEATURE:
```

<223> OTHER INFORMATION: An amino acid sequence of VH CDR1 of an
      antibody B5.

<400> SEQUENCE: 82

Arg Tyr Ala Met Ser
1               5

<210> SEQ ID NO 83
<211> LENGTH: 16
<212> TYPE: PRT
<213> ORGANISM: Artificial
<220> FEATURE:
<223> OTHER INFORMATION: An amino acid sequence of VH CDR2 of an
      antibody B5.

<400> SEQUENCE: 83

Ser Ile Val Ser Gly Asp Lys Thr Tyr Tyr Pro Asp Ser Val Lys Gly
1               5                   10                  15

<210> SEQ ID NO 84
<211> LENGTH: 7
<212> TYPE: PRT
<213> ORGANISM: Artificial
<220> FEATURE:
<223> OTHER INFORMATION: An amino acid sequence of VH CDR3 of an
      antibody B5.

<400> SEQUENCE: 84

Glu Leu Gly Tyr Phe Asp Val
1               5

<210> SEQ ID NO 85
<211> LENGTH: 16
<212> TYPE: PRT
<213> ORGANISM: Artificial
<220> FEATURE:
<223> OTHER INFORMATION: An amino acid sequence of VL CDR1 of an
      antibody B5.

<400> SEQUENCE: 85

Arg Ser Ser Gln Ser Leu Val His Ser Asn Gly Asn Thr Tyr Leu His
1               5                   10                  15

<210> SEQ ID NO 86
<211> LENGTH: 7
<212> TYPE: PRT
<213> ORGANISM: Artificial
<220> FEATURE:
<223> OTHER INFORMATION: An amino acid sequence of VL CDR2 of an
      antibody B5.

<400> SEQUENCE: 86

Lys Val Ser Asn Arg Phe Ser
1               5

<210> SEQ ID NO 87
<211> LENGTH: 10
<212> TYPE: PRT
<213> ORGANISM: Artificial
<220> FEATURE:
<223> OTHER INFORMATION: An amino acid sequence of VL CDR3 of an
      antibody B5.

<400> SEQUENCE: 87

Ser Gln Ser Ile His Val Pro Pro Leu Thr
1               5                   10

<210> SEQ ID NO 88
<211> LENGTH: 5
<212> TYPE: PRT
<213> ORGANISM: Artificial
<220> FEATURE:
<223> OTHER INFORMATION: An amino acid sequence of VH CDR1 of an
      antibody B6.

<400> SEQUENCE: 88

Asp Tyr Tyr Met His
1               5

<210> SEQ ID NO 89
<211> LENGTH: 17
<212> TYPE: PRT
<213> ORGANISM: Artificial
<220> FEATURE:
<223> OTHER INFORMATION: An amino acid sequence of VH CDR2 of an
      antibody B6.

<400> SEQUENCE: 89

Trp Ile Asp Pro Asp Asn Gly Asp Thr Glu Tyr Ala Pro Lys Phe Gln
1               5                   10                  15
Gly

<210> SEQ ID NO 90
<211> LENGTH: 9
<212> TYPE: PRT
<213> ORGANISM: Artificial
<220> FEATURE:
<223> OTHER INFORMATION: An amino acid sequence of VH CDR3 of an
      antibody B6.

<400> SEQUENCE: 90

Gly Asn Gly Asn Tyr Trp Phe Ala Tyr
1               5

<210> SEQ ID NO 91
<211> LENGTH: 16
<212> TYPE: PRT
<213> ORGANISM: Artificial
<220> FEATURE:
<223> OTHER INFORMATION: An amino acid sequence of VL CDR1 of an
      antibody B6.

<400> SEQUENCE: 91

Arg Ser Ser Gln Ser Leu Val His Ser Asn Gly Asn Thr Tyr Leu His
1               5                   10                  15

<210> SEQ ID NO 92
<211> LENGTH: 7
<212> TYPE: PRT
<213> ORGANISM: Artificial
<220> FEATURE:
<223> OTHER INFORMATION: An amino acid sequence of VL CDR2 of an
      antibody B6.

<400> SEQUENCE: 92

Lys Val Ser Asn Arg Phe Ser
1               5

<210> SEQ ID NO 93
<211> LENGTH: 9
<212> TYPE: PRT
<213> ORGANISM: Artificial
<220> FEATURE:
<223> OTHER INFORMATION: An amino acid sequence of VL CDR3 of an
      antibody B6.

```
<400> SEQUENCE: 93

Ser Gln Thr Thr Leu Val Pro Tyr Thr
1               5

<210> SEQ ID NO 94
<211> LENGTH: 5
<212> TYPE: PRT
<213> ORGANISM: Artificial
<220> FEATURE:
<223> OTHER INFORMATION: An amino acid sequence of VH CDR1 of an
      antibody C8.

<400> SEQUENCE: 94

Asp Tyr Tyr Met His
1               5

<210> SEQ ID NO 95
<211> LENGTH: 17
<212> TYPE: PRT
<213> ORGANISM: Artificial
<220> FEATURE:
<223> OTHER INFORMATION: An amino acid sequence of VH CDR2 of an
      antibody C8.

<400> SEQUENCE: 95

Trp Ile Asp Pro Asp Asn Asp Thr Glu Tyr Ala Pro Lys Phe Gln
1               5                   10                  15

Gly

<210> SEQ ID NO 96
<211> LENGTH: 9
<212> TYPE: PRT
<213> ORGANISM: Artificial
<220> FEATURE:
<223> OTHER INFORMATION: An amino acid sequence of VH CDR3 of an
      antibody C8.

<400> SEQUENCE: 96

Gly Asn Gly Asn Tyr Trp Phe Ala Tyr
1               5

<210> SEQ ID NO 97
<211> LENGTH: 16
<212> TYPE: PRT
<213> ORGANISM: Artificial
<220> FEATURE:
<223> OTHER INFORMATION: An amino acid sequence of VL CDR1 of an
      antibody C8.

<400> SEQUENCE: 97

Arg Ser Ser Gln Ser Leu Val His Ser Asn Gly Asn Thr Tyr Leu His
1               5                   10                  15

<210> SEQ ID NO 98
<211> LENGTH: 7
<212> TYPE: PRT
<213> ORGANISM: Artificial
<220> FEATURE:
<223> OTHER INFORMATION: An amino acid sequence of VL CDR2 of an
      antibody C8.

<400> SEQUENCE: 98

Lys Val Ser Asn Arg Phe Ser
1               5
```

```
<210> SEQ ID NO 99
<211> LENGTH: 9
<212> TYPE: PRT
<213> ORGANISM: Artificial
<220> FEATURE:
<223> OTHER INFORMATION: An amino acid sequence of VL CDR3 of an
      antibody C8.

<400> SEQUENCE: 99

Ser Gln Thr Thr Leu Val Pro Tyr Thr
1               5

<210> SEQ ID NO 100
<211> LENGTH: 5
<212> TYPE: PRT
<213> ORGANISM: Artificial
<220> FEATURE:
<223> OTHER INFORMATION: An amino acid sequence of VH CDR1 of an
      antibody C10.

<400> SEQUENCE: 100

Asp Ser Trp Met His
1               5

<210> SEQ ID NO 101
<211> LENGTH: 17
<212> TYPE: PRT
<213> ORGANISM: Artificial
<220> FEATURE:
<223> OTHER INFORMATION: An amino acid sequence of VH CDR2 of an
      antibody C10.

<400> SEQUENCE: 101

Glu Ile Arg Pro Asn Ser Gly Lys Thr Asn Tyr Asn Glu Lys Phe Lys
1               5                   10                  15

Gly

<210> SEQ ID NO 102
<211> LENGTH: 8
<212> TYPE: PRT
<213> ORGANISM: Artificial
<220> FEATURE:
<223> OTHER INFORMATION: An amino acid sequence of VH CDR3 of an
      antibody C10.

<400> SEQUENCE: 102

Thr Tyr Met Ser His Phe Asp Tyr
1               5

<210> SEQ ID NO 103
<211> LENGTH: 16
<212> TYPE: PRT
<213> ORGANISM: Artificial
<220> FEATURE:
<223> OTHER INFORMATION: An amino acid sequence of VL CDR1 of an
      antibody C10.

<400> SEQUENCE: 103

Arg Ser Ser Lys Ser Leu Leu His Ser Asn Gly Ile Thr Tyr Leu Tyr
1               5                   10                  15

<210> SEQ ID NO 104
<211> LENGTH: 7
<212> TYPE: PRT
<213> ORGANISM: Artificial
<220> FEATURE:
<223> OTHER INFORMATION: An amino acid sequence of VL CDR2 of an
      antibody C10.
```

<400> SEQUENCE: 104

Gln Met Ser Asn Leu Ala Pro
1               5

<210> SEQ ID NO 105
<211> LENGTH: 9
<212> TYPE: PRT
<213> ORGANISM: Artificial
<220> FEATURE:
<223> OTHER INFORMATION: An amino acid sequence of VL CDR3 of an
      antibody C10.

<400> SEQUENCE: 105

Ala Gln Asn Leu Glu Leu Pro Phe Thr
1               5

<210> SEQ ID NO 106
<211> LENGTH: 605
<212> TYPE: PRT
<213> ORGANISM: Homo sapiens

<400> SEQUENCE: 106

Met Ala Leu Pro Ala Cys Ala Val Arg Glu Phe Glu Pro Pro Arg Gln
1               5                   10                  15

Pro Glu Arg Gly Ala Pro Val Arg Thr Thr Cys Pro Arg Arg His Ser
            20                  25                  30

Arg Val Glu Ala Glu Leu Ala Ala Ser Arg Pro Gly Ser Val Ala Ala
        35                  40                  45

Ser Val Arg Ala Gly Pro Pro Arg Gly Val Ser His Gly Phe His Thr
    50                  55                  60

Arg Pro Leu Leu Asp Lys Pro Arg Lys Ala Ser Ser Ser Leu Ala Gly
65                  70                  75                  80

Ala Ala Cys Ala Pro Leu Phe Ala Leu Leu Ser Arg Gly Arg Arg Arg
                85                  90                  95

Arg Met His Val Leu Arg Arg Arg Trp Asp Leu Gly Ser Leu Cys Arg
                100                 105                 110

Ala Leu Leu Thr Arg Gly Leu Ala Ala Leu Gly His Ser Leu Lys His
            115                 120                 125

Val Leu Gly Ala Ile Phe Ser Lys Ile Phe Gly Pro Met Ala Ser Val
    130                 135                 140

Gly Asn Met Asp Glu Lys Ser Asn Lys Leu Leu Leu Ala Leu Val Met
145                 150                 155                 160

Leu Phe Leu Phe Ala Val Ile Val Leu Gln Tyr Val Cys Pro Gly Thr
                165                 170                 175

Glu Cys Gln Leu Leu Arg Leu Gln Ala Phe Ser Ser Pro Val Pro Asp
            180                 185                 190

Pro Tyr Arg Ser Glu Asp Glu Ser Ser Ala Arg Phe Val Pro Arg Tyr
        195                 200                 205

Asn Phe Thr Arg Gly Asp Leu Leu Arg Lys Val Asp Phe Asp Ile Lys
    210                 215                 220

Gly Asp Asp Leu Ile Val Phe Leu His Ile Gln Lys Thr Gly Gly Thr
225                 230                 235                 240

Thr Phe Gly Arg His Leu Val Arg Asn Ile Gln Leu Glu Gln Pro Cys
                245                 250                 255

Glu Cys Arg Val Gly Gln Lys Lys Cys Thr Cys His Arg Pro Gly Lys
            260                 265                 270

Arg Glu Thr Trp Leu Phe Ser Arg Phe Ser Thr Gly Ser Cys Gly
                275                 280                 285

Leu His Ala Asp Trp Thr Glu Leu Thr Ser Cys Val Pro Ser Val Val
290                 295                 300

Asp Gly Lys Arg Asp Ala Arg Leu Arg Pro Ser Arg Asn Phe His Tyr
305                 310                 315                 320

Ile Thr Ile Leu Arg Asp Pro Val Ser Arg Tyr Leu Ser Glu Trp Arg
                325                 330                 335

His Val Gln Arg Gly Ala Thr Trp Lys Ala Ser Leu His Val Cys Asp
            340                 345                 350

Gly Arg Pro Pro Thr Ser Glu Glu Leu Pro Ser Cys Tyr Thr Gly Asp
        355                 360                 365

Asp Trp Ser Gly Cys Pro Leu Lys Glu Phe Met Asp Cys Pro Tyr Asn
    370                 375                 380

Leu Ala Asn Asn Arg Gln Val Arg Met Leu Ser Asp Leu Thr Leu Val
385                 390                 395                 400

Gly Cys Tyr Asn Leu Ser Val Met Pro Glu Lys Gln Arg Asn Lys Val
                405                 410                 415

Leu Leu Glu Ser Ala Lys Ser Asn Leu Lys His Met Ala Phe Phe Gly
            420                 425                 430

Leu Thr Glu Phe Gln Arg Lys Thr Gln Tyr Leu Phe Glu Lys Thr Phe
        435                 440                 445

Asn Met Asn Phe Ile Ser Pro Phe Thr Gln Tyr Asn Thr Thr Arg Ala
    450                 455                 460

Ser Ser Val Glu Ile Asn Glu Glu Ile Gln Lys Arg Ile Glu Gly Leu
465                 470                 475                 480

Asn Phe Leu Asp Met Glu Leu Tyr Ser Tyr Ala Lys Asp Leu Phe Leu
                485                 490                 495

Gln Arg Tyr Gln Phe Met Arg Gln Lys Glu His Gln Glu Ala Arg Arg
            500                 505                 510

Lys Arg Gln Glu Gln Arg Lys Phe Leu Lys Gly Arg Leu Leu Gln Thr
        515                 520                 525

His Phe Gln Ser Gln Gly Gln Gly Gln Ser Gln Asn Pro Asn Gln Asn
    530                 535                 540

Gln Ser Gln Asn Pro Asn Pro Asn Ala Asn Gln Asn Leu Thr Gln Asn
545                 550                 555                 560

Leu Met Gln Asn Leu Thr Gln Ser Leu Ser Gln Lys Glu Asn Arg Glu
                565                 570                 575

Ser Pro Lys Gln Asn Ser Gly Lys Glu Gln Asn Asp Asn Thr Ser Asn
            580                 585                 590

Gly Thr Asn Asp Tyr Ile Gly Ser Val Glu Lys Trp Arg
        595                 600                 605

<210> SEQ ID NO 107
<211> LENGTH: 459
<212> TYPE: PRT
<213> ORGANISM: Homo sapiens

<400> SEQUENCE: 107

Met Asp Glu Lys Ser Asn Lys Leu Leu Leu Ala Leu Val Met Leu Phe
1               5                   10                  15

Leu Phe Ala Val Ile Val Leu Gln Tyr Val Cys Pro Gly Thr Glu Cys
                20                  25                  30

Gln Leu Leu Arg Leu Gln Ala Phe Ser Ser Pro Val Pro Asp Pro Tyr
            35                  40                  45

```
Arg Ser Glu Asp Glu Ser Ser Ala Arg Phe Val Pro Arg Tyr Asn Phe
         50                  55                  60

Thr Arg Gly Asp Leu Leu Arg Lys Val Asp Phe Asp Ile Lys Gly Asp
 65                  70                  75                  80

Asp Leu Ile Val Phe Leu His Ile Gln Lys Thr Gly Gly Thr Thr Phe
                     85                  90                  95

Gly Arg His Leu Val Arg Asn Ile Gln Leu Glu Gln Pro Cys Glu Cys
                100                 105                 110

Arg Val Gly Gln Lys Lys Cys Thr Cys His Arg Pro Gly Lys Arg Glu
                115                 120                 125

Thr Trp Leu Phe Ser Arg Phe Ser Thr Gly Trp Ser Cys Gly Leu His
130                 135                 140

Ala Asp Trp Thr Glu Leu Thr Ser Cys Val Pro Ser Val Val Asp Gly
145                 150                 155                 160

Lys Arg Asp Ala Arg Leu Arg Pro Ser Arg Asn Phe His Tyr Ile Thr
                165                 170                 175

Ile Leu Arg Asp Pro Val Ser Arg Tyr Leu Ser Glu Trp Arg His Val
                180                 185                 190

Gln Arg Gly Ala Thr Trp Lys Ala Ser Leu His Val Cys Asp Gly Arg
                195                 200                 205

Pro Pro Thr Ser Glu Glu Leu Pro Ser Cys Tyr Thr Gly Asp Asp Trp
210                 215                 220

Ser Gly Cys Pro Leu Lys Glu Phe Met Asp Cys Pro Tyr Asn Leu Ala
225                 230                 235                 240

Asn Asn Arg Gln Val Arg Met Leu Ser Asp Leu Thr Leu Val Gly Cys
                245                 250                 255

Tyr Asn Leu Ser Val Met Pro Glu Lys Gln Arg Asn Lys Val Leu Leu
                260                 265                 270

Glu Ser Ala Lys Ser Asn Leu Lys His Met Ala Phe Phe Gly Leu Thr
                275                 280                 285

Glu Phe Gln Arg Lys Thr Gln Tyr Leu Phe Glu Lys Thr Phe Asn Met
290                 295                 300

Asn Phe Ile Ser Pro Phe Thr Gln Tyr Asn Thr Thr Arg Ala Ser Ser
305                 310                 315                 320

Val Glu Ile Asn Glu Glu Ile Gln Lys Arg Ile Glu Gly Leu Asn Phe
                325                 330                 335

Leu Asp Met Glu Leu Tyr Ser Tyr Ala Lys Asp Leu Phe Leu Gln Arg
                340                 345                 350

Tyr Gln Phe Met Arg Gln Lys Glu His Gln Glu Ala Arg Arg Lys Arg
                355                 360                 365

Gln Glu Gln Arg Lys Phe Leu Lys Gly Arg Leu Leu Gln Thr His Phe
                370                 375                 380

Gln Ser Gln Gly Gln Gly Gln Ser Gln Asn Pro Asn Gln Asn Gln Ser
385                 390                 395                 400

Gln Asn Pro Asn Pro Asn Ala Asn Gln Leu Thr Gln Asn Leu Met
                    405                 410                 415

Gln Asn Leu Thr Gln Ser Leu Ser Gln Lys Glu Asn Arg Glu Ser Pro
                420                 425                 430

Lys Gln Asn Ser Gly Lys Glu Gln Asn Asp Asn Thr Ser Asn Gly Thr
                435                 440                 445

Asn Asp Tyr Ile Gly Ser Val Glu Lys Trp Arg
450                 455
```

<210> SEQ ID NO 108
<211> LENGTH: 499
<212> TYPE: PRT
<213> ORGANISM: Homo sapiens

<400> SEQUENCE: 108

```
Met Asp Glu Lys Ser Asn Lys Leu Leu Ala Leu Val Met Leu Phe
1               5                   10                  15

Leu Phe Ala Val Ile Val Leu Gln Tyr Val Cys Pro Gly Thr Glu Cys
            20                  25                  30

Gln Leu Leu Arg Leu Gln Ala Phe Ser Ser Pro Val Pro Asp Pro Tyr
                35                  40                  45

Arg Ser Glu Asp Glu Ser Ser Ala Arg Phe Val Pro Arg Tyr Asn Phe
        50                  55                  60

Thr Arg Gly Asp Leu Leu Arg Lys Val Asp Phe Asp Ile Lys Gly Asp
65                  70                  75                  80

Asp Leu Ile Val Phe Leu His Ile Gln Lys Thr Gly Gly Thr Thr Phe
                85                  90                  95

Gly Arg His Leu Val Arg Asn Ile Gln Leu Glu Gln Pro Cys Glu Cys
            100                 105                 110

Arg Val Gly Gln Lys Lys Cys Thr Cys His Arg Pro Gly Lys Arg Glu
        115                 120                 125

Thr Trp Leu Phe Ser Arg Phe Ser Thr Gly Trp Ser Cys Gly Leu His
130                 135                 140

Ala Asp Trp Thr Glu Leu Thr Ser Cys Val Pro Ser Val Val Asp Gly
145                 150                 155                 160

Lys Arg Asp Ala Arg Leu Arg Pro Ser Arg Trp Arg Ile Phe Gln Ile
                165                 170                 175

Leu Asp Ala Ala Ser Lys Asp Lys Arg Gly Ser Pro Asn Thr Asn Ala
            180                 185                 190

Gly Ala Asn Ser Pro Ser Ser Thr Lys Thr Arg Asn Thr Ser Lys Ser
        195                 200                 205

Gly Lys Asn Phe His Tyr Ile Thr Ile Leu Arg Asp Pro Val Ser Arg
210                 215                 220

Tyr Leu Ser Glu Trp Arg His Val Gln Arg Gly Ala Thr Trp Lys Ala
225                 230                 235                 240

Ser Leu His Val Cys Asp Gly Arg Pro Pro Thr Ser Glu Glu Leu Pro
                245                 250                 255

Ser Cys Tyr Thr Gly Asp Asp Trp Ser Gly Cys Pro Leu Lys Glu Phe
            260                 265                 270

Met Asp Cys Pro Tyr Asn Leu Ala Asn Asn Arg Gln Val Arg Met Leu
        275                 280                 285

Ser Asp Leu Thr Leu Val Gly Cys Tyr Asn Leu Ser Val Met Pro Glu
290                 295                 300

Lys Gln Arg Asn Lys Val Leu Leu Glu Ser Ala Lys Ser Asn Leu Lys
305                 310                 315                 320

His Met Ala Phe Phe Gly Leu Thr Glu Phe Gln Arg Lys Thr Gln Tyr
                325                 330                 335

Leu Phe Glu Lys Thr Phe Asn Met Asn Phe Ile Ser Pro Phe Thr Gln
            340                 345                 350

Tyr Asn Thr Thr Arg Ala Ser Ser Val Glu Ile Asn Glu Glu Ile Gln
        355                 360                 365

Lys Arg Ile Glu Gly Leu Asn Phe Leu Asp Met Glu Leu Tyr Ser Tyr
370                 375                 380
```

```
Ala Lys Asp Leu Phe Leu Gln Arg Tyr Gln Phe Met Arg Gln Lys Glu
385                 390                 395                 400

His Gln Glu Ala Arg Lys Arg Gln Glu Gln Arg Lys Phe Leu Lys
            405                 410                 415

Gly Arg Leu Leu Gln Thr His Phe Gln Ser Gly Gln Gly Gln Ser
            420                 425                 430

Gln Asn Pro Asn Gln Asn Gln Ser Gln Asn Pro Asn Pro Asn Ala Asn
            435                 440                 445

Gln Asn Leu Thr Gln Asn Leu Met Gln Asn Leu Thr Gln Ser Leu Ser
450                 455                 460

Gln Lys Glu Asn Arg Glu Ser Pro Lys Gln Asn Ser Gly Lys Glu Gln
465                 470                 475                 480

Asn Asp Asn Thr Ser Asn Gly Thr Asn Asp Tyr Ile Gly Ser Val Glu
            485                 490                 495

Lys Trp Arg
```

<210> SEQ ID NO 109
<211> LENGTH: 4
<212> TYPE: PRT
<213> ORGANISM: Artificial
<220> FEATURE:
<223> OTHER INFORMATION: Amino acid sequence of a peptide linker.

<400> SEQUENCE: 109

```
Gly Gly Gly Ser
1
```

<210> SEQ ID NO 110
<211> LENGTH: 4
<212> TYPE: PRT
<213> ORGANISM: Artificial
<220> FEATURE:
<223> OTHER INFORMATION: Amino acid sequence of a peptide linker.

<400> SEQUENCE: 110

```
Ser Gly Gly Gly
1
```

<210> SEQ ID NO 111
<211> LENGTH: 5
<212> TYPE: PRT
<213> ORGANISM: Artificial
<220> FEATURE:
<223> OTHER INFORMATION: Amino acid sequence of a peptide linker.

<400> SEQUENCE: 111

```
Gly Gly Gly Gly Ser
1               5
```

<210> SEQ ID NO 112
<211> LENGTH: 5
<212> TYPE: PRT
<213> ORGANISM: Artificial
<220> FEATURE:
<223> OTHER INFORMATION: Amino acid sequence of a peptide linker.

<400> SEQUENCE: 112

```
Ser Gly Gly Gly Gly
1               5
```

<210> SEQ ID NO 113
<211> LENGTH: 6

```
<212> TYPE: PRT
<213> ORGANISM: Artificial
<220> FEATURE:
<223> OTHER INFORMATION: Amino acid sequence of a peptide linker.

<400> SEQUENCE: 113

Gly Gly Gly Gly Gly Ser
1               5

<210> SEQ ID NO 114
<211> LENGTH: 6
<212> TYPE: PRT
<213> ORGANISM: Artificial
<220> FEATURE:
<223> OTHER INFORMATION: Amino acid sequence of a peptide linker.

<400> SEQUENCE: 114

Ser Gly Gly Gly Gly Gly
1               5

<210> SEQ ID NO 115
<211> LENGTH: 7
<212> TYPE: PRT
<213> ORGANISM: Artificial
<220> FEATURE:
<223> OTHER INFORMATION: Amino acid sequence of a peptide linker.

<400> SEQUENCE: 115

Gly Gly Gly Gly Gly Gly Ser
1               5

<210> SEQ ID NO 116
<211> LENGTH: 7
<212> TYPE: PRT
<213> ORGANISM: Artificial
<220> FEATURE:
<223> OTHER INFORMATION: Amino acid sequence of a peptide linker.

<400> SEQUENCE: 116

Ser Gly Gly Gly Gly Gly Gly
1               5
```